United States Patent
Cho et al.

(10) Patent No.: US 8,986,996 B2
(45) Date of Patent: Mar. 24, 2015

(54) LARGE-SCALE PROPAGATION AND MAINTENANCE METHOD OF EMBRYOID BODIES GENERATED FROM STEM CELLS

(71) Applicant: Korea Research Institute of Bioscience and Biotechnology, Daejeon (KR)

(72) Inventors: Yee Sook Cho, Daejeon (KR); Mi Young Son, Daejeon (KR); Hyun Jin Kim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/669,896

(22) Filed: Nov. 6, 2012

(65) Prior Publication Data
US 2013/0224856 A1    Aug. 29, 2013

Related U.S. Application Data

(63) Continuation-in-part of application No. PCT/KR2011/003439, filed on May 9, 2011.

(30) Foreign Application Priority Data

May 7, 2010   (KR) .......................... 10-2010-0043211

(51) Int. Cl.
| | |
|---|---|
| C12N 5/071 | (2010.01) |
| C12N 5/0735 | (2010.01) |
| C12N 5/073 | (2010.01) |
| C12M 1/32 | (2006.01) |
| C12M 1/12 | (2006.01) |
| C12M 1/33 | (2006.01) |
| C12M 1/00 | (2006.01) |

(52) U.S. Cl.
CPC ............ *C12N 5/0606* (2013.01); *C12N 5/0603* (2013.01); *C12M 23/12* (2013.01); *C12M 25/06* (2013.01); *C12M 45/02* (2013.01); *C12M 45/09* (2013.01); *C12N 2509/10* (2013.01)
USPC ......................................... 435/379

(58) Field of Classification Search
USPC .................................. 435/366, 378, 379, 383
See application file for complete search history.

(56) References Cited

U.S. PATENT DOCUMENTS

| | | | |
|---|---|---|---|
| 2004/0151709 A1* | 8/2004 | Gorrochategui Barrueta et al. | ........................ 424/93.71 |
| 2006/0282913 A1* | 12/2006 | Shimizu et al. | ............... 800/278 |

OTHER PUBLICATIONS

Son et al. "Physical Passaging of Embryoid Bodies Generated from Human Pluripotent Stem Cell." (May 2011) PLoS One vol. 6, issue 5: 1-9.*
"Guidelines for Maintaining Cultured Cells" (n.d.) Life Technologies, available at http://www.lifetechnologies.com/us/en/home/references/gibco-cell-culture-basics/cell-culture-protocols/maintaining-cultured-cells.html, last accessed Jan. 27, 2014.*
Fok et al. "Shear-Controlled Single-Step Mouse Embryonic Stem cell Expansion and Embryoid Body-Based Differentiation" (2005), Stem Cell, vol. 23: 1333-1342.*
Fang et al. "Differentiation of embryoid-body cells derived from embryonic stem cells into hepatocytes in alginate microbeads in vitro" (Dec. 2007) Acta Pharmacol Sin, vol. 28, No. 12: 1924-1930.*

* cited by examiner

*Primary Examiner* — Jon P Weber
*Assistant Examiner* — Teresa E Knight
(74) *Attorney, Agent, or Firm* — Sunstein Kann Murphy & Timbers LLP

(57) ABSTRACT

The present invention relates to a large-scale propagation and maintenance method of embryoid bodies generated from stem cells. More particularly, the present invention relates to a large-scale propagation and maintenance method of embryoid bodies retaining their intrinsic characteristics for a long period of time, comprising the step of continuously subculturing embryoid bodies that are primarily produced from embryonic stem cells or from induced pluripotent stem cells. According to the method of the present invention, after preparation of embryoid bodies from a limited number of stem cells, large-scale production and maintenance of embryoid bodies can be realized by a simple mechanical subculturing method without the continuous supply of stem cells.

15 Claims, 36 Drawing Sheets

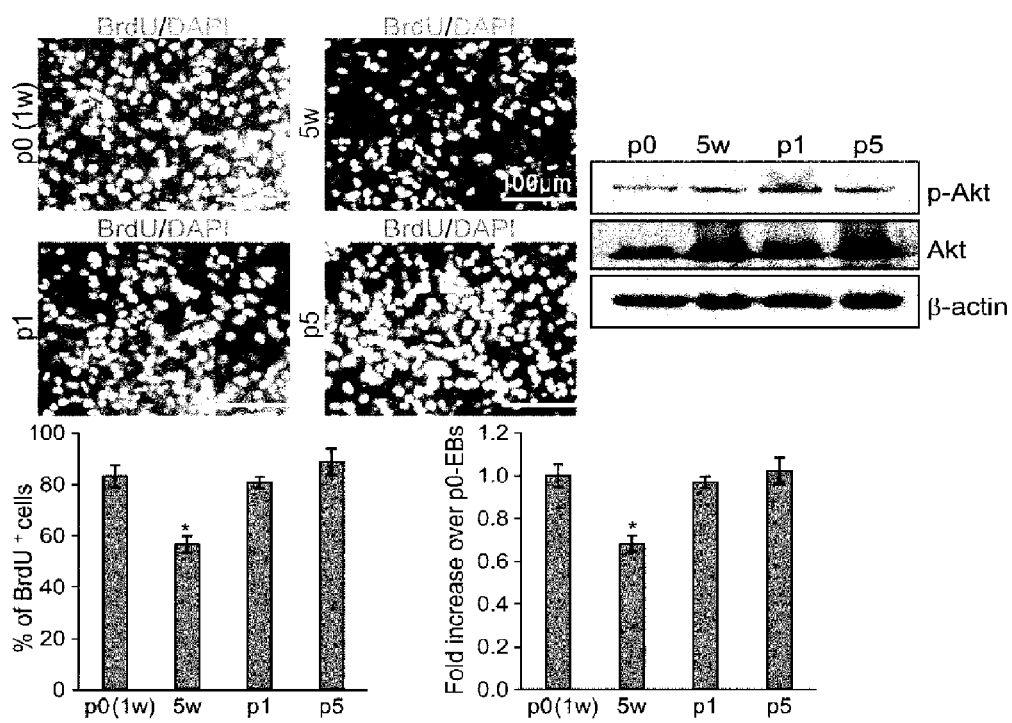

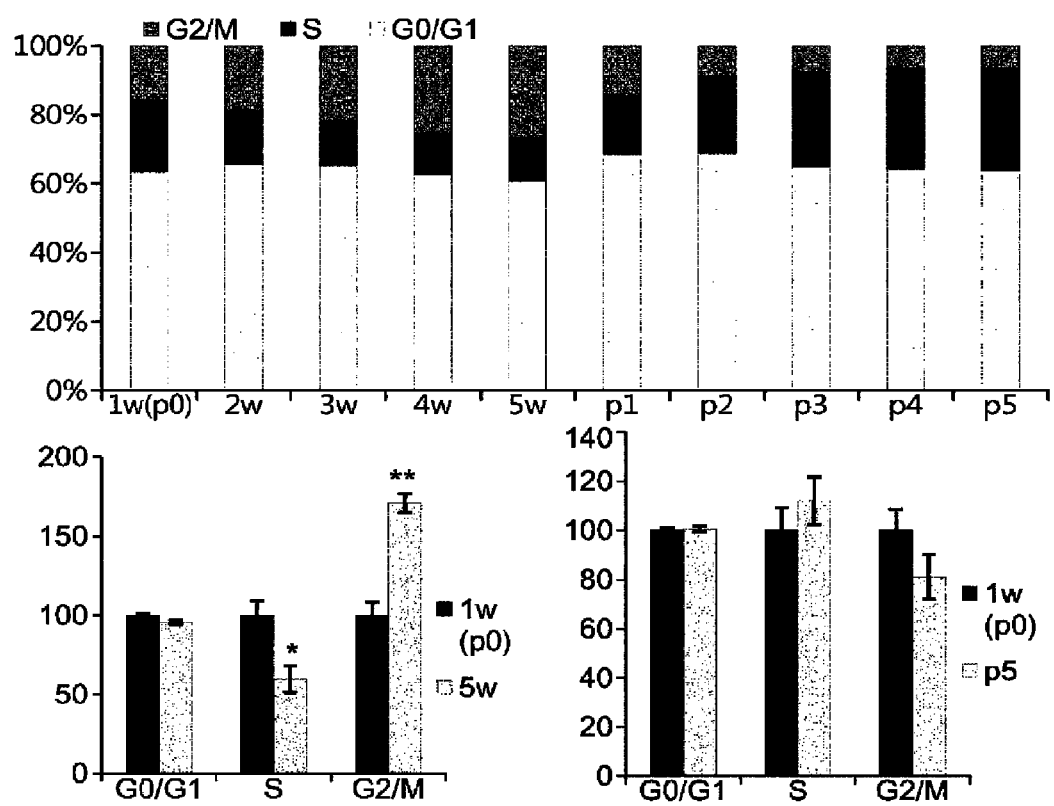

FIG. 8
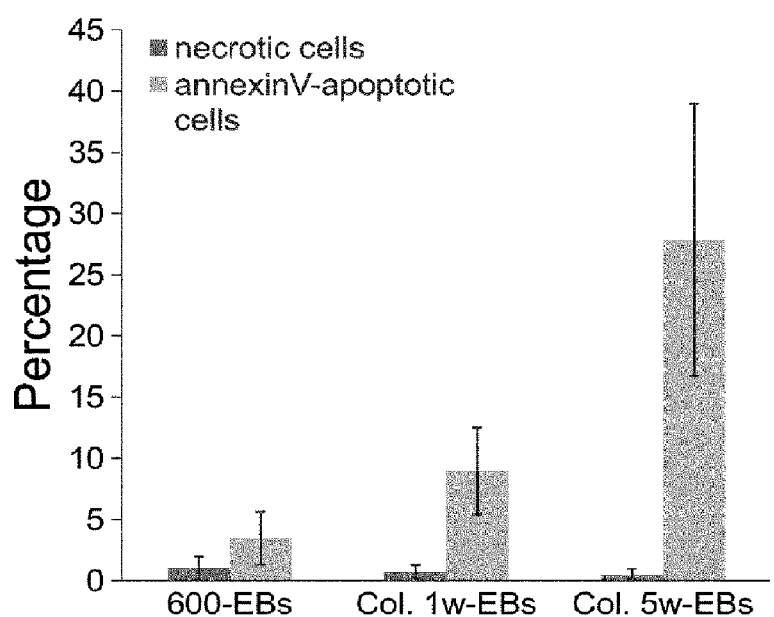
[FIG. 9a]
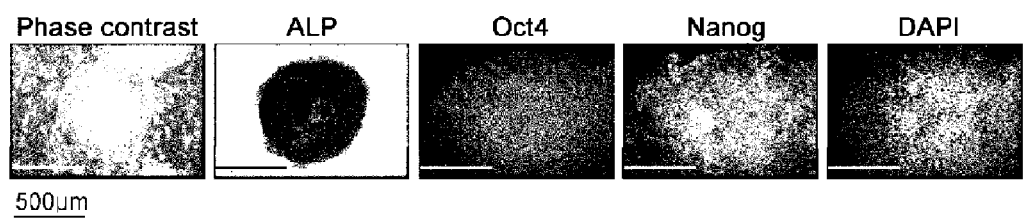

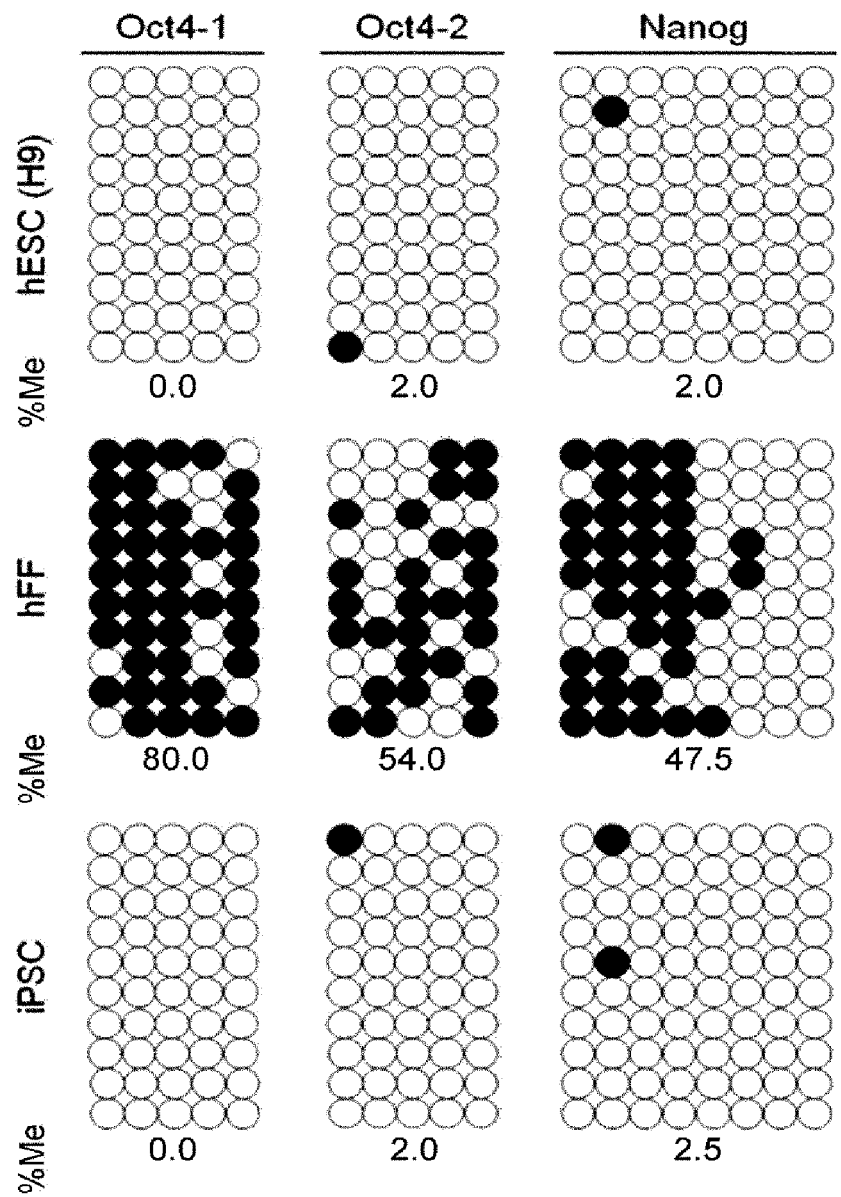

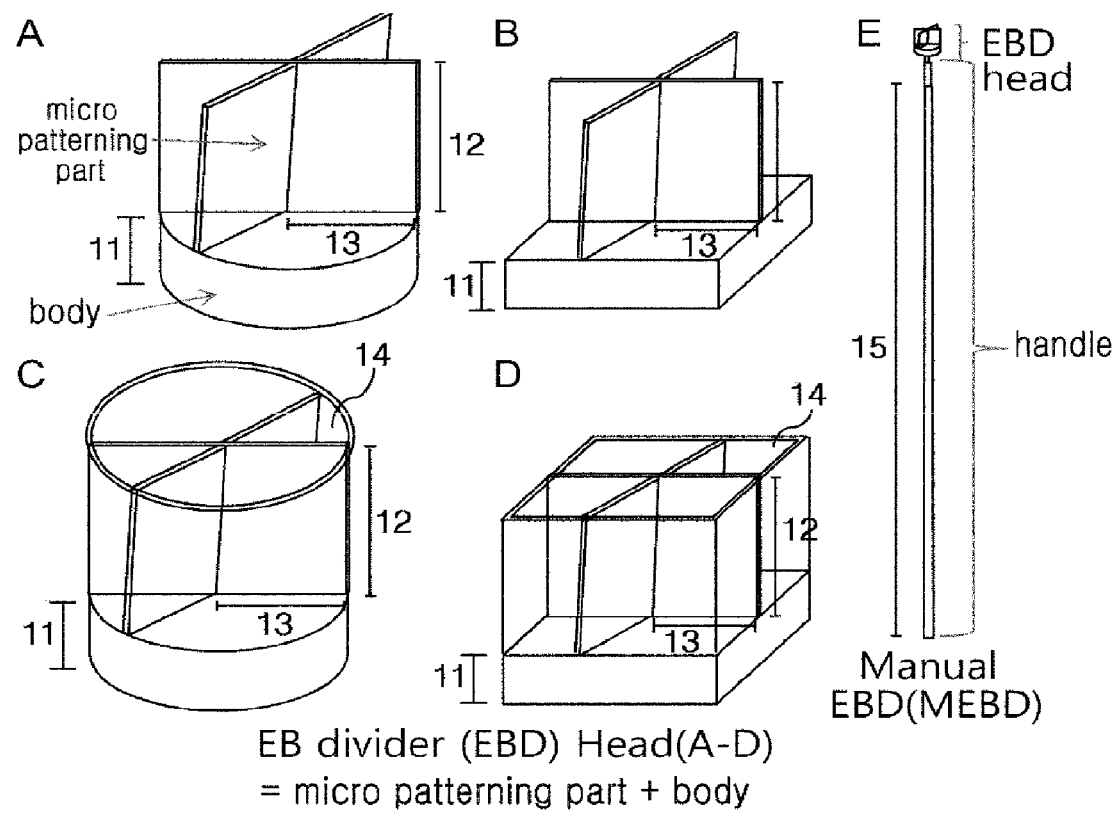

various cutting edges of micropatterning part

FIG. 12
One EBD head for one EB(A-B)    One EB-fitted container/dish(C-H)
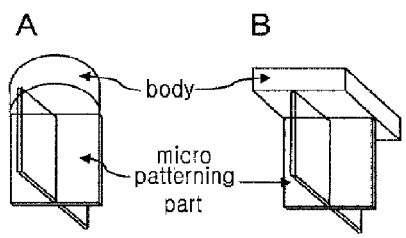
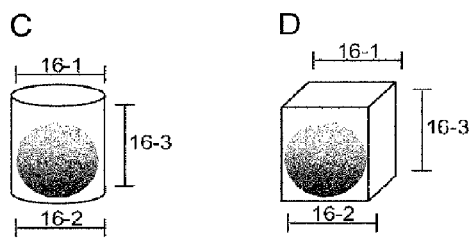
Container/dish with
conventional coating(E-G)
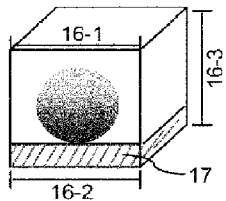
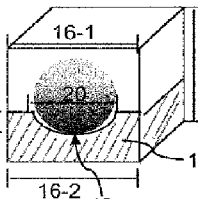
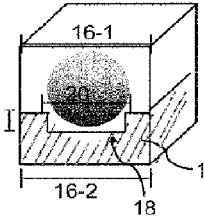
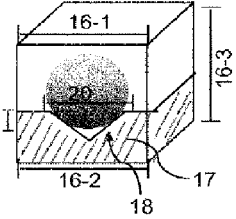
Pre-fabricated or coated-container/dish(E-G)

adjustment of blade length

EB-size fitted, multi-well plate

FIG. 19
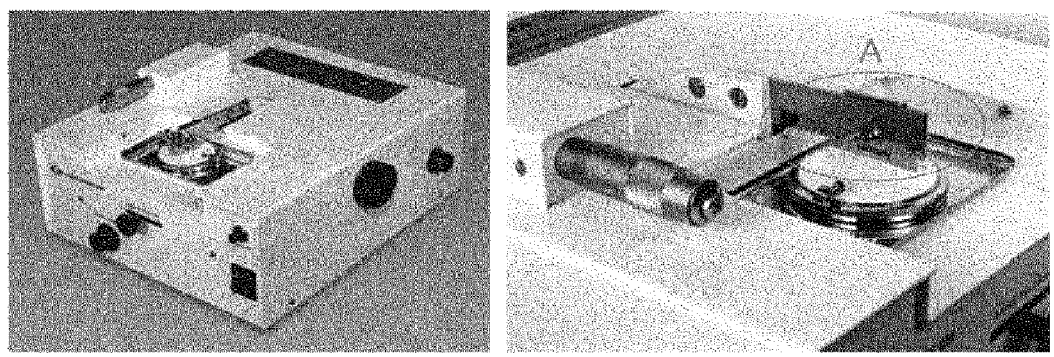
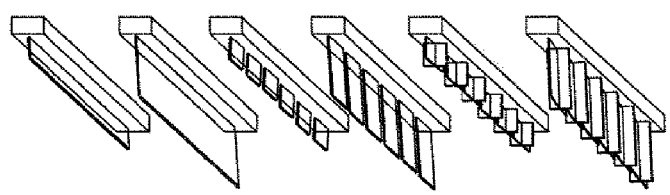
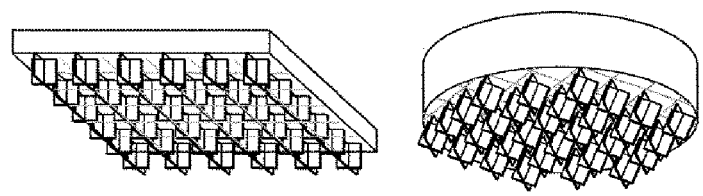

SEQUENCE LISTING

<160> NUMBER OF SEQ ID NOS: 78

<210> SEQ ID NO 1
<211> LENGTH: 24
<212> TYPE: DNA

```
<213> ORGANISM: Artificial Sequence
<220> FEATURE:
<223> OTHER INFORMATION: Endo OCT4 primer(forward)

<400> SEQUENCE: 1
gacaggggga ggggaggagc tagg                                          24

<210> SEQ ID NO 2
<211> LENGTH: 26
<212> TYPE: DNA
<213> ORGANISM: Artificial Sequence
<220> FEATURE:
<223> OTHER INFORMATION: Endo OCT4 primer(reverse)

<400> SEQUENCE: 2
cttccctcca accagttgcc ccaaac                                        26

<210> SEQ ID NO 3
<211> LENGTH: 26
<212> TYPE: DNA
<213> ORGANISM: Artificial Sequence
<220> FEATURE:
<223> OTHER INFORMATION: Endo SOX2 primer(forward)

<400> SEQUENCE: 3
gggaaatggg aggggtgcaa aagagg                                        26

<210> SEQ ID NO 4
<211> LENGTH: 26
<212> TYPE: DNA
<213> ORGANISM: Artificial Sequence
<220> FEATURE:
<223> OTHER INFORMATION: Endo SOX2 primer(reverse)

<400> SEQUENCE: 4
ttgcgtgagt gtggatggga ttggtg                                        26

<210> SEQ ID NO 5
<211> LENGTH: 25
<212> TYPE: DNA
<213> ORGANISM: Artificial Sequence
<220> FEATURE:
<223> OTHER INFORMATION: Endo KLF4 primer(forward)

<400> SEQUENCE: 5
acgatcgtgg ccccggaaaa ggacc                                         25

<210> SEQ ID NO 6
<211> LENGTH: 28
<212> TYPE: DNA
<213> ORGANISM: Artificial Sequence
<220> FEATURE:
<223> OTHER INFORMATION: Endo KLF4 primer(reverse)

<400> SEQUENCE: 6
tgattgtagt gctttctggc tgggctcc                                      28

<210> SEQ ID NO 7
<211> LENGTH: 26
<212> TYPE: DNA
<213> ORGANISM: Artificial Sequence
<220> FEATURE:
<223> OTHER INFORMATION: Endo c-Myc primer(forward)

<400> SEQUENCE: 7
gcgtcctggg aagggagatc cggagc                                        26
```

<210> SEQ ID NO 8
<211> LENGTH: 26
<212> TYPE: DNA
<213> ORGANISM: Artificial Sequence
<220> FEATURE:
<223> OTHER INFORMATION: Endo c-Myc primer(reverse)

<400> SEQUENCE: 8
ttgaggggca tcgtcgcggg aggctg                                      26

<210> SEQ ID NO 9
<211> LENGTH: 23
<212> TYPE: DNA
<213> ORGANISM: Artificial Sequence
<220> FEATURE:
<223> OTHER INFORMATION: Trans OCT4 primer(forward)

<400> SEQUENCE: 9
gagaaggatg tggtccgagt gtg                                         23

<210> SEQ ID NO 10
<211> LENGTH: 24
<212> TYPE: DNA
<213> ORGANISM: Artificial Sequence
<220> FEATURE:
<223> OTHER INFORMATION: Trans OCT4 primer(reverse)

<400> SEQUENCE: 10 cccttttict ggagactaaa taaa                                        24

<210> SEQ ID NO 11
<211> LENGTH: 26
<212> TYPE: DNA
<213> ORGANISM: Artificial Sequence
<220> FEATURE:
<223> OTHER INFORMATION: Trans SOX2 primer(forward)

<400> SEQUENCE: 11
ggcacccctg gcatggctct tggctc                                      26

<210> SEQ ID NO 12
<211> LENGTH: 24
<212> TYPE: DNA
<213> ORGANISM: Artificial Sequence
<220> FEATURE:
<223> OTHER INFORMATION: Trans SOX2 primer(reverse)

<400> SEQUENCE: 12
ttatcgtcga ccactgtgct gctg                                        24

<210> SEQ ID NO 13
<211> LENGTH: 25
<212> TYPE: DNA
<213> ORGANISM: Artificial Sequence
<220> FEATURE:
<223> OTHER INFORMATION: Trans KLF4 primer(forward)

<400> SEQUENCE: 13
acgatcgtgg ccccggaaaa ggacc                                       25

<210> SEQ ID NO 14
<211> LENGTH: 24
<212> TYPE: DNA
<213> ORGANISM: Artificial Sequence
<220> FEATURE:

<223> OTHER INFORMATION: Trans KLF4 primer(reverse)

<400> SEQUENCE: 14
ttatcgtcga ccactgtgct gctg                                          24

<210> SEQ ID NO 15
<211> LENGTH: 27
<212> TYPE: DNA
<213> ORGANISM: Artificial Sequence
<220> FEATURE:
<223> OTHER INFORMATION: Trans c-Myc primer(forward)

<400> SEQUENCE: 15
caacaaccga aaatgcacca gccccag                                       27

<210> SEQ ID NO 16
<211> LENGTH: 24
<212> TYPE: DNA
<213> ORGANISM: Artificial Sequence
<220> FEATURE:
<223> OTHER INFORMATION: Trans c-Myc primer(reverse)

<400> SEQUENCE: 16
ttatcgtcga ccactgtgct gctg                                          24

<210> SEQ ID NO 17
<211> LENGTH: 23
<212> TYPE: DNA
<213> ORGANISM: Artificial Sequence
<220> FEATURE:
<223> OTHER INFORMATION: Total OCT4 primer(forward)

<400> SEQUENCE: 17
gagaaggatg tggtccgagt gtg                                           23

<210> SEQ ID NO 18
<211> LENGTH: 22
<212> TYPE: DNA
<213> ORGANISM: Artificial Sequence
<220> FEATURE:
<223> OTHER INFORMATION: Total OCT4 primer(reverse)

<400> SEQUENCE: 18
cagaggaaag gacactggtc cc                                            22

<210> SEQ ID NO 19
<211> LENGTH: 20
<212> TYPE: DNA
<213> ORGANISM: Artificial Sequence
<220> FEATURE:
<223> OTHER INFORMATION: Total SOX2 primer(forward)

<400> SEQUENCE: 19
agaaccccaa gatgcacaac                                               20

<210> SEQ ID NO 20
<211> LENGTH: 20
<212> TYPE: DNA
<213> ORGANISM: Artificial Sequence
<220> FEATURE:
<223> OTHER INFORMATION: Total SOX2 primer(reverse)

<400> SEQUENCE: 20
atgtaggtct gcgagctggt                                               20

```
<210> SEQ ID NO 21
<211> LENGTH: 20
<212> TYPE: DNA
<213> ORGANISM: Artificial Sequence
<220> FEATURE:
<223> OTHER INFORMATION: Total KLF4 primer(forward)

<400> SEQUENCE: 21
accctgggtc ttgaggaagt                                              20

<210> SEQ ID NO 22
<211> LENGTH: 20
<212> TYPE: DNA
<213> ORGANISM: Artificial Sequence
<220> FEATURE:
<223> OTHER INFORMATION: Total KLF4 primer(reverse)

<400> SEQUENCE: 22
acgatcgtct tccctctttt                                              20

<210> SEQ ID NO 23
<211> LENGTH: 20
<212> TYPE: DNA
<213> ORGANISM: Artificial Sequence
<220> FEATURE:
<223> OTHER INFORMATION: Total c-Myc primer(forward)

<400> SEQUENCE: 23
cctaccctct caacgacagc                                              20

<210> SEQ ID NO 24
<211> LENGTH: 20
<212> TYPE: DNA
<213> ORGANISM: Artificial Sequence
<220> FEATURE:
<223> OTHER INFORMATION: Total c-Myc primer(reverse)

<400> SEQUENCE: 24
ctctgacctt ttgccaggag                                              20

<210> SEQ ID NO 25
<211> LENGTH: 20
<212> TYPE: DNA
<213> ORGANISM: Artificial Sequence
<220> FEATURE:
<223> OTHER INFORMATION: Nanog primer(forward)

<400> SEQUENCE: 25
caaaggcaaa caacccactt                                              20

<210> SEQ ID NO 26
<211> LENGTH: 20
<212> TYPE: DNA
<213> ORGANISM: Artificial Sequence
<220> FEATURE:
<223> OTHER INFORMATION: Nanog primer(reverse)

<400> SEQUENCE: 26
attgttccag gtctggttgc                                              20

<210> SEQ ID NO 27
<211> LENGTH: 20
<212> TYPE: DNA
<213> ORGANISM: Artificial Sequence
<220> FEATURE:
<223> OTHER INFORMATION: hTERT primer(forward)
```

<400> SEQUENCE: 27
cggaagagtg tctggagcaa                                              20

<210> SEQ ID NO 28
<211> LENGTH: 19
<212> TYPE: DNA
<213> ORGANISM: Artificial Sequence
<220> FEATURE:
<223> OTHER INFORMATION: hTERT primer(reverse)

<400> SEQUENCE: 28
ggatgaagcg gagtctgga                                               19

<210> SEQ ID NO 29
<211> LENGTH: 20
<212> TYPE: DNA
<213> ORGANISM: Artificial Sequence
<220> FEATURE:
<223> OTHER INFORMATION: TDGF primer(forward)

<400> SEQUENCE: 29
tccttctacg gacggaactg                                              20

<210> SEQ ID NO 30
<211> LENGTH: 20
<212> TYPE: DNA
<213> ORGANISM: Artificial Sequence
<220> FEATURE:
<223> OTHER INFORMATION: TDGF primer(reverse)

<400> SEQUENCE: 30
agaaatgcct gaggaaagca                                              20

<210> SEQ ID NO 31
<211> LENGTH: 20
<212> TYPE: DNA
<213> ORGANISM: Artificial Sequence
<220> FEATURE:
<223> OTHER INFORMATION: Rex1 primer(forward)

<400> SEQUENCE: 31
aatgcgtcat aagggGtgag                                              20

<210> SEQ ID NO 32
<211> LENGTH: 20
<212> TYPE: DNA
<213> ORGANISM: Artificial Sequence
<220> FEATURE:
<223> OTHER INFORMATION: Rex1 primer(reverse)

<400> SEQUENCE: 32
tcaatgccag gtattcctcc                                              20

<210> SEQ ID NO 33
<211> LENGTH: 20
<212> TYPE: DNA
<213> ORGANISM: Artificial Sequence
<220> FEATURE:
<223> OTHER INFORMATION: Pax6 primer(forward)

<400> SEQUENCE: 33
gccagcaaca cacctagtca                                              20

<210> SEQ ID NO 34
<211> LENGTH: 20

<212> TYPE: DNA
<213> ORGANISM: Artificial Sequence
<220> FEATURE:
<223> OTHER INFORMATION: Pax6 primer(reverse)

<400> SEQUENCE: 34
tgtgagggct gtgtctgttc                                           20

<210> SEQ ID NO 35
<211> LENGTH: 20
<212> TYPE: DNA
<213> ORGANISM: Artificial Sequence
<220> FEATURE:
<223> OTHER INFORMATION: NCAM primer(forward)

<400> SEQUENCE: 35
aggagacaga aacgaagcca                                           20

<210> SEQ ID NO 36
<211> LENGTH: 20
<212> TYPE: DNA
<213> ORGANISM: Artificial Sequence
<220> FEATURE:
<223> OTHER INFORMATION: NCAM primer(reverse)

<400> SEQUENCE: 36
ggtgttggaa atgctctggt                                           20

<210> SEQ ID NO 37
<211> LENGTH: 19
<212> TYPE: DNA
<213> ORGANISM: Artificial Sequence
<220> FEATURE:
<223> OTHER INFORMATION: GFAP primer(forward)

<400> SEQUENCE: 37
cctctccctg gctcgaatg                                            19

<210> SEQ ID NO 38
<211> LENGTH: 22
<212> TYPE: DNA
<213> ORGANISM: Artificial Sequence
<220> FEATURE:
<223> OTHER INFORMATION: GFAP primer(reverse)

<400> SEQUENCE: 38
ggaagcgaac cttctcgatg ta                                        22

<210> SEQ ID NO 39
<211> LENGTH: 20
<212> TYPE: DNA
<213> ORGANISM: Artificial Sequence
<220> FEATURE:
<223> OTHER INFORMATION: GATA2 primer(forward)

<400> SEQUENCE: 39
aaggctcgtt cctgttcaga                                           20

<210> SEQ ID NO 40
<211> LENGTH: 20
<212> TYPE: DNA
<213> ORGANISM: Artificial Sequence
<220> FEATURE:
<223> OTHER INFORMATION: GATA2 primer(reverse)

<400> SEQUENCE: 40

```
tctcctgcat gcactttgac                                              20

<210> SEQ ID NO 41
<211> LENGTH: 22
<212> TYPE: DNA
<213> ORGANISM: Artificial Sequence
<220> FEATURE:
<223> OTHER INFORMATION: cTnT primer(forward)

<400> SEQUENCE: 41
ggcagcggaa gaggatgctg aa                                           22

<210> SEQ ID NO 42
<211> LENGTH: 23
<212> TYPE: DNA
<213> ORGANISM: Artificial Sequence
<220> FEATURE:
<223> OTHER INFORMATION: cTnT primer(reverse)

<400> SEQUENCE: 42
gaggcaccaa gttgggcatg aac                                          23

<210> SEQ ID NO 43
<211> LENGTH: 22
<212> TYPE: DNA
<213> ORGANISM: Artificial Sequence
<220> FEATURE:
<223> OTHER INFORMATION: Tbx20 primer(forward)

<400> SEQUENCE: 43
ctgagccact gatccccacc ac                                           22

<210> SEQ ID NO 44
<211> LENGTH: 22
<212> TYPE: DNA
<213> ORGANISM: Artificial Sequence
<220> FEATURE:
<223> OTHER INFORMATION: Tbx20 primer(reverse)

<400> SEQUENCE: 44
ctcaggatcc acccccgaaa ag                                           22

<210> SEQ ID NO 45
<211> LENGTH: 20
<212> TYPE: DNA
<213> ORGANISM: Artificial Sequence
<220> FEATURE:
<223> OTHER INFORMATION: GATA6 primer(forward)

<400> SEQUENCE: 45
ccatgactcc aacttccacc                                              20

<210> SEQ ID NO 46
<211> LENGTH: 20
<212> TYPE: DNA
<213> ORGANISM: Artificial Sequence
<220> FEATURE:
<223> OTHER INFORMATION: GATA6 primer(reverse)

<400> SEQUENCE: 46
acggaggacg tgacttcggc                                              20

<210> SEQ ID NO 47
<211> LENGTH: 23
<212> TYPE: DNA
<213> ORGANISM: Artificial Sequence
```

```
<220> FEATURE:
<223> OTHER INFORMATION: a-FP primer(forward)

<400> SEQUENCE: 47
actgcaattg agaaacccac tgg                                            23

<210> SEQ ID NO 48
<211> LENGTH: 24
<212> TYPE: DNA
<213> ORGANISM: Artificial Sequence
<220> FEATURE:
<223> OTHER INFORMATION: a-FP primer(reverse)

<400> SEQUENCE: 48
cgatgctgga gtgggctttt tgtg                                           24

<210> SEQ ID NO 49
<211> LENGTH: 23
<212> TYPE: DNA
<213> ORGANISM: Artificial Sequence
<220> FEATURE:
<223> OTHER INFORMATION: Amylase primer(forward)

<400> SEQUENCE: 49
gctgggctca gtattcccca aat                                            23

<210> SEQ ID NO 50
<211> LENGTH: 24
<212> TYPE: DNA
<213> ORGANISM: Artificial Sequence
<220> FEATURE:
<223> OTHER INFORMATION: Amylase primer(reverse)

<400> SEQUENCE: 50
gacgacaatc tctgacctga gtag                                           24

<210> SEQ ID NO 51
<211> LENGTH: 23
<212> TYPE: DNA
<213> ORGANISM: Artificial Sequence
<220> FEATURE:
<223> OTHER INFORMATION: Albumin primer(forward)

<400> SEQUENCE: 51
cctttggcac aatgaagtgg gta                                            23

<210> SEQ ID NO 52
<211> LENGTH: 24
<212> TYPE: DNA
<213> ORGANISM: Artificial Sequence
<220> FEATURE:
<223> OTHER INFORMATION: Albumin primer(reverse)

<400> SEQUENCE: 52
cagcagtcag ccatttcacc atag                                           24

<210> SEQ ID NO 53
<211> LENGTH: 19
<212> TYPE: DNA
<213> ORGANISM: Artificial Sequence
<220> FEATURE:
<223> OTHER INFORMATION: GAPDH primer(forward)

<400> SEQUENCE: 53
gaaggtgaag gtcggagtc                                                 19
```

```
<210> SEQ ID NO 54
<211> LENGTH: 20
<212> TYPE: DNA
<213> ORGANISM: Artificial Sequence
<220> FEATURE:
<223> OTHER INFORMATION: GAPDH primer(reverse)

<400> SEQUENCE: 54
gaagatggtg atgggatttc                                                    20

<210> SEQ ID NO 55
<211> LENGTH: 20
<212> TYPE: DNA
<213> ORGANISM: Artificial Sequence
<220> FEATURE:
<223> OTHER INFORMATION: GSC primer(forward)

<400> SEQUENCE: 55
tctcaaccag ctgcactgtc                                                    20

<210> SEQ ID NO 56
<211> LENGTH: 20
<212> TYPE: DNA
<213> ORGANISM: Artificial Sequence
<220> FEATURE:
<223> OTHER INFORMATION: GSC primer(reverse)

<400> SEQUENCE: 56
ggcggttctt aaaccagacc                                                    20

<210> SEQ ID NO 57
<211> LENGTH: 21
<212> TYPE: DNA
<213> ORGANISM: Artificial Sequence
<220> FEATURE:
<223> OTHER INFORMATION: OTX1 primer(forward)

<400> SEQUENCE: 57
cactaactgg cgtgtttctg c                                                  21

<210> SEQ ID NO 58
<211> LENGTH: 18
<212> TYPE: DNA
<213> ORGANISM: Artificial Sequence
<220> FEATURE:
<223> OTHER INFORMATION: OTX1 primer(reverse)

<400> SEQUENCE: 58
aggcgtggag caaaatcg                                                      18

<210> SEQ ID NO 59
<211> LENGTH: 20
<212> TYPE: DNA
<213> ORGANISM: Artificial Sequence
<220> FEATURE:
<223> OTHER INFORMATION: OTX2 primer(forward)

<400> SEQUENCE: 59
cacttcgggt atggacttgc                                                    20

<210> SEQ ID NO 60
<211> LENGTH: 19
<212> TYPE: DNA
<213> ORGANISM: Artificial Sequence
<220> FEATURE:
<223> OTHER INFORMATION: OTX2 primer(reverse)
```

```
<400> SEQUENCE: 60
cgggtcttgg caaacagtg                                              19

<210> SEQ ID NO 61
<211> LENGTH: 25
<212> TYPE: DNA
<213> ORGANISM: Artificial Sequence
<220> FEATURE:
<223> OTHER INFORMATION: FlK1 primer(forward)

<400> SEQUENCE: 61
catatctgtc ctgatgtgat atgtc                                       25

<210> SEQ ID NO 62
<211> LENGTH: 26
<212> TYPE: DNA
<213> ORGANISM: Artificial Sequence
<220> FEATURE:
<223> OTHER INFORMATION: FlK1 primer(reverse)

<400> SEQUENCE: 62
catagcatgt cttatagtca ttgttc                                      26

<210> SEQ ID NO 63
<211> LENGTH: 20
<212> TYPE: DNA
<213> ORGANISM: Artificial Sequence
<220> FEATURE:
<223> OTHER INFORMATION: HEB1 primer(forward)

<400> SEQUENCE: 63
tgcatgtgga tcctgagaac                                             20

<210> SEQ ID NO 64
<211> LENGTH: 19
<212> TYPE: DNA
<213> ORGANISM: Artificial Sequence
<220> FEATURE:
<223> OTHER INFORMATION: HEB1 primer(reverse)

<400> SEQUENCE: 64
cgacagcaga caccagctt                                              19

<210> SEQ ID NO 65
<211> LENGTH: 22
<212> TYPE: DNA
<213> ORGANISM: Artificial Sequence
<220> FEATURE:
<223> OTHER INFORMATION: E-cadherin primer(forward)

<400> SEQUENCE: 65
cctggttcag atcaaatcca ac                                          22

<210> SEQ ID NO 66
<211> LENGTH: 19
<212> TYPE: DNA
<213> ORGANISM: Artificial Sequence
<220> FEATURE:
<223> OTHER INFORMATION: E-cadherin primer(reverse)

<400> SEQUENCE: 66
gtcaccttca gccatcctg                                              19

<210> SEQ ID NO 67
```

```
<210> SEQ ID NO 67
<211> LENGTH: 20
<212> TYPE: DNA
<213> ORGANISM: Artificial Sequence
<220> FEATURE:
<223> OTHER INFORMATION: Col1 primer(forward)

<400> SEQUENCE: 67
ggacacaatg gattgcaagg                                                 20

<210> SEQ ID NO 68
<211> LENGTH: 20
<212> TYPE: DNA
<213> ORGANISM: Artificial Sequence
<220> FEATURE:
<223> OTHER INFORMATION: Col1 primer(reverse)

<400> SEQUENCE: 68
taaccactgc tccactctgg                                                 20

<210> SEQ ID NO 69
<211> LENGTH: 20
<212> TYPE: DNA
<213> ORGANISM: Artificial Sequence
<220> FEATURE:
<223> OTHER INFORMATION: Col2 primer(forward)

<400> SEQUENCE: 69
ccgcggrgag ccatgattcg                                                 20

<210> SEQ ID NO 70
<211> LENGTH: 22
<212> TYPE: DNA
<213> ORGANISM: Artificial Sequence
<220> FEATURE:
<223> OTHER INFORMATION: Col2 primer(reverse)

<400> SEQUENCE: 70
caggcccagg aggtcctttg gg                                              22

<210> SEQ ID NO 71
<211> LENGTH: 20
<212> TYPE: DNA
<213> ORGANISM: Artificial Sequence
<220> FEATURE:
<223> OTHER INFORMATION: Musashi1 primer(forward)

<400> SEQUENCE: 71
acccccacat tctctcactg                                                 20

<210> SEQ ID NO 72
<211> LENGTH: 20
<212> TYPE: DNA
<213> ORGANISM: Artificial Sequence
<220> FEATURE:
<223> OTHER INFORMATION: Musashi1 primer(reverse)

<400> SEQUENCE: 72
aaacccaaaa cacgaacagc                                                 20

<210> SEQ ID NO 73
<211> LENGTH: 20
<212> TYPE: DNA
<213> ORGANISM: Artificial Sequence
<220> FEATURE:
<223> OTHER INFORMATION: Sox1 primer(forward)

<400> SEQUENCE: 73
```

-continued

```
gggaaaacgg gcaaataat                                                    20

<210> SEQ ID NO 74
<211> LENGTH: 20
<212> TYPE: DNA
<213> ORGANISM: Artificial Sequence
<220> FEATURE:
<223> OTHER INFORMATION: Sox1 primer(reverse)

<400> SEQUENCE: 74
ccatctgggc ttcaagtgtt                                                   20

<210> SEQ ID NO 75
<211> LENGTH: 20
<212> TYPE: DNA
<213> ORGANISM: Artificial Sequence
<220> FEATURE:
<223> OTHER INFORMATION: Tuj1 primer(forward)

<400> SEQUENCE: 75
acctcaacca cctggtatcg                                                   20

<210> SEQ ID NO 76
<211> LENGTH: 20
<212> TYPE: DNA
<213> ORGANISM: Artificial Sequence
<220> FEATURE:
<223> OTHER INFORMATION: Tuj1 primer(reverse)

<400> SEQUENCE: 76
gggtaccact ccacgaagta                                                   20

<210> SEQ ID NO 77
<211> LENGTH: 21
<212> TYPE: DNA
<213> ORGANISM: Artificial Sequence
<220> FEATURE:
<223> OTHER INFORMATION: Nestin primer(forward)

<400> SEQUENCE: 77
aacagcgacg gaggttctct a                                                 21

<210> SEQ ID NO 78
<211> LENGTH: 20
<212> TYPE: DNA
<213> ORGANISM: Artificial Sequence
<220> FEATURE:
<223> OTHER INFORMATION: Nestin primer(reverse)

<400> SEQUENCE: 78
ttctcttgtc ccgcagactt                                                   20
```

LARGE-SCALE PROPAGATION AND MAINTENANCE METHOD OF EMBRYOID BODIES GENERATED FROM STEM CELLS

CROSS REFERENCE TO RELATED APPLICATIONS

This application is a continuation-in-part of International Patent Application No. PCT/KR2011/003439, filed on May 9, 2011, the disclosure of which is incorporated herein by reference in its entirety for all purposes.

SEQUENCE LISTING

The instant application contains a Sequence Listing which has been submitted in ASCII format via EFS-Web and is hereby incorporated by reference in its entirety. Said ASCII copy, created on Jan. 24, 2013, is named 91698CIP311624-SequenceListing-ST25.txt and is 15,657 bytes in size.

BACKGROUND OF THE INVENTION

1. Field of the Invention

The present invention relates to a large-scale propagation and maintenance method of embryoid bodies generated from stem cells. More particularly, the present invention relates to a large-scale propagation and maintenance method of embryoid bodies retaining their intrinsic characteristics for a long period of time, comprising the step of continuously subculturing embryoid bodies that are primarily generated from embryonic stem cells or from induced pluripotent stem cells, an EBD for dividing embryoid body, and a culture vessel for culturing embryoid bodies.

2. Description of the Related Art

Stem cells have a strong self-renewal capacity that enables these cells to regenerate damaged tissue, and thus have been recently recognized as an important biological source in regenerative medicine and medical technology development. Stem cell-based technologies are expected to create a highly valuable new industry subset in the future medical industry, and are expected to have tremendous impact on other industrial fields. In particular, differentiation-induction technology used to obtain functionally superior tissue-specific differentiated cells from stem cells is recognized as a core technology likely to greatly expand the future stem cell industry.

Pluripotent human embryonic stem cells (hESC) retain an ability to differentiate into any cell type present in the body, and thus are regarded as an attractive cell source for obtaining differentiated cells. Technology to obtain differentiated cells from hESC has been competitively developed worldwide. Tissue-specific differentiated cells from human stem cells provide great opportunities for basic research in human development, cell therapy, and the testing of the efficacy and cytotoxicity of candidate drugs. The demand for tissue-specific differentiated cells is continuously increasing.

Since a de-differentiation strategy using de-differentiation transcription factors was successfully developed by Dr. Yamanaka in Japan, 2006 (Takahashi et al, Cell, 2006), many research groups have conducted investigations into human induced pluripotent stem cells (iPSC), that is, pluripotent stem cells similar to human embryonic stem cells that can be generated from human somatic cells (Takahashi et al, Cell, 2007; Yu et al, Science, 2007; Park et al, Cell, 2008). As successful development of de-differentiation strategy makes it possible to generate pluripotent stem cells from patient somatic cells in a comparatively easy way, utilization of patient-derived iPSC for development of basic and applied technology will rapidly grow. Tissue-specific differentiated cells from human stem cells provide great opportunities for basic research in human development, cell therapy, and testing of the efficacy and cytotoxicity of candidate drugs. The demand for tissue-specific differentiated cells is continuously increasing.

The differentiation-induction technique for the maintenance and proliferation of undifferentiated hESCs and hiPSCs involves varied and time-consuming methods for increasing the number of cells, which is a major drawback to the development of related techniques. Currently, most protocols for generating differentiated cells from hESCs and hiPSCs proceed by way of the formation of embryoid bodies. That is, in vitro tissue-specific differentiation of hESCs and hiPSCs requires an initial spontaneous formation of embryoid bodies (EBs) in suspension cultures, which is a common and critical intermediate for the induction of lineage-specific differentiation. The conventional methods of forming embryoid bodies have limitations in that the production yield considerably depends on the number of the starting stem cells, and the formed embryoid bodies are heterogeneous in size and number. For this reason, current studies have been made to develop a formation and culturing system of human embryoid bodies using multiwall and microfabrication techniques as well as stirred and mixed suspension culture systems (Cameron, C. M. et al., Biotechnol Bioeng 94, 938-948, 2006; Gerecht-Nir, S. et al., Biotechnol Bioeng 86, 493-502, 2004; Moeller, H. C. et al., Biomaterials 29, 752-763, 2008; Torisawa, Y. S. et al., Lab Chip 7, 770-776, 2007). However, current differentiation techniques using embryoid bodies absolutely depend on the supply of qualified hESCs or hiPSCs in terms of both quantity and quality. For differentiation induction, healthy, qualified, undifferentiated hESCs or hiPSCs should be obtained at first, and embryoid bodies are formed and produced in 1:1 correspondence. The number of embryoid bodies increases for a predetermined period (approximately 2 weeks), but tends to decrease thereafter, and thus there is a need to obtain a large number of undifferentiated hESCs or hiPSCs at the starting point, in order to increase the number of differentiated cells. That is, a major bottleneck in efficient differentiation is a failure to acquire a large number of undifferentiated hESCs or hiPSCs, which require varied, time-consuming methods.

Accordingly, the present inventors have made many efforts to develop a method capable of mass-producing embryoid bodies which are a mother of differentiated cells, while reducing dependency on the use of undifferentiated pluripotent stem cells. As a result, they have established a method for continuously culturing embryoid bodies through a simple subculture process. During this process, they found that the method allows for the long-term maintenance and culture (for over 20 continuous passages) of EB-constituting cell populations without loss of their survival, proliferation, and differentiation (into three germ layers). Further, micropatterning techniques have been developed for the improvement of differentiation from embryoid bodies, but the large scale-production of the initial material of undifferentiated hESCs and hiPSCs is essential for the scale-up propagation of embryoid bodies in the current techniques. That is, since the current techniques absolutely depend on the availability of undifferentiated hESCs and hiPSCs, there has been no progression in the improvement of large-scale production systems of embryoid bodies. Automatic systems have been developed to improve the culture conditions of embryoid bodies. These systems contribute to effective maintenance of embryoid bodies once formed for a predetermined period of time, but do not satisfy the demand for large-scale production thereof. In order to solve this problem, the present inventors have developed a method for large-scale production of embryoid bodies by uniform dividing and subculturing, thereby completing the present invention.

SUMMARY OF THE INVENTION

An object of the present invention is to provide a method for large-scale propagation of embryoid bodies, comprising the step of subculturing embryoid bodies that are generated from stem cells.

Another object of the present invention is to provide an EBD for dividing embryoid body.

Still another object of the present invention is to provide a culture vessel for culturing embryoid bodies.

Effect of the Invention

The method of the present invention allows easy, inexpensive, rapid large-scale production of homogenous embryoid bodies from a limited number of stem cells, in particular, hESCs or hiPSCs, and thus can be used for induced differentiation of almost all cell types, and ultimately used for the development of a technique to obtain a large amount of differentiated cells and progenitor cells. Further, a differentiation technique using embryoid bodies generated from patient-derived hiPSCs could greatly contribute to the development of the medical industry in the future, provide a rapid and improved method for the application of human stem cell-derived products, and therapy and drug discovery.

According to the culturing method of embryoid bodies of the present invention, a large amount of embryoid bodies can be divided in a very short time, thereby remarkably improving the speed of subculturing, and the manipulation time is additionally reduced, thereby providing optimal conditions for improving cell survival and maintaining their intrinsic characteristics.

According to the present invention, embryoid bodies can be effectively divided using an EBD for dividing embryoid body (MEBD, AEBD) without the enzymatic treatment, thereby producing regular-sized embryoid bodies in a short time. Thus, it allows the continuous long-term culture of embryoid bodies with high quality so as to improve the large-scale culture system for embryoid bodies, which directly contributes to EB-applied differentiation method/protocol standardization and quality improvement, leading to production of highly valuable products.

Further, the EBD system according to the present invention utilizes a culture vessel for embryoid bodies capable of producing embryoid bodies having a uniform size and shape (culture container, multi-well plate, etc.), an embryoid body dispenser, and an EBD head, MEBD, AEBD. Thus, the subculturing procedure including culture and division of the embryoid body can be performed in a single system, which reduces time consumption and the possibility of contamination during the cell culture procedure, and allows the large-scale production of embryoid bodies with high quality without continuous supply of the raw stem cell material. Therefore, the present invention could greatly contribute to the utilization of stem cells and the improvement of their industrial value in biomedical technologies, including cell therapy and drug discovery.

Figure 1A:
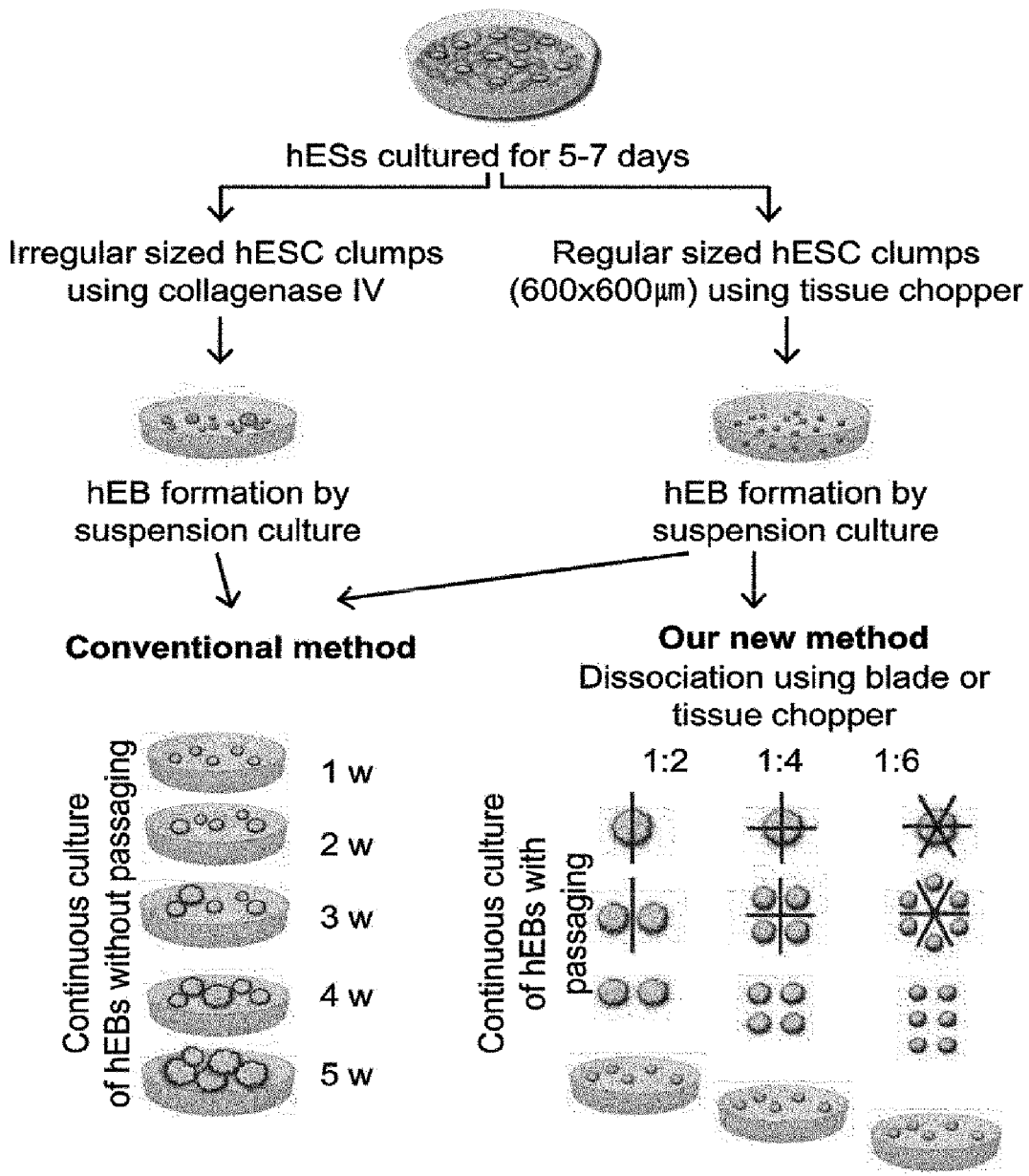
FIG. 1 shows propagation of embryoid bodies derived from hESCs and hiPSCs by long-term, periodic passaging.
Figure 11:
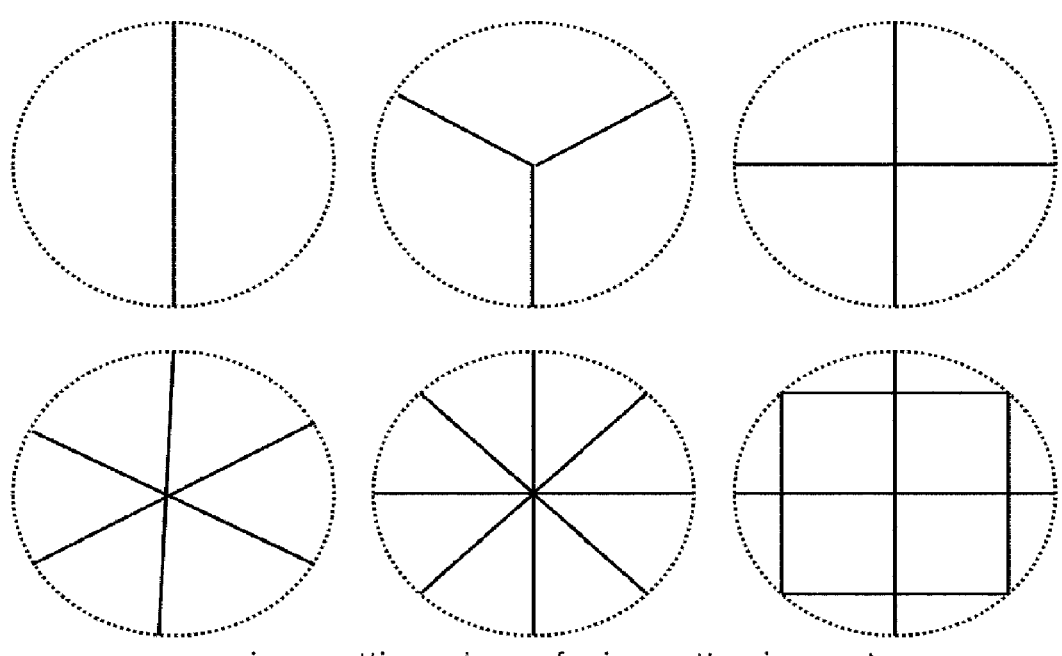
Figure 13:
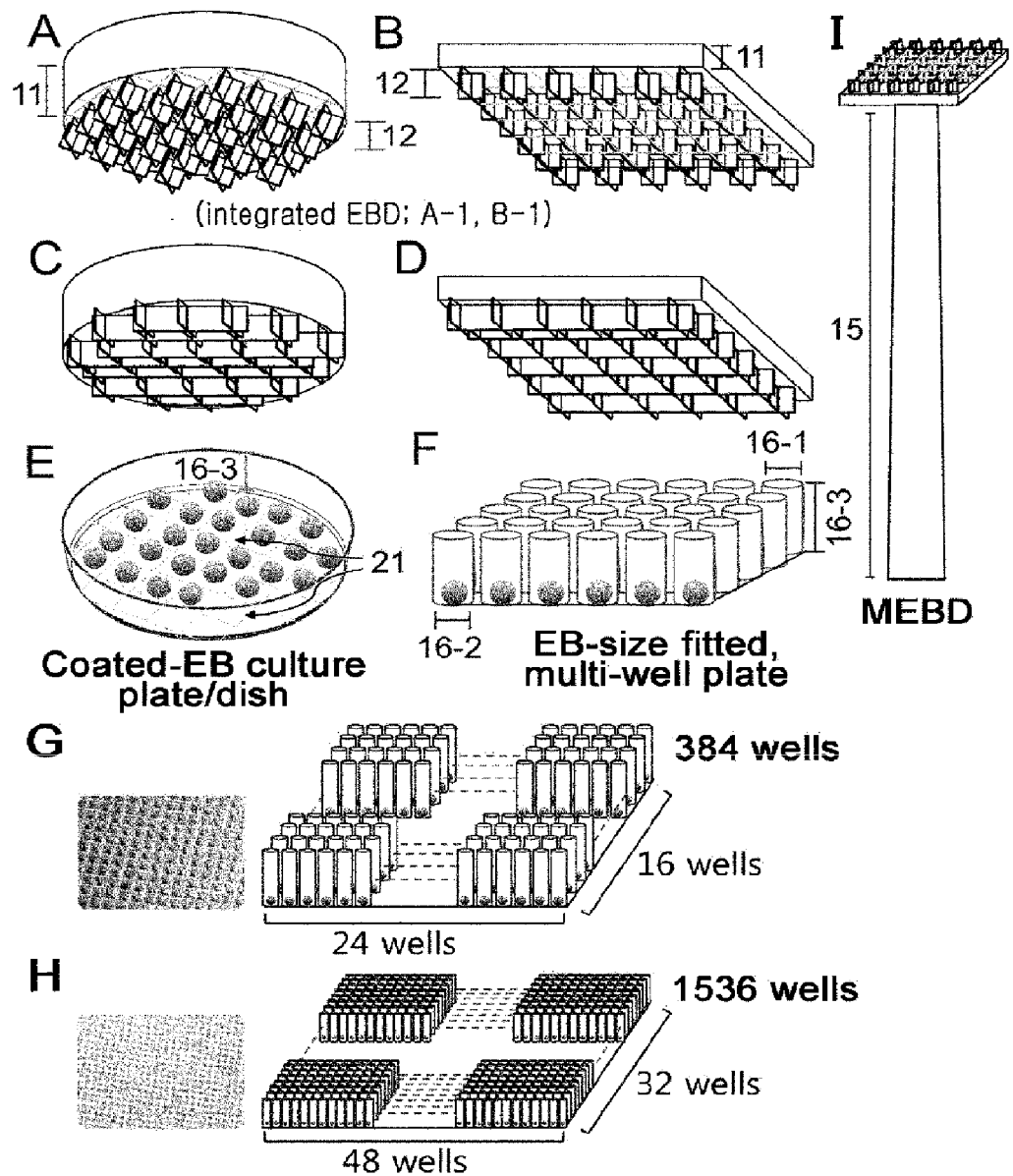
Figure 14:
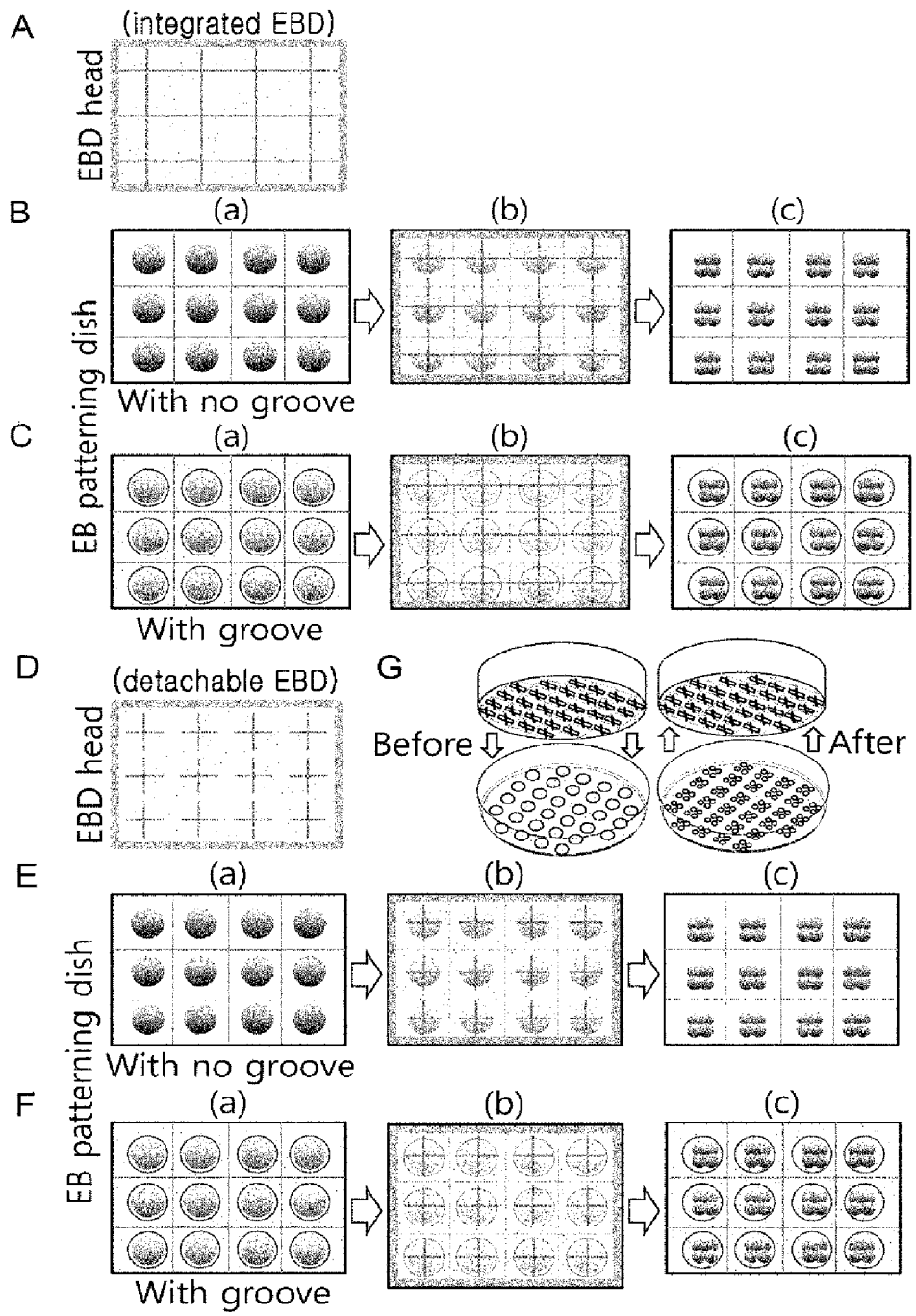
Figure 15:
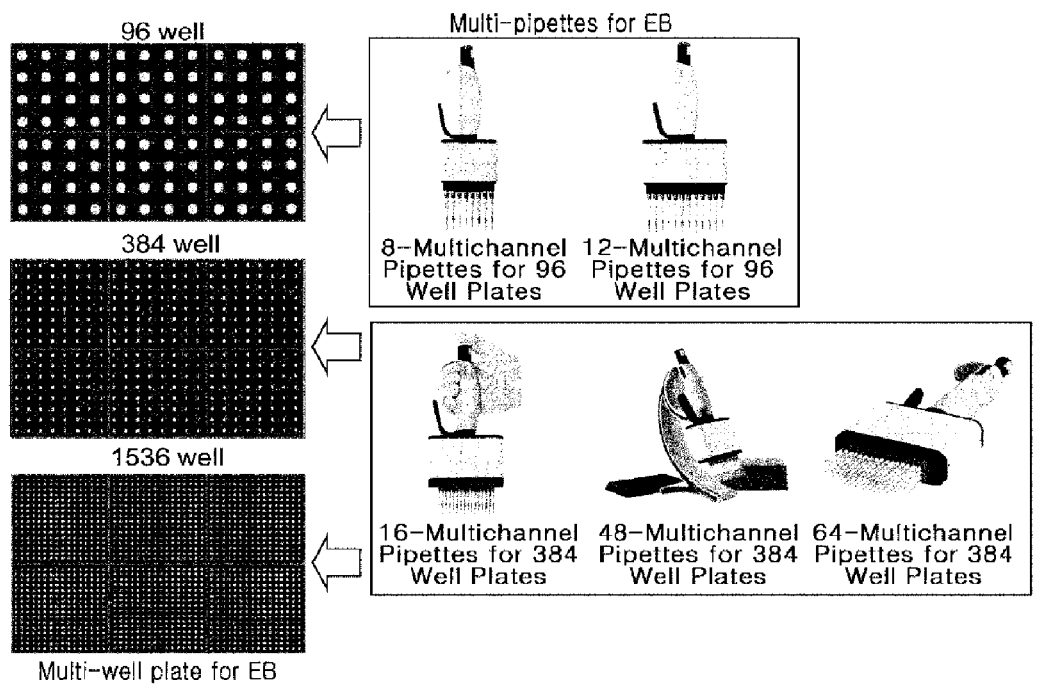
Figure 16:
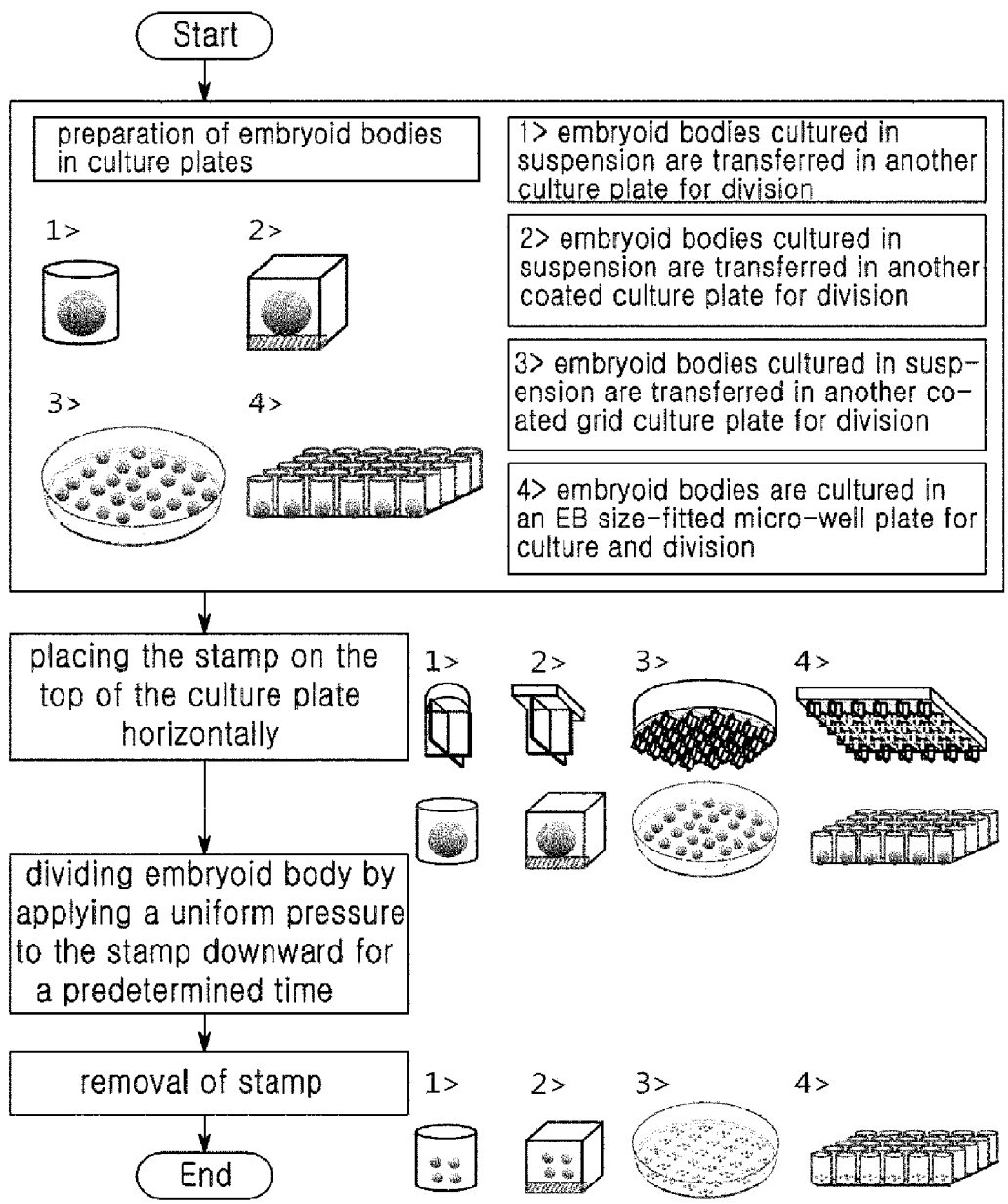
Figure 17:
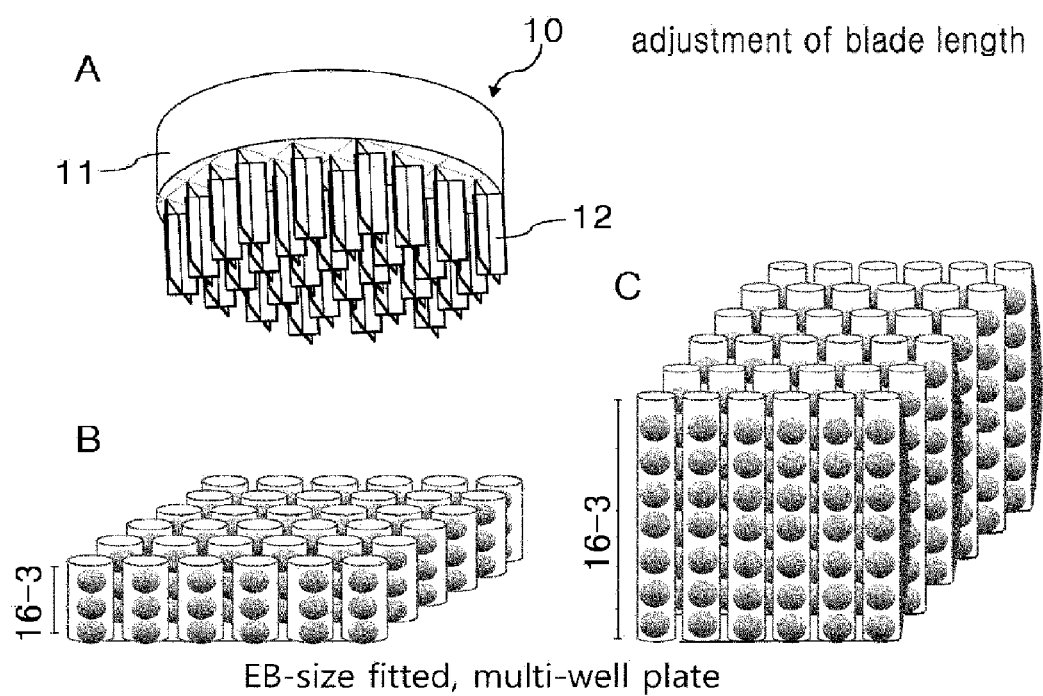
Figure 18:
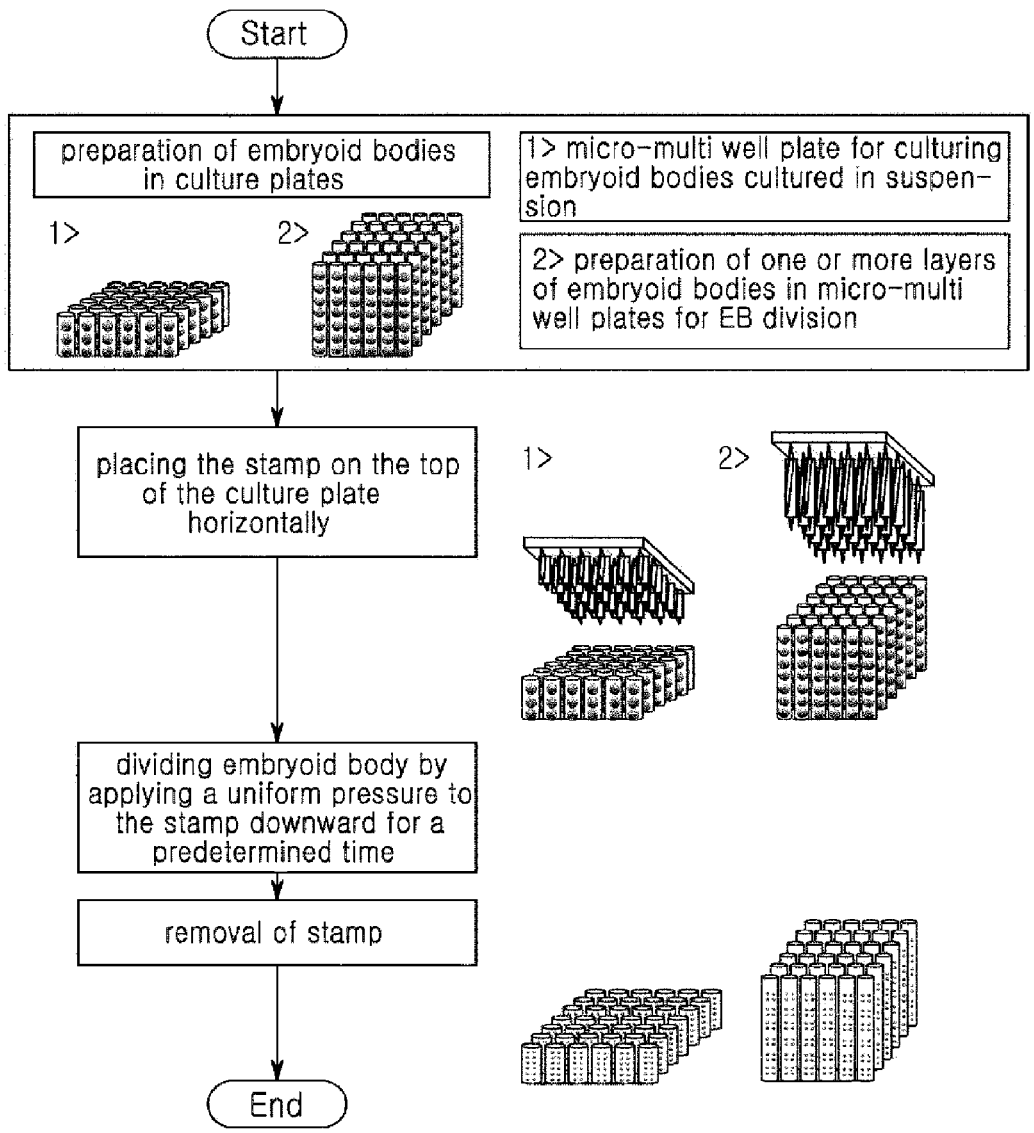

schematic representation of the embryoid body passaging in a suspension culture system (a);

morphologies of the embryoid bodies cultured by the conventional continuous culturing method and by the subculturing method (b);

formation of embryoid bodies from a regular-sized hESC clump using a tissue chopper, in which (Top) shows phase contrast images of hESC and hiPSC colonies, (Top middle) shows hESC and iPSC colonies sliced into a size of 600 μm, visualized with DAPI, (Bottom middle) shows 600 μm clumps formed, and (Bottom) shows embryoid body populations cultured for 7 days, size bar=500 μm (c);

representative images of embryoid bodies derived from hESCs and hiPSCs, mechanically divided at ratios of 1:2, 1:4, and 1:6, size bar=500 μm (d);

FIG. 2 presents a growth curve and proliferation data of embryoid bodies generated by the conventional method and by the subculturing method, showing the size of embryoid bodies generated during 5-week continuous culture (a), the size of embryoid bodies generated by subculturing at ratios of 1:2, 1:4, and 1:6 (b), the size of embryoid bodies generated by periodic division during 15 passages, and the results represent the mean values (±S.E.) of samples obtained from a representative experiment performed in triplicate (c);

proliferation of embryoid bodies, in which Left panel shows representative images and quantification of BrdU+ cells, wherein the relative number of BrdU+ cells per field of vision was quantified, the results are presented as the percentage of the total number of cells counted, and the data represents the mean±S.E. (n=3) (*$p<0.01$, t-test, bar=100 μm), and Right panel shows the result of Western blot analysis of phosphorylated Akt proteins (d);

FIG. 3 shows apoptosis and cell cycle analysis, which is represented by scatter plots of annexin V/PI flow cytometry of embryoid bodies generated by the conventional method (1w-EBs, 2w-EBs, 3w-EBs, 4w-EBs, and 5w-EBs (a)) and by the subculturing method (p1-EBs, p2-EBs, p3-EBs, p4-EBs, and p5-EBs (b)), and four populations were found: viable cells (annexin V and PI-negative); early apoptotic cells (annexin V-positive, PI-negative); late apoptotic cells (annexin V and PI-positive); and necrotic cells (PI-positive);

graph of flow cytometry, in which the values represent mean±S.E. (c);

Western blot analysis of cleaved caspase-3 in embryoid bodies (d);

protein oxidation analysis, in which Top: Representative image for the OxyBlot assay for detecting the level of proteins with oxidative modifications, Bottom: Protein quantification, wherein the blots were scanned, and the bands were quantified by densitometry, the data representing the mean±S.E. (n=3) (**$p<0.01$, *$p<0.05$, t-test) (d);

cell cycle analysis of embryoid bodies, in which Top: FACS analysis of the cell cycle profile of embryoid body, measured by PI staining method, the percentages of cells in G1, S, and G2/M are depicted in the graph, Bottom: graph representing the means±S.E. comparisons of 1-week EBs to 5-week EBs, and 1-week EBs to passage 5 EBs are shown. The data represent the mean±S.E. (n=3) (**$p<0.01$, *$p<0.05$, t-test) (f);

FIG. 4 shows spontaneous in vitro differentiation of embryoid body;

RT-PCR analysis of various differentiation markers of three germ layers (ectoderm (GFAP, NCAM and PAX6), mesoderm (Tbx20, Col1, Col2A1 and cTnT) and endoderm (Amylase)) (a);

immunocytochemical analysis of AFP (α-fetoprotein, endoderm), Sox17 (endoderm), α-SMA (α-smooth muscle actin, mesoderm), desmin (mesoderm), Tuj1 (ectoderm), and Nestin (ectoderm), in which embryoid bodies were plated in gelatin-coated tissue culture plates, and cultured for 10 days, and the nuclei were stained with DAPI (blue) (b);

FIG. 5 shows direct in vitro differentiation of long-term subcultured embryoid bodies into neural stem cells, osteoblasts and cardiomyocytes;

differentiation of neural stem cells (NSC), neuroectodermal spheres (NESs), in which Left panel: NSC marker gene measured by RT-PCR, Right panel: visualization of neuron marker (Tuj1), oligodendrocyte marker (O4), and astrocyte marker (GFAP) expressions after attachment of human embryoid body-derived NESs to culture plates, size bar=500 µm (a);

differentiation of osteoblasts, in which Left panel: mRNA level of osteoblast marker gene measured by RT-PCR, Right panel: mineralized bone nodule-specific Alizarin red S staining and immunocytochemical analysis of osteocalcin, the nuclei were visualized by DAPI staining, and the size bar=500 µm (b);

differentiation of cardiomyocytes, in which Left panel: gene expression profile of cardiac-specific marker by RT-PCR, Right panel: immunocytochemical analysis for MHC, cTnT, and Nkx2.5 in adherent embryoid bodies at day 10, the nuclei were visualized by DAPI staining, and size bar=500 µm (c);

FIG. 6 shows gene expression profile of embryoid body;

heat map analysis and hierarchical clustering analysis of general gene expression in 1w-EB, 2w-EB, 5w-EB, p1-EB, p5-EB and p15-EB, in which Pearson correlation was calculated, average linkage hierarchical clustering was performed, and the distance calculated by GeneSpring GX7.3.1 for comparisons between different embryoid body samples is indicated above the tree lines, and color-coded gene expression is indicated by the log 2-scale color bar (a);

heat map analysis of expression difference between hESC markers and differentiation markers, in which the ratios are color-coded, as indicated by the color index bar (b) and (c);

FIG. 7 shows a growth profile of embryoid bodies (bar S.E. (n=3);

growth curve of 1w-EBs by counting the average number of cells per embryoid body (a);

growth curve of 5w-EBs for 1 to 7 days (b);

growth curve of embryoid body passaged at ratios of 1:2 and 1:4 for 1 to 9 days (c);

FIG. 8 shows apoptosis analysis of irregular-sized embryoid bodies generated by treatment of collagenase IV, in which the graph is flow cytometric analysis data of annexin V/PI staining of embryoid bodies (1w-EBs and 5w-EBs) generated by the conventional collagenase treatment, and the values on the graph represent the mean±S.E.;

FIG. 9 shows characteristics of human fibroblast-derived iPSCs;

morphology of a representative iPSC colony with high levels of alkaline phosphatase and immunocytochemical analysis for general hESC markers: OCT4 and NANOG, in which the size bar=500 µm (a);

semi-quantitative RT-PCR analysis of pluripotency gene expression in human foreskin fibroblast (hFFs), hESC H9 and iPSC, in which transgene-specific PCR primers permit determination of the relative expression levels between total, endogenous (Endo) and retrovirally expressed (Transgene) genes (OCT4, SOX2, cMYC and KLF4) via semi-quantitative PCR, GAPDH is shown as a positive amplification and loading control (b);

bisulfite sequencing used to measure the DNA methylation status in the promoter region of the OCT4 and NANOG genes in hESC H9, iPSC, and hFF, in which genomic DNA was treated by bisulfite conversion, and the promoter regions of OCT4 and NANOG were amplified using specific primer sets, and the methylation status was analyzed, each horizontal row of circles represents an individual sequencing result from one amplicon, open and black circles indicate demethylated and methylated CpGs, respectively, and the proportion (%) of methylated CpGs is indicated (c);

FIG. 10 shows perspective views of a manual EBD (MEBD) (E) according to the embodiments of the present invention, in which the EBD consists of an EBD head (A, B) or an EBD head (C, D) fabricated by attaching a micropatterning part for cutting with or without a wall to a cylindrical body (A, C) and a hexahedral body (B, D), and a handle attached to the EBD head;

FIG. 11 shows perspective views of the micropatterning parts having various structures and shapes (straight type (-), cross type (×), etc.), which can be attached to the body according to the embodiments of the present invention;

FIG. 12 shows a perspective view of an EBD head fabricated by attaching a micropatterning part to a single cylindrical (A)-type or hexahedral (B)-type body for division of one embryoid body, a perspective view of an EB-fitted cylindrical (C)-type or hexahedral (D)-type vessel for culture and division of embryoid body, and a perspective view (F-H) of a pre-treated vessel for culture or division (E-H) having a groove in a matrix for stable adhesion of embryoid bodies;

FIG. 13 shows a perspective view of an integrated (C, D) or detachable (A, B) EBD, fabricated to have one EBD head and multiple micropatterning parts for division of a plurality of embryoid bodies at a time, in which the integrated and detachable EBDs can be used to effectively divide the embryoid bodies adhered to the division vessel (E) without a wall, and the detachable EBD can be used to effectively divide the embryoid bodies prepared in the multi-well plate (F to H) with a wall;

perspective view of a 384-well plate for embryoid body, FIG. 13H shows a perspective view of a 1536-well plate for embryoid body, FIG. 13I shows a perspective view of a manual EBD that is fabricated by attaching a handle to the integrated or detachable EBD head (g);

FIG. 14 shows perspective views for illustrating the division of embryoid bodies prepared in division vessels without a groove (B) and with a groove (C) using the integrated EBD (A), and for illustrating the division of embryoid bodies prepared in division vessels without a groove (E) and with a groove (F) using the detachable EBD (D);

FIG. 15 shows a perspective view of a multichannel pipette for EB that can be effectively used in the multi-well plate for EB;

FIG. 16 is a flow chart for illustrating a procedure of dividing embryoid bodies using MEBD according to the embodiments of the present invention;

FIG. 17 shows a perspective view of MEBD (A) for dividing a multilayer of embryoid bodies (B, C) layered or stacked in the multi-well plate according to the embodiments of the present invention at the same time;

FIG. 18 is a flow chart for illustrating a procedure of dividing embryoid bodies using MEBD capable of dividing a multilayer of embryoid bodies at a time according to the embodiments of the present invention; and FIG. 19 shows a perspective view of AEBD (A and B) according to the embodiments of the present invention, in which various types (circular, triangle, square, hexagon) of the micropatterning part for cutting, such as feather blades, one or multiple of straight or cross type (C and D), can be attached to part A, the micropatterning part can be fabricated in various combinations of size and shape, and one or more EBD heads can be mounted in the cutting head according to the size and shape of the division vessel, or the intended purpose.

DETAILED DESCRIPTION OF THE PREFERRED EMBODIMENTS

In one aspect to achieve the above objects, the present invention relates to a method for large-scale propagation of embryoid bodies, comprising the step of subculturing embryoid bodies that are generated from stem cells.

As used herein, the term "stem cells" refer to cells possessing pluripotency to differentiate into endoderm-, mesoderm- and ectoderm-derived animal cells, or cells possessing multipotency to differentiate into the cells that are closely related in terms of tissue type or function. The stem cells used for the objects of the present invention are not limited, but preferably pluripotent stem cells, and more preferably embryonic stem cells or induced pluripotent stem cells (dedifferentiated cells).

As used herein, the term "animal" means livestock such as cattle, pigs, sheep, horses, dogs, mice, rats and cat, as well as humans and primates. Stem cells derived from human are preferred.

As used herein, the term "embryonic stem cells (ESC)" refers to pluripotent cells capable of differentiating into any type of animal cells, derived from the inner cell mass of blastocysts at a stage before it would implant in the uterine wall, and human embryonic stem cells derived from human are preferred.

Figure 9B:
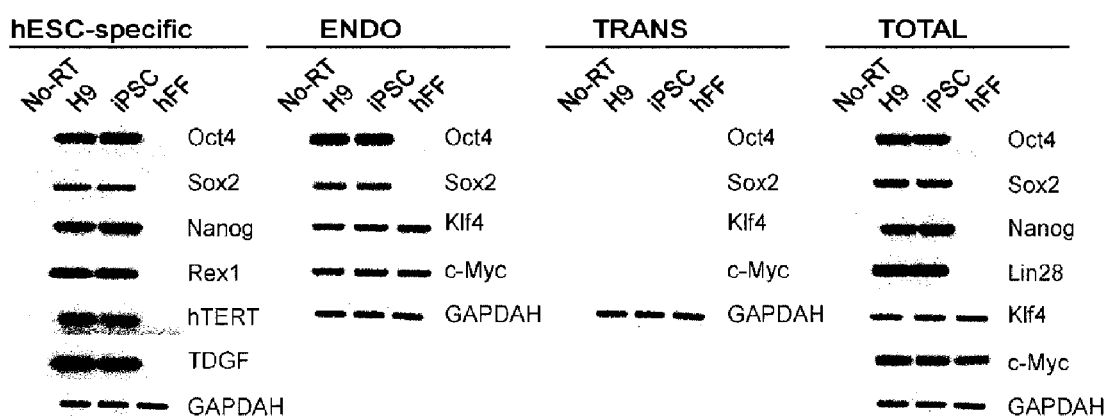

As used herein, the term "induced pluripotent stem cells (iPSC, dedifferentiated cells)" means stem cells having differentiation ability similar to that of ESC, in which undifferentiated stem cells having a differentiation potential similar to that of embryonic stem cells are established from animal somatic cells using a dedifferentiation technique. The somatic cells for iPSC establishment may be derived from various animals, and human induced pluripotent stem cells (hiPSC) that are prepared from human somatic cells by using a dedifferentiation technique may be preferably used. In addition, ESC or iPSC may be easily established by those skilled in the art by the known methods. According to one preferred embodiment of the present invention, the present inventors prepared iPSC by inserting a dedifferentiation gene into human foreskin fibroblast, and analyzed their characteristics (FIGS. 9a to 9c).

As used herein, the term "embryoid body" refers to spheroid colonies produced by the growth of stem cells in suspension culture. The embryoid body has the potential to differentiate into endodermal, ectodermal, and mesodermal lineages, thereby being used as a precursor in most differentiation induction process for obtaining tissue-specific differentiated cells. The present invention contributes to development of the technologies to obtain highly valuable stem cell-derived differentiated cells by effectively improving propagation of embryoid body itself.

As used herein, the term "propagation" means an increase in the number of cells. According to one preferred embodiment, it was found that growth and proliferation of embryoid bodies can be effectively improved by dividing embryoid bodies in the same size or ratio and subculturing them.

As used herein, the term "subculture" means that a portion of cells is periodically passaged by transferring them to a new culture vessel and by replacing the culture medium with a fresh culture for the long-term culture of healthy cells. As the number of cells increases in the limited space of the culture vessel, the cells die due to nutrient depletion or waste accumulation in a predetermined time. Thus, subculture is used to increase the number of healthy cells. Typically, 1 passage means culture by one replacement of medium (culture vessel) or one dividing of cell population. In the conventional culture methods, embryoid bodies are cultured by continuous culture without passaging until their use. The subculture methods known in the art may be used without limitation, but a mechanical or enzymatic division method may be preferably performed.

As used herein, the term "mechanical division" means that cell aggregates are divided physically or mechanically. The method known in the art may be used without limitation, but cells may be preferably divided by using a blade, a tissue chopper, a needle, pipetting, EBD (embryoid body divider) or a scrapper. According to one preferred embodiment of the present invention, it was found that large-scale propagation of embryoid bodies can be achieved by subculturing them using a blade or a tissue chopper.

In the present invention, the cell division method using an EBD may include the steps of (a) preparing an embryoid body in a coated culture vessel; (b) placing the EBD on the top of the culture vessel horizontally; (c) applying a uniform pressure to the culture vessel using the EBD to divide the embryoid body; and (d) removing the EBD. The divided embryoid bodies may be continuously cultured in a mixture using a single vessel or cultured separately using a multi-well plate for EB.

The EB division method using the EBD is, as shown in FIG. 17, performed to divide a multilayer of embryoid bodies in the multi-well plate for EB at a time. This division method may be achieved by varying the height of the micropatterning part and multi-well plate.

Specifically, the division method using EBD of the present invention may include the steps of (a) preparing an embryoid body in a multi-well plate for EB; (b) placing the EBD on the top of the multi-well plate horizontally; (c) applying a uniform pressure to the multi-well plate using the EBD to divide the embryoid body; and (d) removing the EBD. At this time, it is possible to efficiently divide a large amount of embryoid bodies in a short time by preparing at least one layer of embryoid bodies in the multi-well plate for EB in step (a) (FIGS. 17 and 18).

As used herein, the term "embryoid body divider (EBD)" means a device used for efficient division of embryoid bodies, which is required for the effective subculture of embryoid bodies. The EBD is characterized by including an EBD head composed of a body that has a top (having no cutting edge) and a bottom (having a cutting edge); and a micropatterning part that functions to cut and divide embryoid bodies. The division method of embryoid bodies can be provided by means of the EBD. In one embodiment of the present invention, constitution of the EBD for EB division was described in detail.

The body may have any of polygonal patterns according to the shape of the culture vessel where embryoid bodies are cultured. It is preferable that the body has any of square, pentagonal, hexagonal and circular shapes (FIG. 10).

The EBD head may be fabricated to have a variety of sizes corresponding to the size of the vessel. All of integrated and detachable EBDs are fabricated to have a size being 0.1 μm smaller than that of each vessel/well, which ensures the easy mounting and detaching of the EBD in/from the vessel. When an EB patterning vessel is used, the detachable EBD fabricated to have a separate cutting edge in each well can be used. The cutting edge can be fabricated to have a cutting line being 0.1 μm smaller than the grid of each well, and to have a cutting height being 0.1 μm larger than the height of the culture vessel for EB in both integrated and detachable EBDs.

The body may be made of any material of stainless-steel, carbon steel, polydimethylsiloxane (PDMS), polymethylmethacrylate (PMMA), polyacrylates, polycarbonates, polycyclic olefins, polyimides, polyurethans, and polyester, but is not limited thereto.

The micropatterning part may be made of any material of polydimethylsiloxane (PDMS), polymethylmethacrylate (PMMA), polyacrylates, polycarbonates, polycyclic olefins, polyimides, polyurethans, and polyester, but is not limited thereto.

The micropatterning part for cutting may be made of stainless-steel or carbon steel, and the body is attached with one or more cutters having various patterns capable of cutting embryoid bodies, thereby fabricating the EBD head (FIGS. 10 and 13).

Each micropattern and each edge of the micropatterning part for cutting may be fabricated to have various shapes (circular, triangle, square, hexagon) including a straight type (–) or a cross type (+).

In the present invention, embryoid bodies grown to be in a suitable state and size can be divided to have a uniform size and shape by means of EBD. In particular, the shape of divided embryoid bodies can be effectively modified to various patterns by altering the shape of the micropatterning part constituting EBD. In addition, the conventional cell culture vessels can be used in the EBD system of the present invention, but EB vessels optimized for the EBD system may be developed (FIGS. 12C to 12H and FIG. 13F). EB vessels may be designed to have various shapes and sizes according to the purpose, and the EBD body and the micropatterning part for cutting can be also fabricated to have various polygonal shapes including a circular or square shape, corresponding to the EB vessels (FIG. 11 and FIGS. 13A to 13D).

During a subculturing when a large amount of embryoid bodies are cultured in a single vessel, each of the embryoid bodies is transferred to a single division vessel (top of 1,000-8,000 μm width, bottom of 100-8,000 μm width, depth of 2,000-20,000 μm) (FIGS. 13C and 13D) or a multi-well plate (top of 1000-8000 μm width, bottom of 100-8000 μm width, depth of 2,000-20,000 μm; 96-, 384-, 1536-well plate) (FIG. 13F) for division of embryoid bodies, and then EBD fabricated to be fitted for each vessel (FIGS. 12A and 12B, FIGS. 13A to 13D) is used to effectively divide the embryoid bodies (FIGS. 14 and 16). On the other hand, the multi-well plate for EB culture can be effectively used for culturing a single layer of embryoid bodies, and it is also possible to divide a large amount of embryoid bodies at a time by aligning multilayer of embryoid bodies in the vessel for division (FIGS. 17B and 17C and FIG. 18). The vessel developed for culture and division of embryoid bodies may have a variation in its height (depth of 50-20,000 μm) (FIGS. 17B and 17C).

In the present invention, the vessel for culturing or division of embryoid bodies may have various bottom shapes of flat (FIG. 12E), round (FIG. 12F), square (FIG. 12G), or V-shape (FIG. 12H), and this configuration can be also effectively applied to the multi-well plate.

If it is necessary to attach and fix embryoid bodies without using the multi-well system, the surface of the culture vessel to which embryoid bodies are fixed can be selectively coated with polylysine, collagen, gelatin, laminin, cell matrix component, nanopolymer or the like, thereby inducing adherent culture of embryoid bodies at a particular position (FIGS. 12E to 12H; #17).

The bottom matrix of the culture vessel coated to attach embryoid bodies (FIGS. 12E to 12H; #17) may have a groove for easy and stable adhesion of embryoid bodies, and the groove may have any of the polygonal shapes of flat (FIG. 12E), round (FIG. 12F; #18), square (FIG. 12G; #18), or V-shape (FIG. 12H; #18) (FIGS. 14C and 14F).

As shown in FIGS. 12E to 12H, the groove in the bottom of the culture vessel may be fabricated to have a size smaller than that of each single vessel with a diameter of 100 μm or more, or smaller than each well having a different size so as to fit each embryoid body into the groove (FIGS. 12E to 12H; #20), and the groove may be fabricated to have a height smaller than the diameter of fully grown embryoid body, that is, within a range of 50-500 μm (FIGS. 12E to 12H; #19).

As shown in FIG. 13C, the EBD of the present invention can effectively utilize a vessel (culture container, plate, etc.) having one or more repeated grids (circular, square, hexagonal), and characterized in that the vessel is fabricated to include a matrix part (FIGS. 12E to 12H; #17) (flat with no groove, U-shaped, V-shaped, square-shaped groove; (FIGS. 12F to 12H; #18)) that is coated with an adhesion-inducing substance (polyethylene glycol (PEG), PDMS, matrigel, fibronectin, etc.) for selective adhesion of embryoid bodies in the center of each grid, and the matrix part provides a support for effective division of embryoid bodies.

The grid (FIG. 13E; #21) may be a grid of 100-10,000 μm on all sides, a circular grid having a diameter of 100-10,000 μm, or the like, and the depth of the culture vessel may be 2,000-20,000 μm (FIG. 13C; #16-3).

In the present invention, a large amount of embryoid bodies may be cultured in a general/conventional culture vessel by suspension culture at a time. To improve this method, alternatively, each single embryoid body may be separately cultured in a culture vessel including a well having a top of a diameter of 1000-8000 μm (FIGS. 12C to 12H; #16-1), a bottom of a diameter of 100-8000 μm (FIGS. 12C to 12H; #16-2), and a depth of 2,000-20,000 μm (FIGS. 12C to 12H; #16-3), when calculated on the basis of the diameter (approximately 300-500 μm) of the embryoid bodies (7-14 days) (FIGS. 1c and 2a) continuously cultured in an optimal growth state (FIGS. 12C to 12H and FIG. 13F). In this regard, a single culture vessel or a multi-well plate having various shapes and sizes may be used, considering the size of the embryoid body to be produced, and a 96-, 384- or 1536-well plate may be preferably used (FIG. 13F). The embryoid bodies cultured under the above conditions can be effectively divided by using the EBD fabricated to be fitted for the size of division vessel (FIGS. 12A, 12B, 13A to 13D, 14, 16 and 18).

According to the embodiments of the present invention, EBD is characterized in that formation, culture, and division steps of embryoid bodies are allowed in a single system by using a vessel capable of culturing/dividing a single embryoid body, or a multi-well plate capable of separately culturing/dividing two or more embryoid bodies. In another embodiment, EBD is also characterized in that a mixture of one or more embryoid bodies is cultured and then adhesion-cultured in a predetermined position of the vessel having a grid or pattern, followed by division of embryoid bodies, or embryoid bodies are transferred in the multi-well plate for EB culture/division, followed by division.

When a large amount of embryoid bodies are transferred in the multi-well plate, a multichannel pipette tip and a multichannel pipette fabricated considering the size of each embryoid body may be efficiently used (FIG. 15).

In the present invention, EBD used for division of embryoid bodies may be a manual EBD (MEBD) or an automatic EBD (AEBD). In the manual EBD, a handle is attached to the EBD head (FIG. 10E and FIG. 13I) to manually divide embryoid bodies. In the automatic EBD, the EBD head is provided in an automatic electric-powered device to mechanically divide embryoid bodies by an electric power system (FIG. 19).

The automatic electric-powered EBD is characterized by including a lower plate, on which EB culture vessel or EB division vessel is fixed; a lateral plate which is provided to protrude upward from one end of the lower plate; an upper plate which is connected to the top end of the lateral plate in parallel with the lower plate; a cylinder guide, of which one end is fixed on the lower surface of the upper plate, and which is provided to protrude toward the lower plate; and a cylinder or a device, which is provided to be movable in a vertical direction through the cylinder guide and has EBD fixed on its lower surface to apply a predetermined pressure to embryoid bodies in the EB culture vessel or in EB division vessel (FIG. 19). As shown in FIG. 19, it is possible to design the EBD head and the micropatterning part in various sizes, shapes, and combinations, considering the size and shape of the division vessel and the size and shape of embryoid body to be produced. In addition, various types of the micropatterning part may be provided in the EBD head according to the size and shape of the division vessel or the intended purpose, thereby constituting integrated and detachable EBDs.

As used herein, the term "enzymatic division" means dissociation of cell aggregates by enzymatic treatment. The methods known in the art may be used without limitation, but cell aggregates may be preferably dissociated by treatment of collagenase including collagenase I, II, III, and IV, accutase, dispase or trypsin, followed by subculturing.

Preferably, the subculturing is carried out by suspension culture.

Preferably, hESCs cultured for 4 to 7 days are cultured in suspension for 3 to 8 days to establish primary embryoid bodies. The embryoid bodies are divided into ½₀ to ½-sized pieces, preferably ½₁₂ to ½-sized pieces, and more preferably ⅛ to ½-sized pieces, and then cultured in suspension for a primary subculture. The divided embryoid bodies are propagated by suspension culture for 4 to 16 days according to their size, until they have a suitable size. Then, the embryoid bodies can be propagated by secondary and tertiary subculture. More preferably, the culture method can be established by dividing the embryoid bodies into ¼-sized pieces, and culturing them in suspension for 8 to 9 days. The primary embryoid bodies can be also acquired suspension culture of colonies of collected stem cells cut into the dimension of 10 to 1000 μm on all sides, preferably 100 to 1000 μm on all sides or by culturing undisturbed hESC or iPSC colonies in suspension. More preferably, the primary embryoid bodies can be acquired by culturing collected stem cells cut into the dimension of 600 μm on all sides in suspension for 7 days. The embryoid bodies produced by the conventional methods showed heterogeneity in the size and shape, and heterogeneous embryoid bodies showed limited differentiation potential and low production yield. Therefore, with respect to the purpose of the present invention for the production of the size-controlled embryoid bodies, the regular-sized embryoid bodies can be uniformly produced by culturing uniform-sized stem cells in suspension. According to one preferred embodiment of the present invention, human embryonic stem cells were collected the dimension of 600 μm on all sides using a tissue chopper or a sterile needle to acquire embryoid bodies.

Figure 2A:
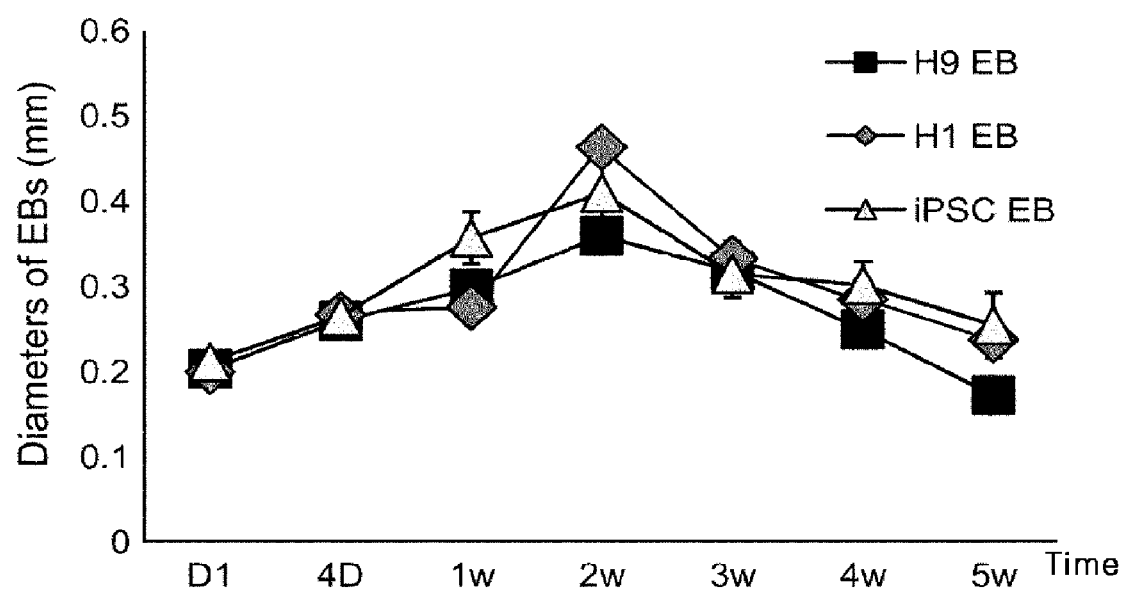
Figure 2B:
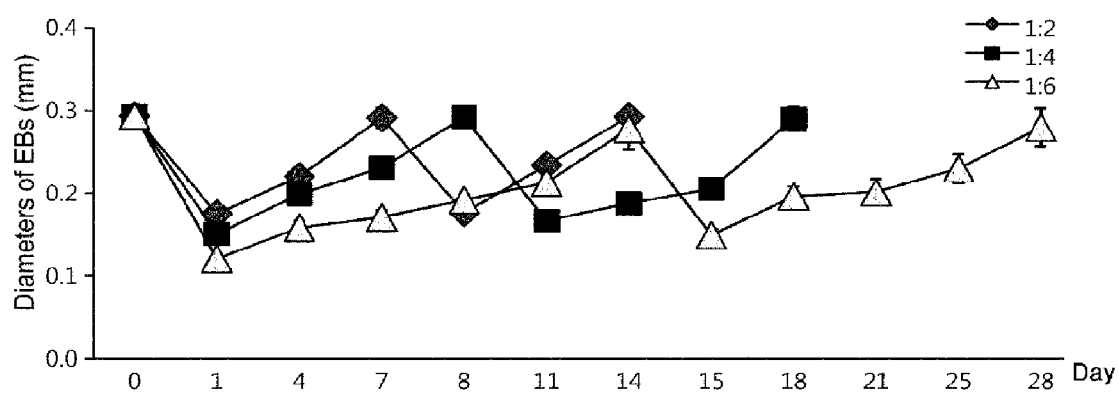
Figure 2C:
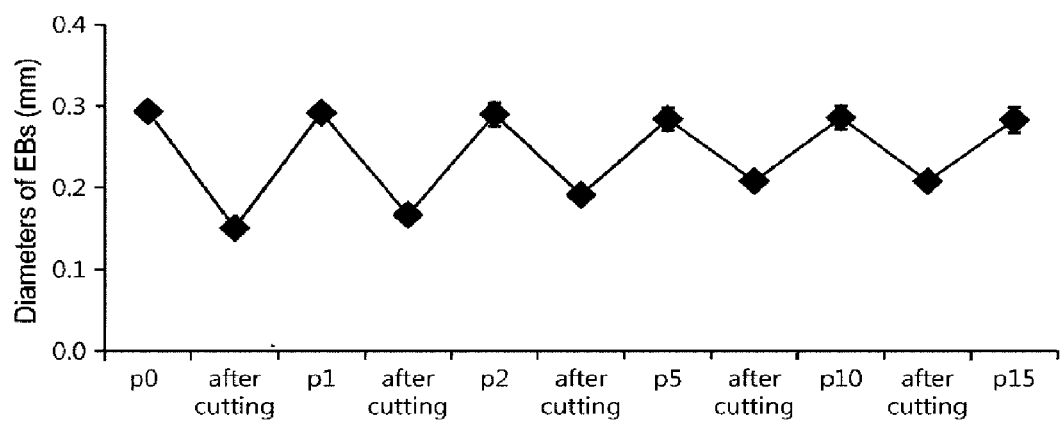

Subculture of the embryoid bodies may be performed without limitation in the number of times as long as they retain the propagation ability and the potential to differentiate into three germ layers, but preferably 1 to 200 times, more preferably 1 to 100 times, much more preferably 1 to 50 times, and most preferably 15 to 20 times. According to one preferred embodiment of the present invention, it was found that long-term-subcultured embryoid bodies (15 passages or more) are able to propagate while they retain the potential of the successful differentiation into three germ layers of endodermal, mesodermal, and ectodermal lineages (FIGS. 4b, 5a to 5c and 6b to 6c) (FIG. 2c).

Figure 1B:
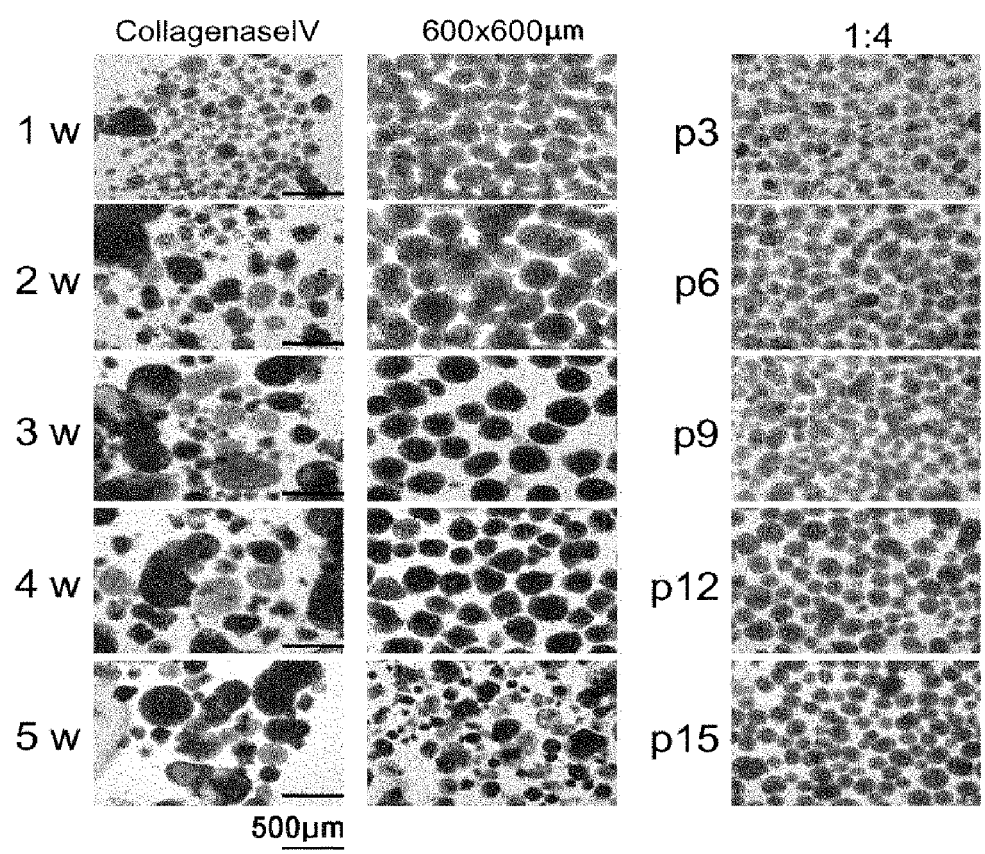
Figure 1C:
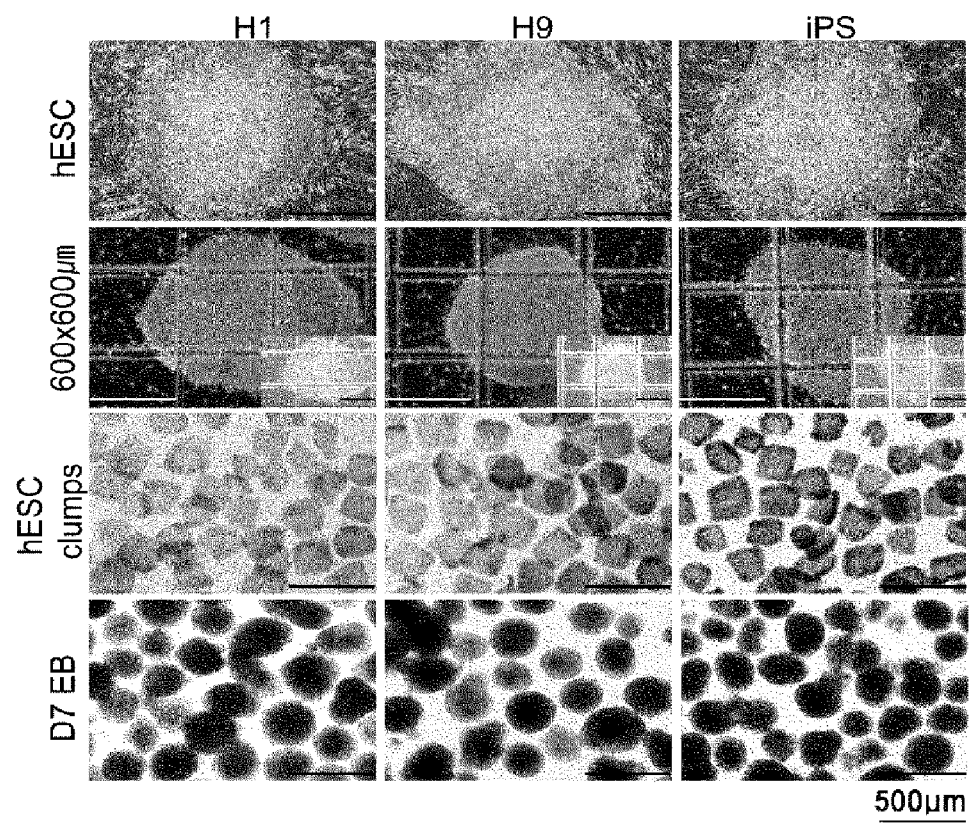
Figure 7A:
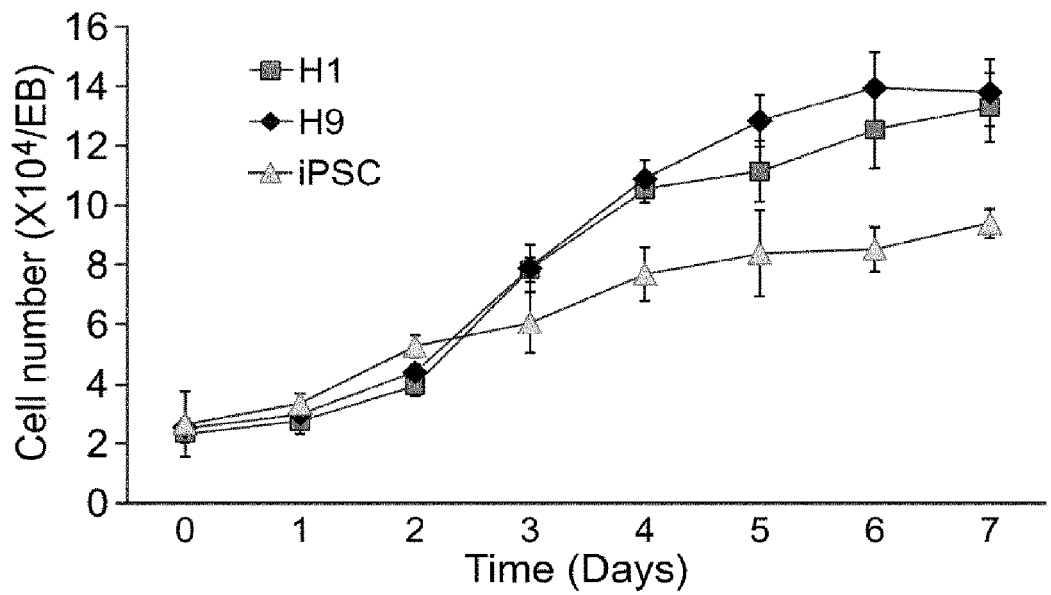
Figure 7B:
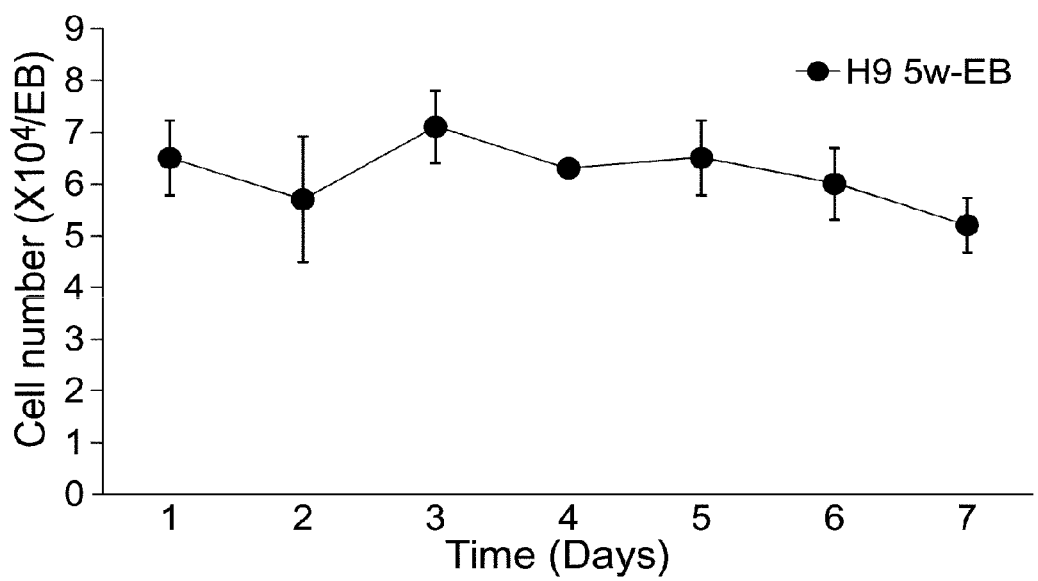
Figure 7C:
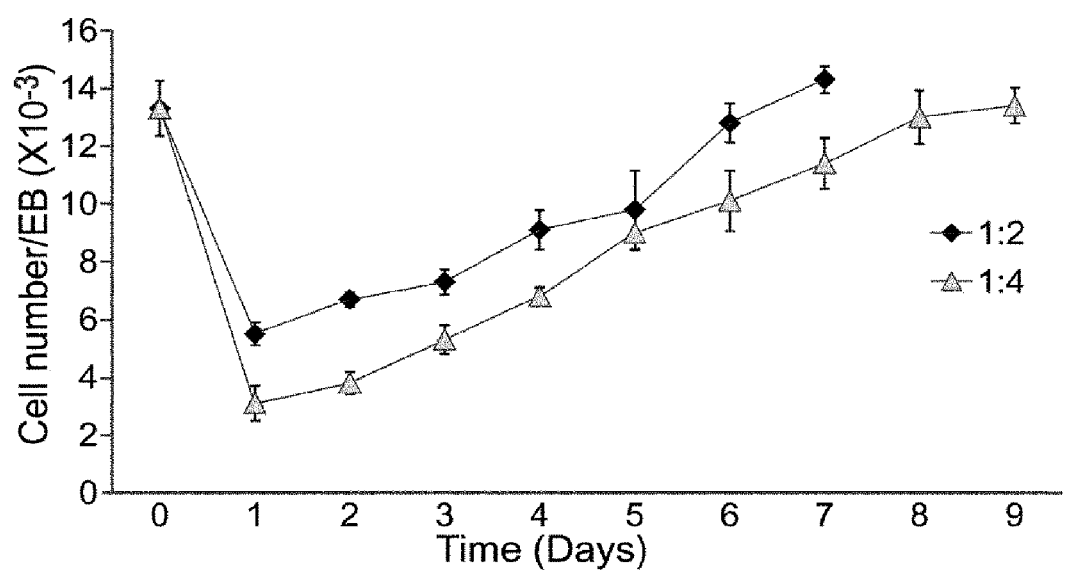

Unlike the conventional method for maintaining embryoid bodies in suspension without passaging, the present inventors have established the method for generating embryoid bodies through passaging, and they performed the following experiment to confirm that the formed embryoid bodies of the present invention have proliferation and differentiation potential. According to one preferred embodiment of the present invention, hESC H1, H9 and hiPSC colonies were collected the dimension of 600 μm on all sides, and dispersed into small clumps by treatment of collagenase IV to acquire uniformly-sized embryoid bodies (FIG. 1c). One week after culturing, the embryoid bodies were passaged at ratios of 1:2, 1:4, and 1:6, and they showed successful re-growth back to volumes at 7, 9, and 14 days, respectively (FIG. 1d), indicating propagation of embryoid bodies by the method of the present invention. In the conventional method of simple continuous culture without passaging, the growth of embryoid bodies reduced after 2 weeks (FIGS. 2a, 7a and 7b). The effects of the passaging of the present invention on the growth of embryoid bodies showed that the further growth of embryoid bodies maintained during the long-term subculture (15 passages; p15) (FIGS. 2b, 2c and 7c). Moreover, their proliferation was analyzed by immunocytochemistry using a cell proliferation marker BrdU and Western blot analysis using phosphorylated Akt which is a key factor in transduction of proliferative signals. As a result, the 5 weeks long culturing showed a significant decrease in BrdU binding (56.7±3.2%), whereas the passaged embryoid bodies (p1-EBs; 80.7±2.2, and p5-EBs; 85.1±5.2%) showed an increase in BrdU binding, similar to that of the control group 1w-EBs (83.2±4.4%) (FIG. 2d). All of the embryoid body samples showed no significant change in the phosphorylated Akt level (FIG. 2d). It was found that the healthy grown embryoid bodies maintained the constant activated Akt level in the limited protein, suggesting that the number of cells constituting the embryoid bodies increases during continuous subculture.

Figure 3A:
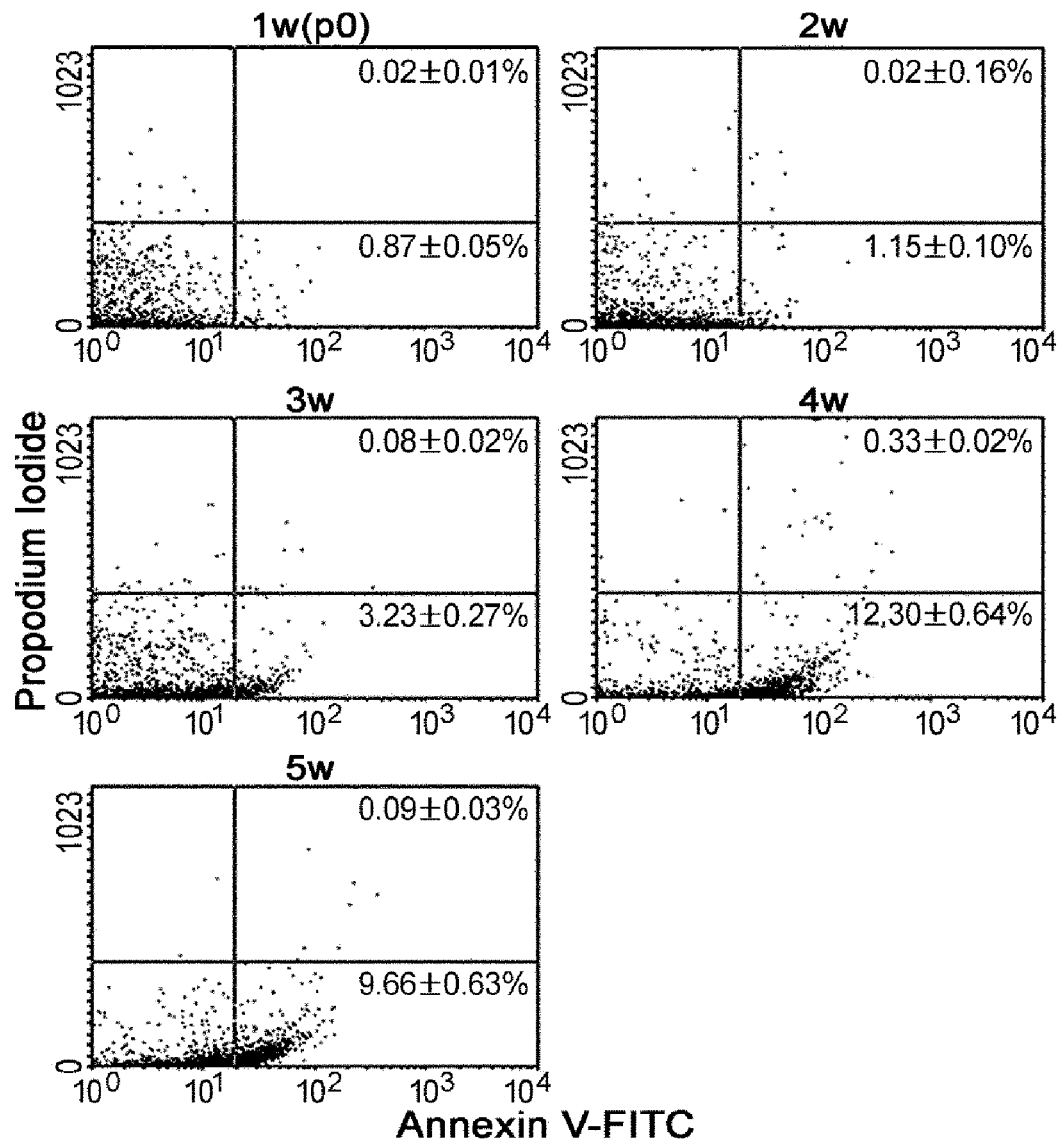
Figure 3B:
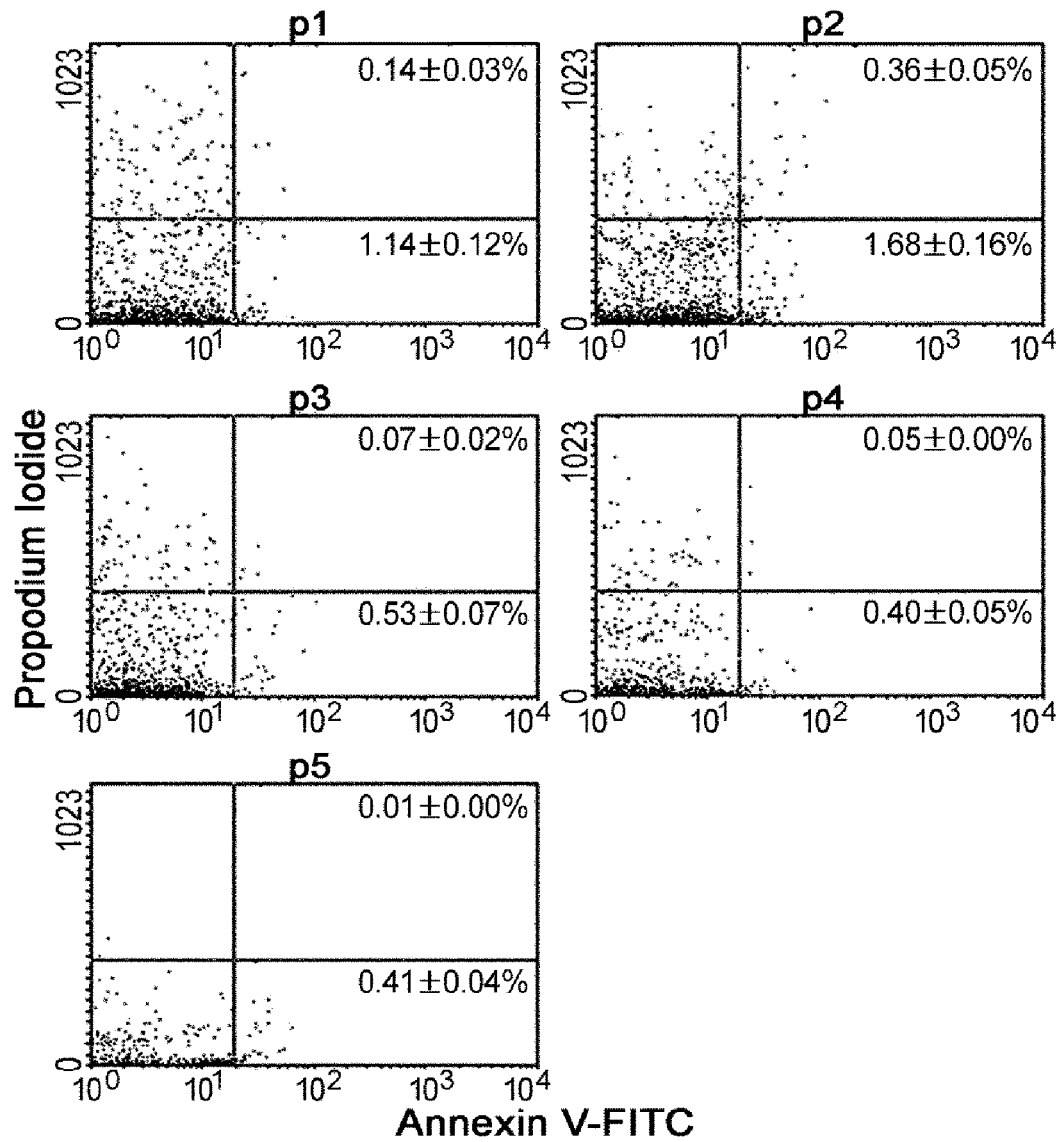
Figure 3C:
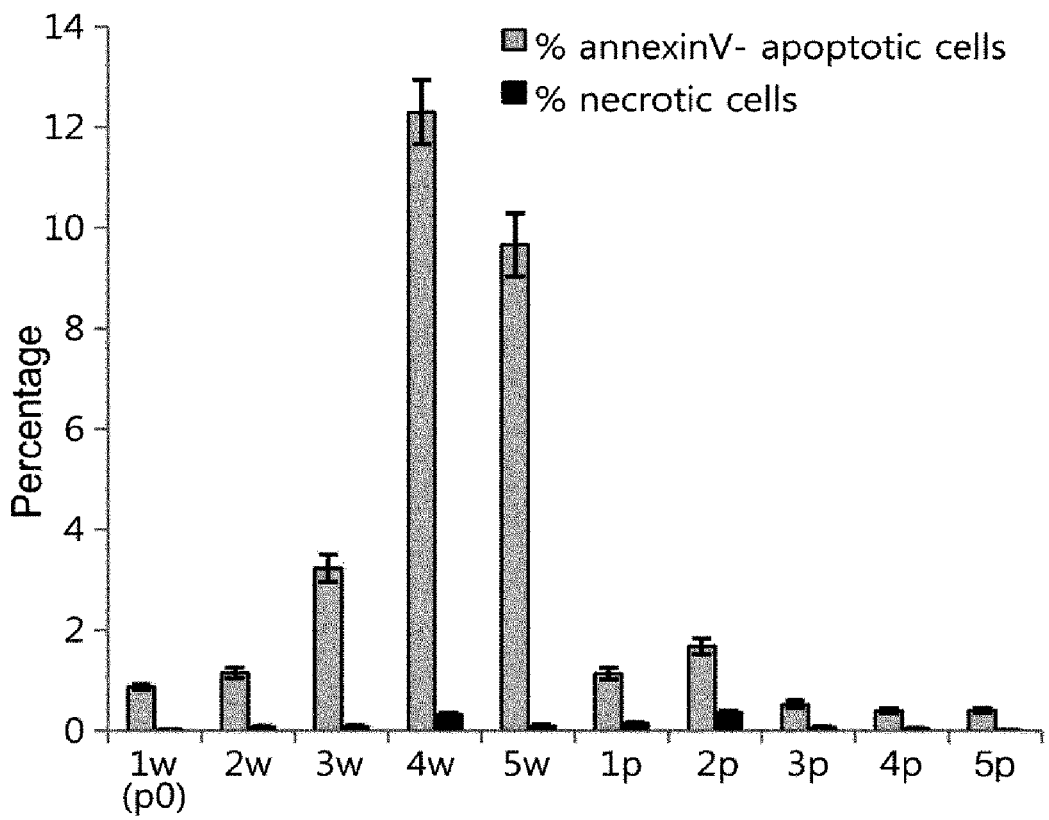
Figure 3D:
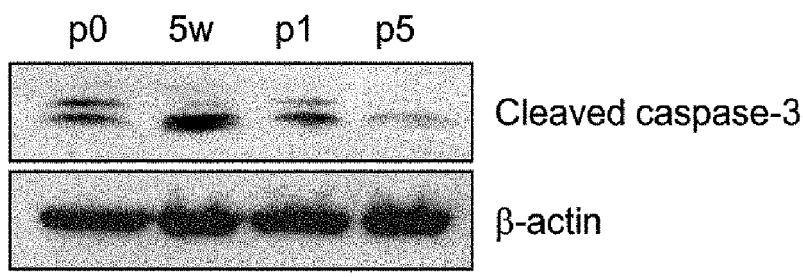
Figure 3E:
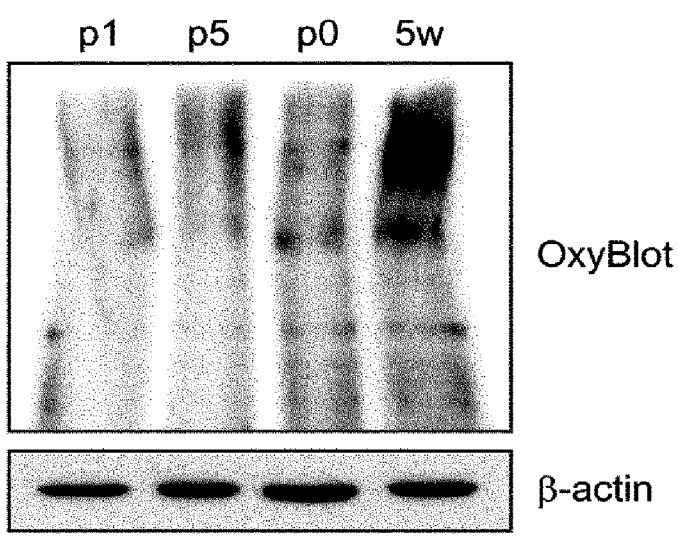

According to one preferred embodiment of the present invention, the effect of the passaging of embryoid bodies on their functions was determined by examining the effect of the passaging of embryoid bodies on apoptosis and cell cycle. The results of annexin-V and PI (propidium iodide) staining of embryoid bodies under continuous culturing and subculture showed that after continuous culture, the number of annexin-V positive apoptotic cells of 4w-EBs and 5w-EBs was 12.30±0.64% and 9.66±0.63%, respectively (FIGS. 3a to 3c), and the long-term continuous culture exhibited an increased level of apoptosis, whereas the embryoid bodies under continuous subculture of the present invention showed less than 2% apoptotic or dead cells, suggesting that apoptosis is prevented by the subculture (FIGS. 3a to 3c). The increased level of apoptosis was also observed in 5w-EBs under continuous culture after treatment of collagenase (FIG. 8). Further, the levels of the cleaved caspase-3 that is generally found in major apoptosis signaling pathways were examined in p1-EBs and p5-EBs, in comparison to the control group 1w-EB. The result showed that the level of the cleaved caspase-3 was increased in 5w-EBs (FIG. 3d), suggesting that apoptosis is prevented by the subculture of embryoid bodies. The oxidative stress is also a leading factor in apoptosis. Thus, to determine whether the apoptosis is mediated by oxidative stress in the embryoid bodies under continuous culture, Oxyblot assay for detecting protein oxidation (carbonylation) was performed. The result showed that the carbonyl signal was significantly increased in 5w-EBs, as compared to 1w-EBs, whereas the carbonyl signal was significantly reduced in p1-EBs and p5-EBs, similar to that in 1w-EBs (FIG. 3e).

The effect of the subculture of embryoid bodies on cell cycle was examined by flow cytometry of embryoid bodies under continuous culture and under subculture. As a result, embryoid bodies under continuous culture showed time-dependent G2/M phase cell accumulation, and as a percentage of G2/M phase cells increased, a percentage of S phase cells decreased, and there was no significant change in a percentage of G0/G1 phase cells (FIG. 3f). In contrast, embryoid bodies under subculture displayed no marked differences in the cell-cycle distribution relative to the control group (FIG. 3f). Overall, the embryoid bodies under continuous culture exhibited G2/M arrest by an increased level of apoptosis and free radical protein damage. It was confirmed that these obstacles are overcome by subculturing of embryoid bodies, and thus cell survival rate is improved by anti-apoptotic signals and cell cycle proceeds continuously.

Figure 4A:
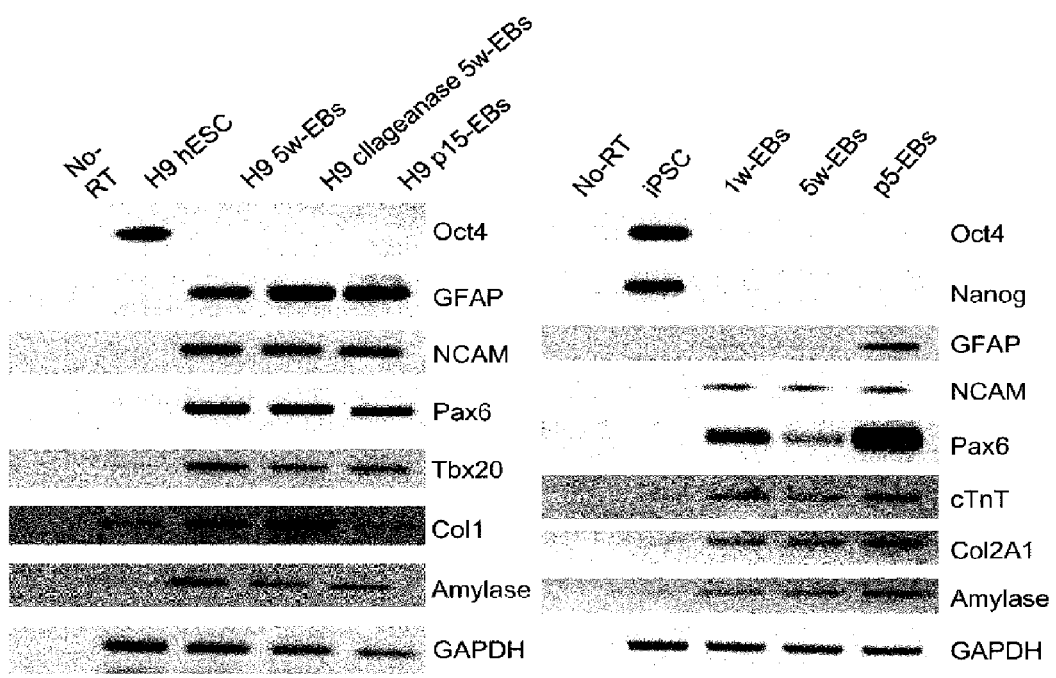
Figure 4B:
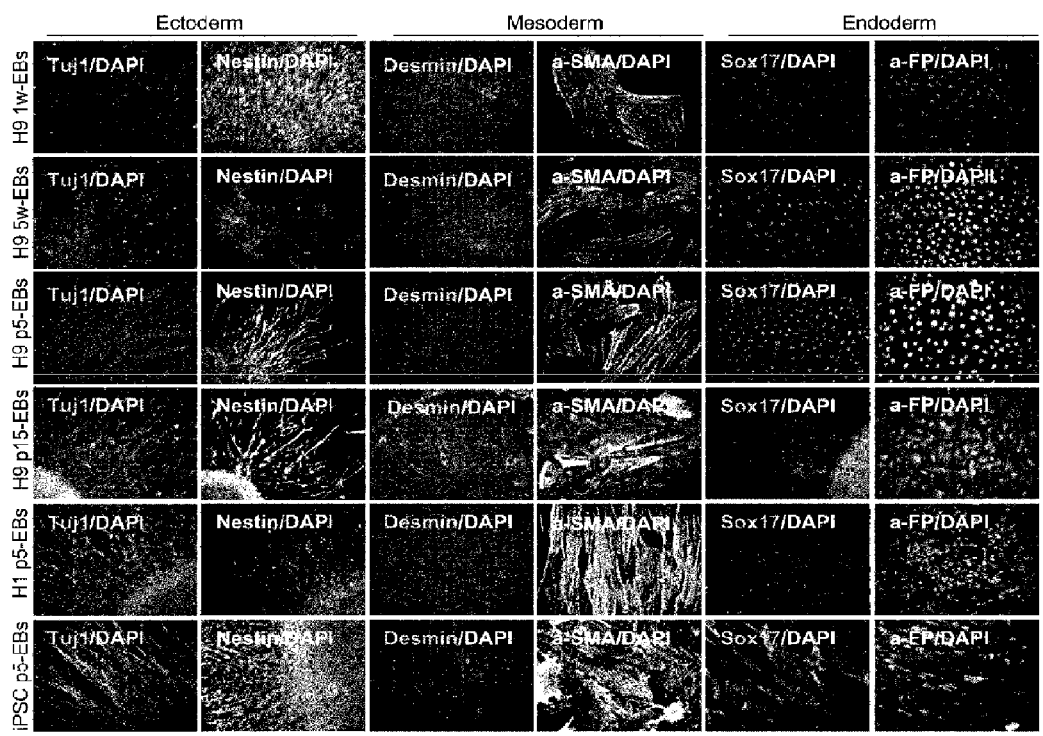
Figure 5A:
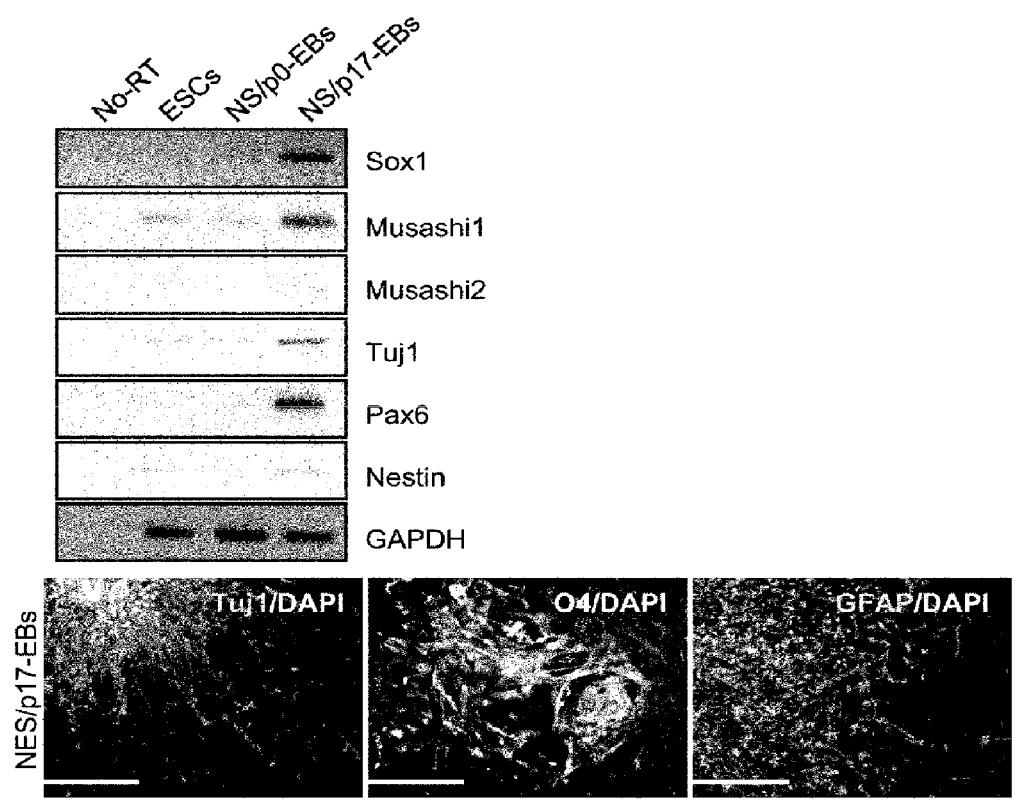
Figure 5B:
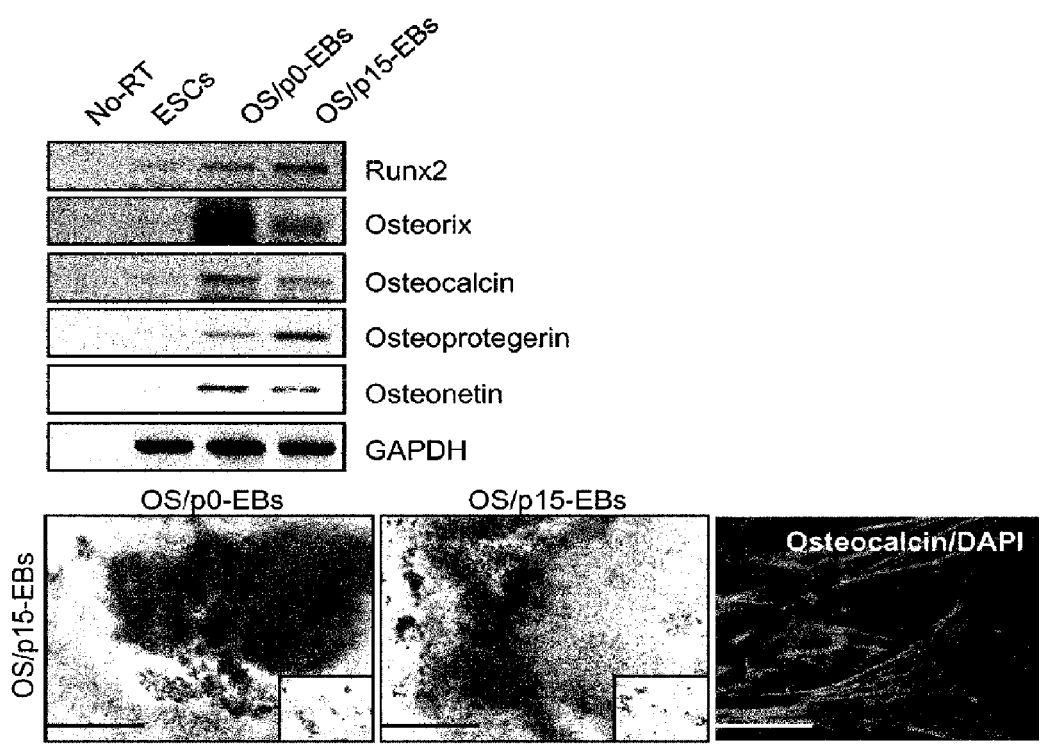
Figure 5C:
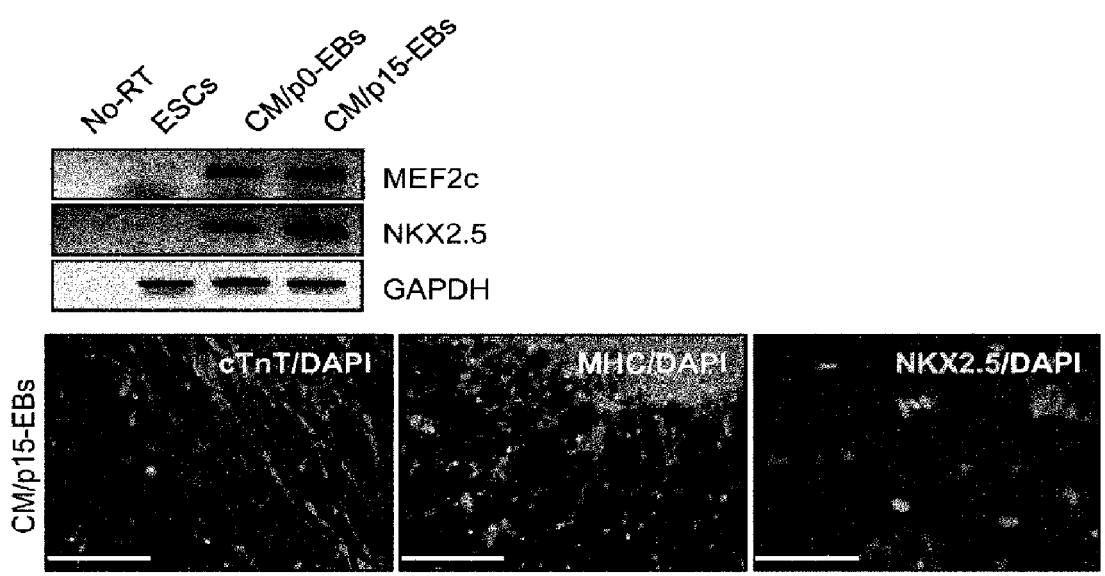

According to one preferred embodiment, to investigate the differentiation potential of the embryoid bodies subcultured by the method of the present invention, the present inventors examined the differentiation capacity of passaged embryoid bodies derived from hESCs H9 and H1, and hIPSC in vitro. The result of RT-PCR showed expressions of the differentiation markers specific for three-germ layers, such as PAX6 (ectoderm), NCAM (ectoderm), GFAP (ectoderm), Tbx20 (mesoderm), COL1 (mesoderm), cTnT (mesoderm), Col2A1 (mesoderm), and Amylase (endoderm) expressed in differentiated cells, in the passaged embryoid bodies derived from hESC H9 and hiPSC. In contrast, OCT4 and NANOG expressions were remarkably reduced (FIG. 4a), and Tuj1 (ectoderm), Nestin (ectoderm), Desmin (mesoderm), α-SMA (α-smooth muscle actin, mesoderm), Sox17 (endoderm), and AFP (α-fetoprotein, endoderm)-positive cells were detected by immunocytochemistry (FIG. 4b), indicating that the subcultured embryoid bodies have a potential to differentiate into three germ layers in vitro. Next, in order to examine whether the subcultured embryoid bodies can be directly used as a starting point of differentiation and can be differentiated by the present differentiation method, the present inventors confirmed the successful differentiation of the long-term subcultured embryoid bodies (>15 passages) into neural stem cells (NSCs. ectoderm), osteoblasts (mesoderm) and cardiomyocytes (mesoderm) by RT-PCR and immunocytochemistry of the markers specific for the above differentiated cell types (FIGS. 5a to 5c). Consequently, it was confirmed that the subcultured embryoid bodies have pluripotency to differentiate into various cell types, and the differentiation occurs in response to the same signals, independent of continuous subculture.

Figure 6A:
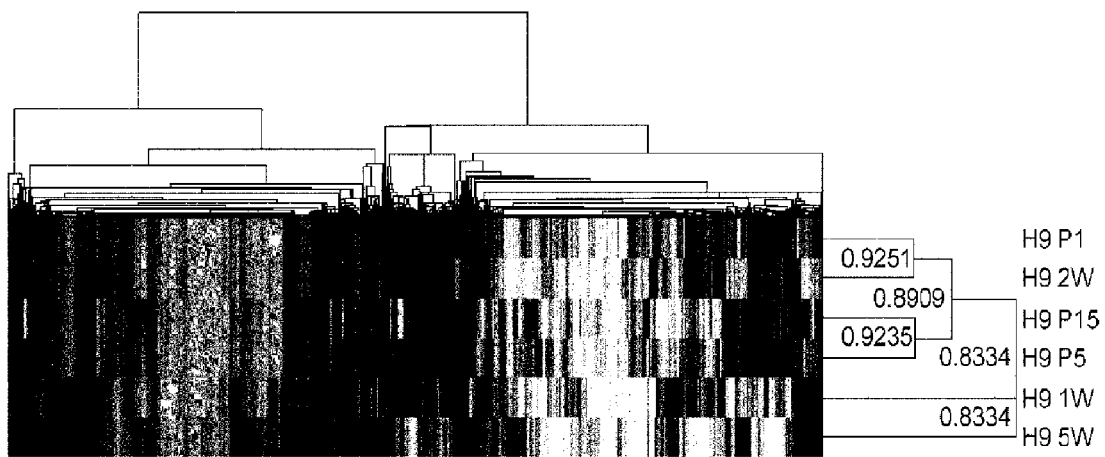
Figure 6B:
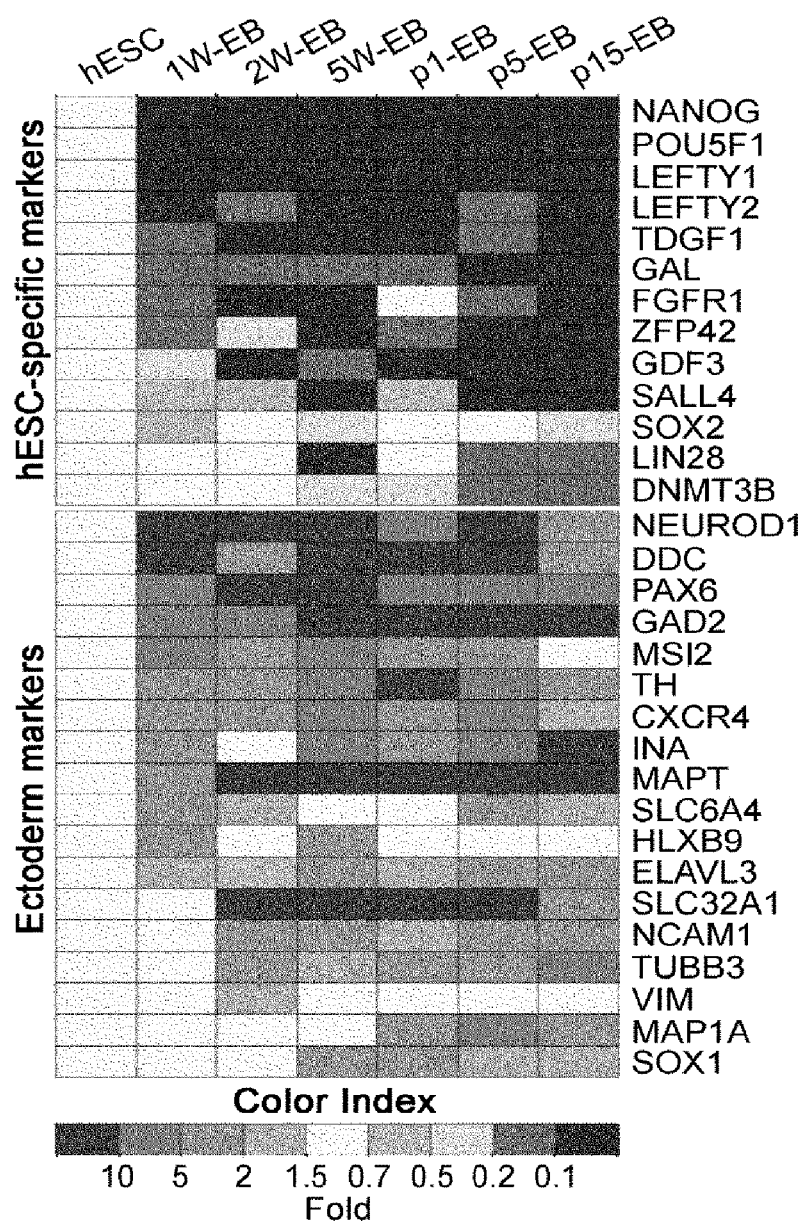
Figure 6C:
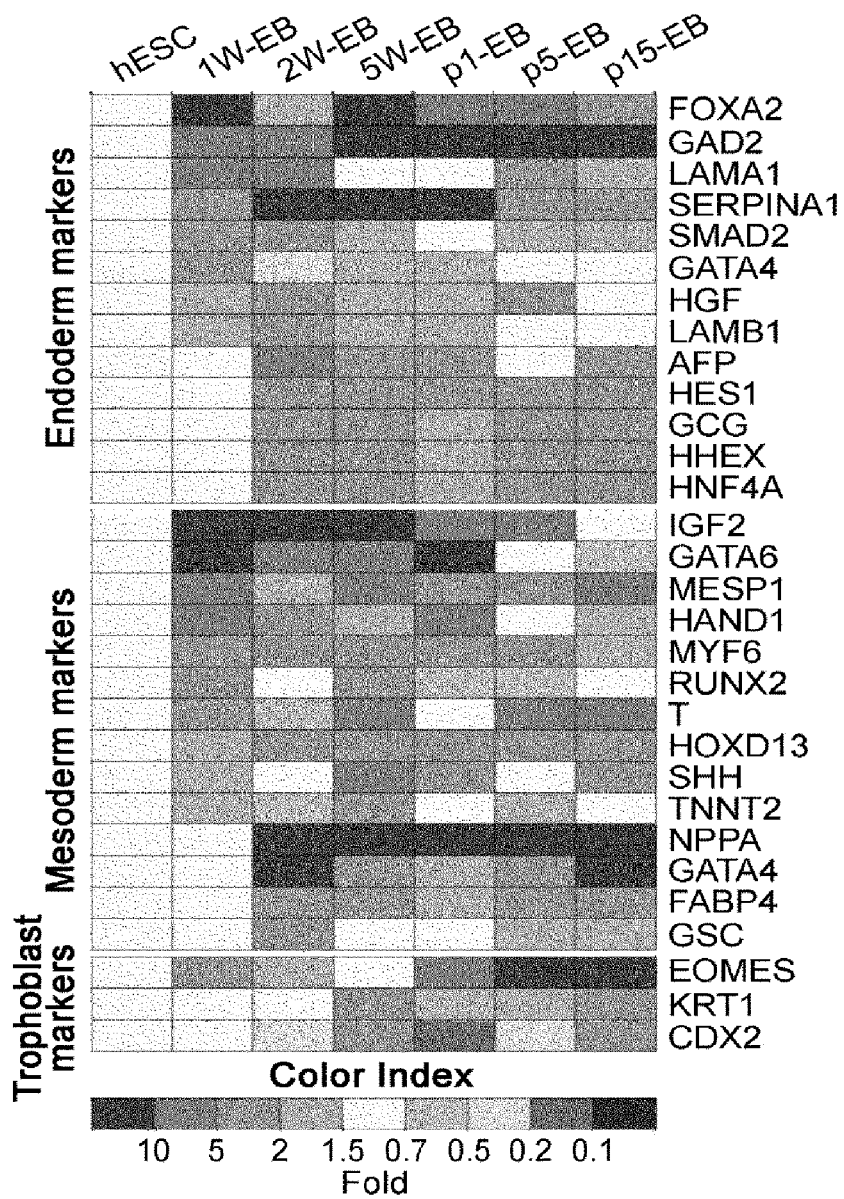

According to one preferred embodiment, gene expression patterns during the simple continuous culture or the periodic passaging after division of embryoid bodies were examined by microarray. The result showed that expression patterns of 18,943 genes (All Flag P) with reliable signal intensity were observed in each of the embryoid bodies under continuous culture or under continuous subculture, and relationships between 1-EBs and 2w-EBs, and p15-EBs and p5-EBs were relatively high, compared to 1w-EBs (p0) and 5w-EBs (FIG. 6a), and gene expression was equally regulated during continuous subculture. Next, the present inventors examined the differentiation potential by changes in gene expression during the subculture of embryoid bodies. As a result, compared to hESC H9, hESC marker genes were down-regulated in embryoid bodies under both continuous culture and continuous subculture, and in particular, hESC marker genes such as POU5F1, NANOG, and LEFTY1 were remarkably down-regulated under all conditions (FIGS. 6b to 6c). To support complexity of the embryoid bodies, the present inventors examined various differentiation markers including ectoderm, endoderm, mesoderm, and trophoblast markers. As a result, 70% or more of the differentiation markers were up-regulated at least 1.5-fold in all of the embryoid bodies under continuous subculture. Therefore, all gene expression patterns of the lineage specific markers showed that differentiation potential was maintained in embryoid bodies (p1, p5, and p15-EBs) under continuous subculture as well as in the embryoid bodies (1w and 5w-EBs) under continuous culture. These results indicate that the potential to differentiate into various lineages is maintained in embryoid bodies during propagation through continuous subculturing.

In another aspect, the present invention relates to an EBD (embryoid body divider) for dividing embryoid body, characterized in that the EBD includes a body having a top with no cutting edge and a bottom with a cutting edge; and a micropatterning part being attached to the bottom surface of the body so as to function to cut and divide embryoid bodies, and the body and the micropatterning part are made of stainless-steel or carbon steel.

In the present invention, a handle is additionally attached to the EBD for dividing embryoid body, thereby providing a manual EBD for dividing embryoid body.

In the present invention, the EBD for dividing embryoid body may be a manual EBD or an automatic EBD. The descriptions of the EBD for dividing embryoid body are the same as above.

In still another aspect, the present invention relates to a culture vessel for embryoid body, in which its top is 1,000-8,000 μm width, its bottom is 100-8,000 μm width, and its depth is 2,000-20,000 μm, and the groove in the bottom of the culture vessel is one or more selected from the group consisting of flat, round, square, and V-shaped grooves, and the surface of the culture vessel is coated with one selected from the group consisting of polylysine, collagen, gelatin, laminin, cell matrix component, and nanopolymer.

In the present invention, the culture vessel for embryoid body may be a single culture vessel or a multi-well plate. The descriptions of the culture vessel for embryoid body are the same as above.

The stem cells produced in the present invention, in particular, embryoid bodies generated from hESCs or hiPSCs can be used as a source for obtaining lineage-specific differentiated cells or differentiation precursor cells, and also used as a biological cell source for applications in cell therapy and drug discovery for the treatment of various diseases.

Hereinafter, the present invention will be described in more detail with reference to Examples. However, these Examples are for illustrative purposes only, and the invention is not intended to be limited by these Examples.

Example 1

Culture of Human Embryonic Stem Cells and Induced Pluripotent Stem Cells (iPSC)

Human embryonic stem cells (hESC) H9 ((NIH Code, WA09; WiCell Research Institute, Madison, Wis.) and H1 (NIH Code, WA01; WiCell Research Institute), and induced pluripotent stem cells (hiPSC) were routinely maintained on γ-irradiated mouse embryonic fibroblasts (MEFs) in hESC culture medium consisting of 80% DMEM/F12 medium, 20% knockout serum replacement (KSR, Invitrogen, Carlsbad, Calif.), 1% non-essential amino acids (NEAA, Invitrogen), 1 mM L-glutamine (Invitrogen), 0.1 mM β-mercaptoethanol (Sigma, St. Louis, Mo.) and 6 ng/ml basic fibroblast growth factor (bFGF, Invitrogen). The cells were passaged using 1 mg/ml collagenase IV (Invitrogen) every 5-6 days. Human newborn foreskin fibroblasts (hFF, ATCC, catalog number CRL-2097; American Type Culture Collection, Manassas, Va.) were cultured in DMEM medium containing 10% FBS (fetal bovine serum, Invitrogen), 1% non-essential amino acids, 1 mM L-glutamine, and 0.1 mM β-mercaptoethanol.

Example 2

Production of Retrovirus and Induction of hiPSC

As disclosed in Takahashi, K. et al. (Cell 131, 861-872, 2007), the pMXs vector containing the human cDNAs of OCT4 (POU5F1), SOX2, c-MYC (MYC) and KLF4 was purchased from Addgene. A packaging cell line GP2-293 was transfected with a retroviral vector DNA and a VSV-G envelope vector using lipofectamine 2000. At 24 hours post-transfection, a primary virus-containing supernatant was collected, and the medium was replaced. After 24 hours, a secondary virus-containing supernatant was collected. The supernatant was filtered using a filter having a pore size of 0.45 μm, and then centrifuged at 20,000 rpm for 90 minutes, and stored at −70° C. before use. For iPSC generation, human foreskin fibroblasts (hFFs) were inoculated in a gelatin-coated 6-well plate at a density of $1 \times 10^5$ cells per well at 6 hours before transduction, and infected at a M.O.I of 5 in the presence of polybrene (6 μg/ml). At 5 days post-transduction, hFFs were collected by trypsin treatment, and then re-inoculated on a MEF feeder layer in the gelatin-coated 6-well plate at a density of $5\sim6 \times 10^4$ cells per well. Next day, the medium was replaced with hESC medium supplemented with 10 ng/ml bFGF. The medium was replaced every other day. At 20 days post-transduction, hESC-shaped colonies were obtained, and transferred onto a MEF feeder layer in a 12-well plate, followed by continuous propagation using the hESC culture method.

Example 3

Formation and Propagation of Embryoid Bodies

To induce formation of embryoid bodies (EB), the present inventors performed three different methods. In the first conventional method, hESCs were harvested with collagenase IV (1 mg/ml), and 1 colony of hESC was used for the formation of 1 embryoid body, or hESCs were dispersed into small clumps by scraping and pipetting for the formation of embryoid bodies. The resulting hESC clumps were added to a plastic petri dish and cultured in suspension for several days in EB medium consisting of Knockout DMEM (Invitrogen), 20% FBS (Invitrogen), 1% non-essential amino acids, 1 mM L-glutamine, 0.1 mM β-mercaptoethanol, and 1% penicillin/streptomycin. During this procedure, two different sized heterogeneous embryoid bodies may be formed. In the second method, hESCs were collected into regular size (600×600 μm) using a McIlwain tissue chopper or a sterile needle to produce uniform embryoid bodies. The clumps were treated with collagenase IV, and seeded onto plastic petri dishes and cultured continuously in suspension for the indicated periods in EB medium. In the third method, hESCs were collected into regular size (600×600 μm) using a McIlwain tissue chopper or a sterile needle to produce uniform embryoid bodies in the same manner as in the second method. The clumps were treated with collagenase IV, and seeded onto plastic petri dishes and cultured in EB medium for 7 days. The cells were passaged using a McIlwain tissue chopper or a blade. The medium was replaced every other day. For analysis, the embryoid bodies were cultured for the indicated periods, and then harvested.

Example 4

RNA Extraction, Reverse Transcription and PCR Analysis

Total RNA was isolated from the cells using the RNeasy Mini Kit (Qiagen, Valencia, Calif.) and reverse-transcribed using the SuperScript First-strand Synthesis System Kit (Invitrogen) according to the manufacturers' protocols. Semi-quantitative RT-PCR was performed using a platinum Taq SuperMix kit (Invitrogen) under the following conditions: at 94° C. for 3 minutes, 30 cycles of at 94° C. for 30 seconds, at 60° C. for 30 seconds, and at 72° C. for 30 seconds, elongation at 72° C. for 10 minutes. The primer sequences are shown in the following Tables 1 and 2 and SEQ ID NOs. 1 to 78.

TABLE 1

| Gene | Primer (Forward) | Sequence listing |
|---|---|---|
| Endo OCT4 | GACAGGGGGAGGGGAGGAGCTAGG | SEQ ID NO: 1 |
| Endo SOX2 | GGGAAATGGGAGGGGTGCAAAAGAGG | SEQ ID NO: 3 |
| Endo KLF4 | ACGATCGTGGCCCCGGAAAAGGACC | SEQ ID NO: 5 |
| Endo c-Myc | GCGTCCTGGGAAGGGAGATCCGGAGC | SEQ ID NO: 7 |
| For transgene and genomic integration | | |
| Trans OCT4 | GAGAAGGATGTGGTCCGAGTGTG | SEQ ID NO: 9 |
| Trans SOX2 | GGCACCCCTGGCATGGCTCTTGGCTC | SEQ ID NO: 11 |
| Trans KLF4 | ACGATCGTGGCCCCGGAAAAGGACC | SEQ ID NO: 13 |
| Trans c-Myc | CAACAACCGAAAATGCACCAGCCCCAG | SEQ ID NO: 15 |
| Total OCT4 | GAGAAGGATGTGGTCCGAGTGTG | SEQ ID NO: 17 |
| Total SOX2 | AGAACCCCAAGATGCACAAC | SEQ ID NO: 19 |
| Total KLF4 | ACCCTGGGTCTTGAGGAAGT | SEQ ID NO: 21 |
| Total c-Myc | CCTACCCTCTCAACGACAGC | SEQ ID NO: 23 |
| Nanog | CAAAGGCAAACAACCCACTT | SEQ ID NO: 25 |
| hTERT | CGGAAGAGTGTCTGGAGCAA | SEQ ID NO: 27 |
| TDGF | TCCTTCTACGGACGGAACTG | SEQ ID NO: 29 |
| Rex1 | AATGCGTCATAAGGGGTGAG | SEQ ID NO: 31 |
| Pax6 | GCCAGCAACACACCTAGTCA | SEQ ID NO: 33 |
| NCAM | AGGAGACAGAAACGAAGCCA | SEQ ID NO: 35 |
| GFAP | CCTCTCCCTGGCTCGAATG | SEQ ID NO: 37 |

TABLE 1 -continued

| Gene | Primer (Forward) | Sequence listing |
|---|---|---|
| GATA2 | AAGGCTCGTTCCTGTTCAGA | SEQ ID NO: 39 |
| cTnT | GGCAGCGGAAGAGGATGCTGAA | SEQ ID NO: 41 |
| Tbx20 | CTGAGCCACTGATCCCCACCAC | SEQ ID NO: 43 |
| GATA6 | CCATGACTCCAACTTCCACC | SEQ ID NO: 45 |
| a-FP | ACTGCAATTGAGAAACCCACTGG | SEQ ID NO: 47 |
| Amylase | GCTGGGCTCAGTATTCCCCAAAT | SEQ ID NO: 49 |
| Albumin | CCTTTGGCACAATGAAGTGGGTA | SEQ ID NO: 51 |
| GAPDH | GAAGGTGAAGGTCGGAGTC | SEQ ID NO: 53 |
| GSC | TCTCAACCAGCTGCACTGTC | SEQ ID NO: 55 |
| OTX1 | CACTAACTGGCGTGTTTCTGC | SEQ ID NO: 57 |
| OTX2 | CACTTCGGGTATGGACTTGC | SEQ ID NO: 59 |
| Flk1 | CATATCTGTCCTGATGTGATATGTC | SEQ ID NO: 61 |
| HEB1 | TGCATGTGGATCCTGAGAAC | SEQ ID NO: 63 |
| E-cadherin | CCTGGTTCAGATCAAATCCAAC | SEQ ID NO: 65 |
| Col1 | GGACACAATGGATTGCAAGG | SEQ ID NO: 67 |
| Col2 | CCGCGGRGAGCCATGATTCG | SEQ ID NO: 69 |
| Musashi1 | ACCCCCACATTCTCTCACTG | SEQ ID NO: 71 |
| Sox1 | GGGAAAACGGGCAAAATAAT | SEQ ID NO: 73 |
| Tuj1 | ACCTCAACCACCTGGTATCG | SEQ ID NO: 75 |
| Nestin | AACAGCGACGGAGGTTCTCTA | SEQ ID NO: 77 |

TABLE 2

| Gene | Primer (Reverse) | Sequence listing |
|---|---|---|
| Endo OCT4 | CTTCCCTCCAACCAGTTGCCCCAAAC | SEQ ID NO: 2 |
| Endo SOX2 | TTGCGTGAGTGTGGATGGGATTGGTG | SEQ ID NO: 4 |
| Endo KLF4 | TGATTGTAGTGCTTTCTGGCTGGGCTCC | SEQ ID NO: 6 |
| Endo c-Myc | TTGAGGGGCATCGTCGCGGGAGGCTG | SEQ ID NO: 8 |
| For transgene and genomic integration | | |
| Trans OCT4 | CCCTTTTTCTGGAGACTAAATAAA | SEQ ID NO: 10 |
| Trans SOX2 | TTATCGTCGACCACTGTGCTGCTG | SEQ ID NO: 12 |
| Trans KLF4 | TTATCGTCGACCACTGTGCTGCTG | SEQ ID NO: 14 |
| Trans c-Myc | TTATCGTCGACCACTGTGCTGCTG | SEQ ID NO: 16 |
| Total OCT4 | CAGAGGAAAGGACACTGGTCCC | SEQ ID NO: 18 |

TABLE 2 -continued

| Gene | Primer (Reverse) | Sequence listing |
|---|---|---|
| Total SOX2 | ATGTAGGTCTGCGAGCTGGT | SEQ ID NO: 20 |
| Total KLF4 | ACGATCGTCTTCCCCTCTTT | SEQ ID NO: 22 |
| Total c-Myc | CTCTGACCTTTTGCCAGGAG | SEQ ID NO: 24 |
| Nanog | ATTGTTCCAGGTCTGGTTGC | SEQ ID NO: 26 |
| hTERT | GGATGAAGCGGAGTCTGGA | SEQ ID NO: 28 |
| TDGF | AGAAATGCCTGAGGAAAGCA | SEQ ID NO: 30 |
| Rex1 | TCAATGCCAGGTATTCCTCC | SEQ ID NO: 32 |
| Pax6 | TGTGAGGGCTGTGTCTGTTC | SEQ ID NO: 34 |
| NCAM | GGTGTTGGAAATGCTCTGGT | SEQ ID NO: 36 |
| GFAP | GGAAGCGAACCTTCTCGATGTA | SEQ ID NO: 38 |
| GATA2 | TCTCCTGCATGCACTTTGAC | SEQ ID NO: 40 |
| cTnT | GAGGCACCAAGTTGGGCATGAAC | SEQ ID NO: 42 |
| Tbx20 | CTCAGGATCCACCCCCGAAAAG | SEQ ID NO: 44 |
| GATA6 | ACGGAGGACGTGACTTCGGC | SEQ ID NO: 46 |
| a-FP | CGATGCTGGAGTGGGCTTTTTGTG | SEQ ID NO: 48 |
| Amylase | GACGACAATCTCTGACCTGAGTAG | SEQ ID NO: 50 |
| Albumin | CAGCAGTCAGCCATTTCACCATAG | SEQ ID NO: 52 |
| GAPDH | GAAGATGGTGATGGGATTTC | SEQ ID NO: 54 |
| GSC | GGCGGTTCTTAAACCAGACC | SEQ ID NO: 56 |
| OTX1 | AGGCGTGGAGCAAAATCG | SEQ ID NO: 58 |
| OTX2 | CGGGTCTTGGCAAACAGTG | SEQ ID NO: 60 |
| Flk1 | CATAGCATGTCTTATAGTCATTGTTC | SEQ ID NO: 62 |
| HEB1 | CGACAGCAGACACCAGCTT | SEQ ID NO: 64 |
| E-cadherin | GTCACCTTCAGCCATCCTG | SEQ ID NO: 66 |
| Col1 | TAACCACTGCTCCACTCTGG | SEQ ID NO: 68 |
| Col2 | CAGGCCCAGGAGGTCCTTTGGG | SEQ ID NO: 70 |
| Musashi1 | AAACCCAAAACACGAACAGC | SEQ ID NO: 72 |
| Sox1 | CCATCTGGGCTTCAAGTGTT | SEQ ID NO: 74 |
| Tuj1 | GGGTACCACTCCACGAAGTA | SEQ ID NO: 76 |
| Nestin | TTCTCTTGTCCCGCAGACTT | SEQ ID NO: 78 |

Example 5

In Vitro Differentiation

For spontaneous differentiation of embryoid body (EB), hiPSCs were dissociated by treatment of 1 mg/ml collagenase IV (Invitrogen), and placed in a petri dish containing knockout DMEM (Invitrogen) consisting of 10% knockout serum replacement, non-essential amino acids, β-mercaptoethanol, L-glutamine, and penicillin/streptomycin. After suspension culture for 6 days, the embryoid bodies were transferred to a gelatin-coated plate, and cultured in the same medium for 10 days. The medium was replaced, if necessary.

Example 6

Induction of Neuroectodermal Spheres for Differentiation of Neural Stem Cells For induction of neuroectodermal spheres (NES), human embryoid bodies were cultured in a NES culture medium (DMEM/F12 (Invitrogen) supplemented with 1×N2/B27, 20 ng/ml epidermal growth factor (Invitrogen), 20 ng/ml bFGF, 10 ng/ml leukocyte inhibitory factor (Sigma) and 100 U/ml penicillin-streptomycin). In this step, the cell was designated as P1 (passage 1). The culture medium was replaced every other day, and NES cells subcultured every week using a McIlwain tissue chopper (Surrey, Gomshall, Mickle Engineering, UK).

Example 7

Osteoblast Differentiation

The human embryoid bodies were plated in Matrigel-coated dishes and cultured in a medium containing osteogenic supplements and 0.1 mM L-ascorbic acid (Sigma), 10 mM β-glycerophosphate (Sigma), and 0.1 mM dexamethasone (Sigma). The culture medium was replaced every other day.

Example 8

Cardiomyocyte Differentiation

The human embryoid bodies were plated in gelatin-coated cell culture dishes in a differentiation medium consisting of knockout DMEM (Invitrogen), 20% FBS (Invitrogen), 1% non-essential amino acids, 1 mM L-glutamine, 0.1 mM β-mercaptoethanol, and 1% penicillin/streptomycin. The culture medium was replaced every other day.

Example 9

Immunocytochemistry

For immunocytochemistry, cells that had been cultured on gelatin-coated 4-well Lab-Tek chamber slides (Nunc, Naperville, Ill.) were fixed with 4% paraformaldehyde, permeabilized in PBS/0.2% BSA/0.1% Triton X-100 and blocked with 4% normal donkey serum (Molecular Probes, Eugene, Oreg., USA) in PBS/0.2% BSA for 1 hour at room temperature. After washing, the cells were incubated with FITC- or Alexa 594-conjugated secondary antibodies (Invitrogen) in PBS/0.2% BSA for 1 hour at room temperature. Nuclei were then counterstained with 10 µg/ml DAPI (4',6-diamidino-2-phenylindole). The chamber slides were analyzed using an Olympus microscope or an Axiovert 200 M microscope (Carl Zeiss, Gottingen, Germany). The antibodies used are listed in the following Table 3.

TABLE 3

| Antibodies | Catalog No. | Company | Dilution |
|---|---|---|---|
| In vitro differentiation | | | |
| anti-TUJ1 | PRB-435P | Covance | 1:500 for immunostaining |
| anti-NESTIN | MAB5326 | Chemicon | 1:100 for immunostaining |
| anti-AFP | A8453 | Sigma | 1:500 for immunostaining |
| anti-SOX17 | MAB1924 | R&D | 1:50 for immunostaining |
| anti-a-SMA | A5228 | Sigma | 1:400 for immunostaining |
| anti-desmin | AB907 | Chemicon | 1:30 for immunostaining |
| Directed differentiation | | | |
| anti-hOsteocalcin | MAB1419 | R&D | 1:100 for immunostaining |
| anti-a-hTroponin T | MAB1874 | R&D | 1:10 for immunostaining |
| anti-MHC | 05-833 | Upstate | 1:100 for immunostaining |
| anti-Nkx2.5 | AF2444 | R&D | 1:40 for immunostaining |
| anti-GFAP | MAB3402 | GFAP | 1:200 for immunostaining |
| anti-O4 | MAB345 | Chemicon | 1:50 for immunostaining |

Example 10

Western Blot Analysis

The human embryoid bodies were lysed using an RIPA buffer containing 50 mM Tris, pH 8.0, 150 mM NaCl, 1% NP-40, 0.1% SDS, 0.5% deoxycholic acid, 1 mM PMSF and protease inhibitor cocktail (IN, Indianapolis, Roche Applied Science) on ice for 15 minutes, followed by centrifugation at 4° C., 20,000×g for 10 minutes. The supernatant was re-centrifuged for 10 minutes, and then the protein concentration was determined using a BCA protein quantification kit (Rockford, Pierce, Ill.). The protein (20 µg) was separated by SDS PAGE (polyacrylamide gel electrophoresis), and electrically transferred onto a PVDF (polyvinylidene fluoride) membrane (Millipore Corp, Mass., Bedford). The membrane was blocked with PBS containing 0.1% Tween-20 and 5% skim milk at room temperature for 2 hours, and reacted for 1 hour with primary antibodies including anti-phospho-Akt (Cell Signaling, Ser473, 1:1000), anti-Akt (1:1000, Cell Signaling), cleaved Caspase-3 (1:1000, Cell Signaling, 5A1) and anti-β-actin (1:5000, Sigma) diluted in PBS containing 0.1% Tween-20. After washing, the membrane was reacted with anti-rabbit HRP-conjugated antibodies or anti-mouse HRP-conjugated secondary antibodies (Amersham, Ill., Arlington Heighs), and visualized using an ECL Advance kit (Amersham) and LAS-3000 (Fujifilm, Tokyo, Japan). Bands were analyzed for density with Image Gauge software (Fuji Photo Film GMBH, Dusseldorf) and normalized to loading control (β-actin). All experiments were performed in triplicate. Error bars represent the standard errors of the means (n=3).

Example 11

Cell Cycle Analysis

The embryoid bodies were isolated as single cells, and approximately $1 \times 10^6$ cells were counted and used for analysis. The cells were washed with PBS, and fixed in ice-cold 100% ethanol, and reacted at 4° C. for 30 minutes. Thereafter, the cells were washed with PBS, and then reacted with 1 ml of staining reagent (20 µg/ml, propidium iodide/10 µg/ml RNase) at room temperature for 30 minutes. The cells were analyzed by FACS (fluorescence-activated cell sorting) using a FACSCalibur (BD Biosciences, Franklin Lakes, N.J.), and cell cycle distribution was determined using WinMDI (The Scripps Institute, Flow Cytometry Core Facility, La Jolla, Calif.; version 2.8).

Example 12

BrdU Binding Analysis

The human embryoid bodies were treated with trypsin, and cultured in Matrigel-coated 4-well LabTec chamber slides for 4 days for BrdU (5-Bromo-20-deoxyuridine (BrdU; BD Pharmingen, San Diego, Calif.) binding analysis. For BrdU binding, the cells were incubated in the presence of 10 μM BrdU for 1 hour. After washing with PBS, the cells were fixed in 4% formaldehyde for 15 minutes, and then reacted with 1N HCl at room temperature for 15 minutes. After washing the sample, 0.1 M sodium borate was added, and reacted for 15 minutes. After washing, the cells were reacted with anti-BrdU antibody (1:100; BD Pharmingen) diluted in PBS supplemented with 3% BSA for 60 minutes, and then reacted with FITC-conjugated secondary antibody (Invitrogen) for 30 minutes. The nuclei were visualized with DAPI. After washing the cells with PBS, a coverslip was mounted, and then observed under an Olympus microscope equipped with a fluorescence detector (IX51, Olympus, Japan). The mean±S.E. number of BrdU positive cells per field of vision was measured. At least 4 visual fields per coverslip were counted.

Example 13

Apoptosis Analysis

Apoptosis analysis of human embryoid bodies was performed by flow cytometry using an Annexin-V-FITC apoptosis detection kit I (BD Bioscience) according to the manufacturers' protocols. Briefly, cells were recovered as described above, and single-cell suspension was prepared by treatment of trypsin. A pro-apoptotic agent, camptothecin (Sigma) was used as a positive control at 5 μM in DMSO and incubated for 5 hours. $1\times10^6$ cells/ml were suspended in a binding buffer, stained with Annexin V and propidium iodide for 15 minutes. Then, the cells were diluted in the binding buffer at 1:1, and filtered, followed by flow cytometry using a FACScalibur (Becton Dickinson). The data was analyzed by WinMDI.

Example 14

Protein Oxidation Assay

Protein oxidation was detected by measuring carbonyl contents using a kit according to the manufacturers' protocols (Oxyblot, Millipore, Billerica, Mass.). Total proteins were isolated from 1w-EBs, 5w-EBs, p1-EBs and p5-EBs using an RIPA buffer containing 50 mM Tris, pH 8.0, 150 mM NaCl, 1% NP-40, 0.1% SDS, 0.5% deoxycholic acid, 1 mM PMSF and protease inhibitor cocktail (Roche Applied Science, Indianapolis, Ind.). For protein quantification (BCA method, Pierce Biotechnology, Rockford, Ill.), the supernatant was removed, and 2-mercaptoethanol (final concentration of 1%) was added to prevent further oxidation. After derivatization of the carbonyl group with 2,4-dinitrophenyl hydrazine, proteins were separated in a 10% SDS-PAGE gel and transferred onto a PVDF membrane (Immobilon-P, Millipore). Thereafter, the membrane was reacted with anti-dinitrophenyl primary antibody (1:150), and then reacted with goat anti-rabbit IgG (1:300). Immunoreactive proteins were visualized using an ECL Advanced kit (Amersham) and LAS-3000 (Japan, Tokyo, Fujifilm).

Example 15

Microarray Analysis

Total RNAs isolated from hESCs, 1w-EBs, 2w-EBs, 5w-EBs, p1-EBs, p5-EBs and p15-EBs were extracted using an RNA Mini kit (Qiagen), and labeled with Cy3, and hybridized to Agilent whole human genome 4X44K microarrays (one color-based) according to the manufacturers' protocols. Hybridized images were scanned using an Agilent DNA microarray scanner, and quantified using Feature extraction software (Agilent Technology, Palo Alto, Calif.). All data were normalized, and fold-changed genes were selected using GeneSpringGX 7.3 (Agilent Technology, USA). The averages of the normalized ratios were calculated by dividing the average of the normalized signal channel intensity by the average of normalized control channel intensity. Functional annotation of genes performed according to the Gene Ontology™ Consortium (http://www.geneontology.org/index.shtml) using GeneSpringGX 7.3. Gene classification was based on searches in BioCarta (http://www.biocarta.com/), GenMAPP (http://www.genmapp.org/), DAVID (http://david.abcc.ncifcrf.gov/), and Medline databases (http://www.ncbi.nlm.nih.gov/).

Example 16

EBD for Dividing Embryoid Body

FIG. 10 shows an EBD for dividing embryoid bodies according to one embodiment of the present invention.

An EBD (10) for dividing embryoid body is composed of a body (11) and a micropatterning part (12) for cutting. The body (11) has various shapes according to the shape of the culture vessel for culturing cells and the intended purpose. In the embodiment of the present invention, the circular-shaped (A) or square-shaped (B) body is disclosed. However, the scope of the present invention is not limited thereto, and it is possible to fabricate the body having any of polygonal shapes such as triangle, pentagonal, and hexagonal shapes.

In the one well-based MEBD (FIGS. 12A and 12B) having one body and one micropatterning part, a single embryoid body can be divided by placing it in one well having a diameter of 100 μm or larger (FIGS. 12C and 12D).

The one well-based MEBD can be fabricated by attaching a handle (15) for convenient operation, as shown in FIG. 10E.

The micropatterning part (12) is placed on the upper surface of the body (11). As shown in FIG. 10, one micropatterning part may be placed on each body, or as shown in FIG. 13, a plurality of micropatterning parts may be repeatedly placed thereon.

As shown in FIG. 11, each micropattern part has various shapes according to the desired size and the intended purposes. That is, in the present Example of the present invention, the micropattern is disclosed to have a cross shape (×). However, the scope of the present invention is not limited thereto, and the micropattern may have various shapes (circular, triangle, square, hexagon) including a straight type (−) or a cross type (×).

As shown in FIGS. 10C and 10D, the micropatterning part (12) may be enclosed by a wall (14) surrounding the micropatterning part. This wall is advantageous in that it makes the embryoid body trapped in the stamp upon division of embryoid body.

In regard to the cutting edge of the micropatterning part of the EBD for dividing embryoid body, its height (13) is preferably 0.1 μm higher than that of the vessel/well, and its width (14) is preferably 0.1 μm smaller than that of the vessel/well.

As shown in FIG. 13, the stamp having a repeated plurality of micropatterning parts is advantageous in that a large amount of embryoid bodies can be divided at a time by directly applying the stamp to a culture vessel, a culture vessel having a grid (21), or a multi-well plate, where embryoid bodies are attached to match with the micropatterning parts.

The multi-well-based MEBD can be fabricated by attaching a handle for convenient operation, as shown in FIG. 13I.

Example 17

Division Method of Embryoid Bodies Using EBD

FIG. 18 shows a division method of embryoid bodies using EBD according to one embodiment of the present invention.

For the preparation of stem cell-derived embryoid bodies, embryoid bodies are generated according to the in vitro differentiation method of Example 5, and placed in the culture vessel for division. In detail, for the generation of embryoid bodies, human embryonic stem cells (hESCs) and human induced pluripotent stem cells (hiPSCs) were dissociated by treatment of 1 mg/ml collagenase IV (Invitrogen), and transferred in new petri dishes containing knockout DMEM (Invitrogen) supplemented with 10% knockout serum replacement, non-essential amino acids, (β-mercaptoethanol, L-glutamine and penicillin/streptomycin, followed by suspension culture for 6 days. The medium was replaced, if necessary. When the embryoid bodies grow to have a suitable size, they are placed in culture vessels. The preparation methods of embryoid bodies can be classified into 4 methods. First, embryoid bodies cultured in suspension are transferred in another culture vessel for division (FIGS. 12C and 12D). Second, embryoid bodies cultured in suspension are transferred in another coated culture vessel for division (FIGS. 12E and 12H). Third, embryoid bodies cultured in suspension are transferred in another coated grid culture vessel for division (FIG. 13E). At this time, one embryoid body is placed in one grid. Fourth, embryoid bodies are cultured in an EB size-fitted micro-well plate for culture and division (FIG. 13F), or embryoid bodies cultured in suspension are transferred in the micro-well plate for division. That is, it is possible to perform the generation, culture, and division steps of embryoid bodies in a single vessel/plate, and the steps can be performed in various micro/multi-well plates (FIGS. 13F to 13H). Approximate sizes of various EB vessels are shown in Tables 4 to 5.

TABLE 4

Multi-well plate for EB

| | Well Volume (uL) | Well Depth (mm) | Well Diameter (top/bottom) (mm) | Plate Length (mm) | Plate Width (mm) | Plate Height (mm) | A1 Row Offset (mm) | A1 Column Offset (mm) |
|---|---|---|---|---|---|---|---|---|
| 384 well flat bottom | 112 | 11.43 | 3.63/2.67 (width) | 127.8 | 85.5 | 14.2 | 8.99 | 12.12 |
| 384 well PP round bottom block | 180 | 25.11 | 3.63 (top width) | 127.8 | 85.5 | 27.8 | 8.99 | 12.12 |
| 384 well PP V- Bottom block | 180 | 22.4 | 3.58/3.23 | 27.3 | 85.3 | 24.94 | 8.94 | 11.94 |
| 1536 well solid flat bottom | 12.8 | 4.8 | 1.8/1.63 | 127.8 | 85.5 | 10.4 | 7.86 | 11.0 |
| 1536 well solid, round bottom | 10 | 5.01 | 1.69/0.74 | 127.8 | 85.5 | 10.4 | 7.86 | 11.0 |

TABLE 5

Multi-well plate for EB

| | Well center to well center spacing (mm) | Flange or skirt height (mm) | Stack Height | Well Bottom Elevation (mm) | Well Bottom Thickness (mm) | Well Bottom Area (cm2) | Distance to bottom of plate |
|---|---|---|---|---|---|---|---|
| 384 well flat bottom | 4.5 | 6.096 | 13.15 | 2.794 | 1.27 | 0.056 | 1.5 |
| 384 well PP round bottom block | 4.5 | 6.096 | 26.71 | N/A | N/A | N/A | |
| 384 well PP V- Bottom block | 4.5 | 2.51 | 23.42 | 2.54 | 1.02 | 0.322 | |
| 1536 well solid flat bottom | 2.25 | 2.16 | 8.9 | 5.6 | 0.076 | 0.0209 | 5.524 |

TABLE 5-continued

| Multi-well plate for EB | | | | | | |
|---|---|---|---|---|---|---|
| Well center to well center spacing (mm) | Flange or skirt height (mm) | Stack Height | Well Bottom Elevation (mm) | Well Bottom Thickness (mm) | Well Bottom Area (cm2) | Distance to bottom of plate |
| 1536 well solid, round bottom  2.25 | 2.16 | 8.7 | 5.41 | 0.9 | N/A | 4.49 |

As shown in FIG. 18, one or more embryoid bodies are stacked in one vessel, and a plurality of embryoid bodies can be divided by a single application of pressure. In this case, a plurality of embryoid bodies are placed or attached in one well plate at the same time by stacking one or more embryoid bodies (FIGS. 17B and 17C).

Meanwhile, the EB size-fitted micro-well plate (FIGS. 13F and 17B) can be also directly used for division, after used for culture.

A flow chart of the division method of embryoid bodies is illustrated in FIGS. 16 and 18.

After preparation of embryoid bodies, the EBD for dividing embryoid body is placed on the top of the culture vessel or multi-well plate horizontally, as shown in FIGS. 13A to 13D.

If adhesion of embryoid body is necessary in the present invention, polylysine, collagen, gelatin, laminin, cell matrix component, nanopolymer or the like can be added and coated (FIGS. 12E to 12H).

Thereafter, the embryoid bodies are divided by applying a predetermined pressure downward using the EBD for dividing embryoid body, and then the EBD for dividing embryoid body is carefully lifted up for removal without damaging the cells.

As shown in FIG. 14, each of the embryoid bodies is divided into several pieces according to the shape of the micropatterning part of the EBD for dividing embryoid body. The unit of embryoid bodies divided by the stamp includes a predetermined number of cells.

The embryoid bodies thus divided are dispersed in culture medium by pipetting or scraping, and then used for various purposes including subculture.

According to the EB division method using the EBD for dividing embryoid body of the present invention, embryoid bodies can be easily divided into an EB unit having uniform size and number, and also divided into a desired size according to the intended purpose. Since the embryoid bodies can be also divided into a cell unit having a uniform number of cells, variation in the number of cells that may occur in every subculture can be reduced, thereby ensuring higher reproducibility of research and experiment.

Example 18

Automatic EBD Using EBD (AEBD)

To divide the cultured embryoid bodies under the same conditions using the EBD for dividing embryoid bodies according to the present invention, and to increase reproducibility of repeated experiments, the pressure and speed of the stamp applied to the cell surface should be constant maintained.

Therefore, an automatic method can be proposed, in which the pressure and speed of the EBD for dividing embryoid body according to the example of the present invention are optimized, and then the EBD is mounted in a device, and a guide such as a rail is attached thereto for movement in a vertical direction, and constant pressure is applied to the embryoid bodies in the culture vessel placed on the platform for division or patterning. This method is advantageous over the manual method in that the patterns can be made more rapidly and precisely.

To solve this problem, the present inventors have developed an automatic EBD (AEBD) capable of automatically pressing and dividing embryoid bodies using the EBD for dividing embryoid body.

FIG. 19 is a perspective view of automatic EBD using the stamp according to one embodiment of the present invention. As depicted, the automatic EBD consists of a body and a chopping arm (A). Various EBD heads for cutting, including a straight type (−) such as a feather blade or a cross type (+), can be fixed in the chopping arm, and the cutting head can be fabricated according to the size and shape of the division vessel, and the cutting edge of the micropatterning part can be fabricated in various combinations of size and shape. One or more EBD heads can be mounted in the cutting head according to the size and shape of the division vessel, or the intended purpose.

<Results>

Experimental Example 1

Identification of the Propagation of Embryoid Bodies

Generally, formation of embryoid bodies is an intermediate step of in vitro tissue-specific differentiation of hESCs and hiPSCs into three germ layers. The embryoid bodies generated by the conventional collagenase IV treatment are heterogeneous in the size and shape, which results in a limited developmental potential and a low production yield. Therefore, formation of size-controlled embryoid bodies for reproducible differentiation of hESCs and hiPSCs was performed using a tissue chopper.

As a result, more uniform-sized embryoid body populations are formed, compared to the embryoid bodies formed by the enzymatic treatment. However, after continuous culture for 5 weeks, an increase in heterogeneity and cell debris was observed in irregular-sized embryoid body populations, and no propagation ability was observed in the culture (FIGS. 1a, 1b and 7b). Therefore, to expand the limit of embryoid bodies provided as an intermediate for general differentiation, there is a need for large-scale production of embryoid bodies. Accordingly, the present inventors have developed the method of FIG. 1a, which allows the prolonged propagation by periodic passaging. The hESC colonies were collected into a size of 600 μm, and regular-sized embryoid bodies were formed by enzymatic treatment of cell clumps (FIG. 1c). After 1 week-incubation, embryoid bodies were sliced at ratios of 1:2, 1:4, and 1:6, and transferred to new suspension culture plates.

Figure 1D:
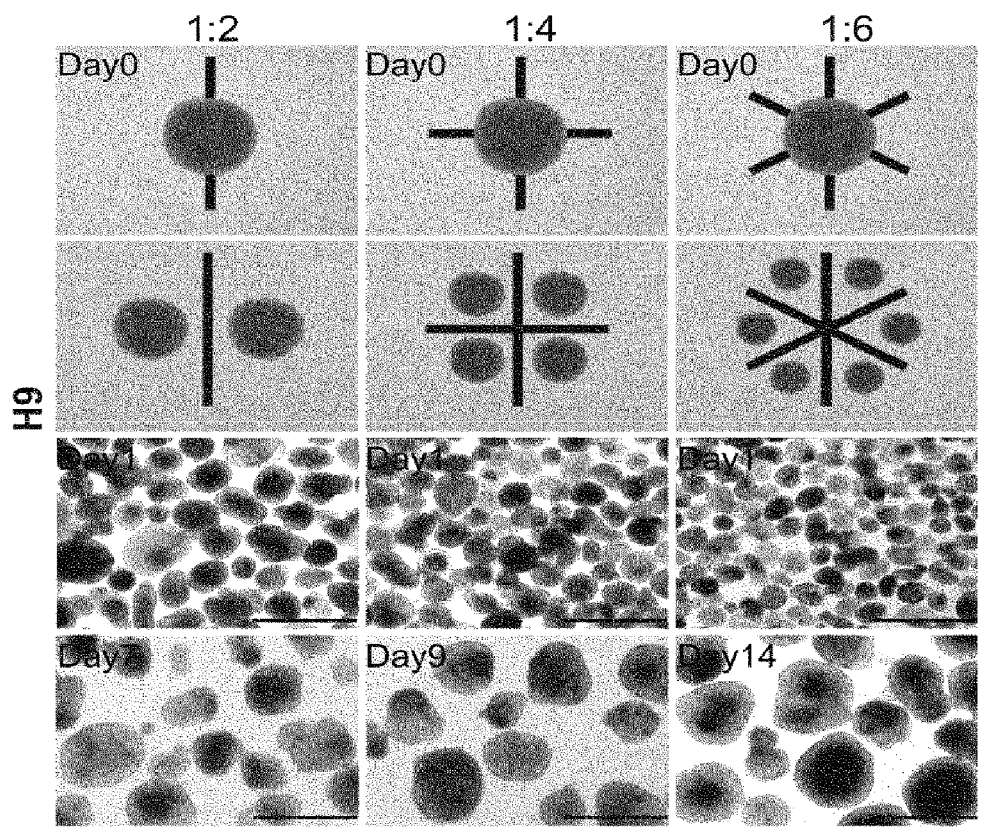

As a result, the passaged embryoid bodies exhibited a uniform size distribution, and after passaging at ratios of 1:2, 1:4, and 1:6, the passaged embryoid bodies showed successful re-growth back to volumes at day 7, 9, and 14 (FIG. 1d)

Experimental Example 2

Maintenance of Cell Growth and Propagation Ability of Passaged Embryoid Bodies

The embryoid bodies cultured by simple continuous culture without passaging (the conventional method) showed a reduction in the growth after 2 weeks, based on the measurement of their diameter (FIG. 2a). 1w-EBs showed active growth for 7 days, whereas 5w-EBs showed no growth during the culture period (FIGS. 7a and 7b). Therefore, the present inventors examined the effect of passaging on the growth of embryoid bodies. The diameter of the embryoid bodies measured during 2 passages of suspension culture showed re-growth back to diameters at the indicated ratios, and additional growth of embryoid bodies was maintained during the long-term subculture (p15) (FIGS. 2b and 2c). To evaluate propagation of the passaged embryoid bodies, BrdU binding was analyzed by immunocytochemistry, and phosphorylation of serine/threonine kinase Akt, which plays a critical role in signal transduction pathways involved in cell proliferation, was measured by Western blot analysis.

As a result, embryoid bodies maintained under continuous conditions for 5 weeks displayed a marked decrease in the BrdU binding (56.7±3.2%). In contrast, the passaged embryoid bodies (p1-EBs; 80.7±2.2, and p5-EBs; 85.1±5.2%) displayed an increase in the BrdU binding, equal to that of the control group 1w-EBs (83.2±4.4%) (FIG. 2d). However, no significant change in the phosphorylated Akt levels was observed in all embryoid body samples (FIG. 2d). These results indicate that the proliferation rate of embryoid bodies maintained during continuous subculture.

Experimental Example 3

Subculture of Embryoid Bodies Increases Cell Growth by Prevention of Apoptosis and Cell Cycle Arrest To determine the effect of embryoid body passaging on cell functions, the present inventors examined the effect of embryoid body passaging on apoptosis and cell cycle. Cell survival was examined by monitoring the percentages of cells during apoptosis and necrosis. Apoptosis of the embryoid bodies maintained under the continuous culture and under the subculture was analyzed by annexin-V and PI (propidium iodide) staining (FIGS. 3a to 3c). After continuous culture of 4w-EBs and 5w-EBs, the percentage of annexin-V positive apoptotic cells was 12.30±0.64% and 9.66±0.63%, respectively. This result was examined by the irregular-sized embryoid bodies formed after treatment of collagenase IV (FIG. 8). Thus, the percentage of apoptotic cells increased, as the period of continuous culture increased. In contrast, the embryoid bodies maintained under the continuous subculture showed less than 2% of apoptotic or dead cells (FIGS. 3a to 3c).

Next, the present inventors measured the levels of the cleaved caspase-3 as an apoptotic index, which is generally found in major apoptosis signaling pathways. FIG. 3d shows the increased level of cleaved caspase-3 in 5w-EBs, compared to 1w-EB control, p1-EBs and p5-EBs under proliferation, indicating that the subculture of embryoid bodies prevents apoptosis. Most of the apoptosis-inducing reagents are oxidants or cell oxidation-stimulating agents, and oxidative stress is also known to contribute to apoptosis. To determine whether apoptosis in embryoid bodies under continuous culture is mediated by oxidative stress, Oxyblot analysis was performed to detect the protein oxidation (carbonylation).

As a result, the carbonyl signal was significantly increased in 5 w-EBs compared to 1w-EBs, whereas the signal was decreased in p1-EBs and p5-EBs, similar to that in 1w-EBs (FIG. 3e). These results suggest that the levels of mitochondria and DNA increased, and cells produce a large amount of ATP and ROS (reactive oxygen species) as a by-product via oxidative phosphorylation during differentiation of hESCs into embryoid bodies. Therefore, the present inventors inferred that oxidative stress affects proliferation of embryoid bodies, as well as in vitro differentiation into embryoid bodies.

The effect of embryoid body passaging on cell cycle was examined by flow cytometry in the embryoid bodies under continuous culture and under subculture. As a result, the embryoid bodies under continuous culture showed time-dependent G2/M phase cell accumulation. As a percentage of G2/M phase cells increased, a percentage of S phase cells decreased, and there was no significant change in a percentage of G0/G1 phase cells (FIG. 3f). In contrast, embryoid bodies under subculture displayed no marked differences in the cell-cycle distribution relative to the control group (FIG. 3f).

Overall, the embryoid bodies under continuous culture exhibited G2/M arrest by an increased level of apoptosis and free radical protein damage. It was confirmed that these obstacles are overcome by subculture of embryoid bodies, and thus cell survival is improved by anti-apoptotic signals and cell cycle proceeds continuously.

Experimental Example 4

Subculture of Embryoid Bodies Maintains a Differentiation Potential into Three Germ Layers To demonstrate a differentiation potential of the passaged embryoid bodies of the present invention, the present inventors examined the differentiation potentials of the passaged embryoid bodies derived from H9 and H1 hESCs and hiPSCs in vitro. After suspension culture, embryoid bodies were re-attached to gelatin-coated plates for 10 days under differentiation conditions.

As a result, expressions of differentiation markers, ectoderm (GFAP, NCAM and PAX6), mesoderm (Tbx20, Col1, Col2A1 and cTnT) and endoderm (Amylase) were observed by RT-PCR. In contrast, expressions of OCT4 and NANOG were remarkably reduced (FIG. 4a). Tuj1 (ectoderm), Nestin (ectoderm), desmin (mesoderm), α-SMA (α-smooth muscle actin, mesoderm), Sox17 (endoderm), and AFP (α-fetoprotein, endoderm)-positive cells were detected by immunocytochemistry (FIG. 4b). These results indicate that the passaged embryoid bodies have a potential to differentiate into three germ layers in vitro.

Next, the present inventors examined whether the subcultured embryoid bodies can be directly used as a starting point of differentiation and can be differentiated by the differentiation method. The successful differentiation of the long-term subcultured embryoid bodies (>15 passages) into neural stem cells (NSCs. ectoderm), osteoblasts (mesoderm) and cardiomyocytes (mesoderm) was observed. Expressions of the markers specific for the above differentiated cell types were examined by RT-PCR and immunocytochemistry (FIG. 5).

The differentiation of neuroectodermal spheres (NESs) from 1w-EBs and p15-EB was induced, and the positive staining of neuron marker (Tuj1), oligodendrocyte marker (O4), and astrocyte marker (GFAP) was observed in the Matrigel-coated dishes. At a transcriptional level, the expression levels of NES marker genes such as SOX1, MSI1 and 2, TUJ1, PAX6, and Nestin were increased (FIG. 5a). In addition, differentiation of human embryonic stem cells into osteoblasts was examined by Alizarin red S staining and immunocytochemical analysis of osteocalcin. The mRNA levels of the osteoblast differentiation markers, Runx2, osteorix, osteocalcin, osteoprotegerin, and osteonectin were remarkably increased in osteoblasts derived from 1w-EBs and p15-EBs (FIG. 5b). The differentiation of cardiomyocytes was examined by expressions of cardiomyocytes-specific proteins and genes. Cardiomyocytes positive for anti-MHC, anti-NRx2.5 and anti-cTnT were examined by immunostaining. All of the cardiac transcription factor-encoding genes and the cardiac-specific genes including NRx2.5 and MEF2c were up-regulated in the passaged embryoid body-derived cardiomyocytes, compared to undifferentiated hESCs (FIG. 5c). These results suggest that the subcultured embryoid bodies have pluripotency to differentiate into various cell types, and the differentiation occurs in response to the same signals, independent of continuous subculture.

Experimental Example 5

General Gene Profile of Passaged Embryoid Bodies

In order to examine gene expression patterns during the simple continuous culture or the periodic passaging after division of embryoid bodies, the embryoid body samples prepared by the method described in the above Examples were used to perform a microarray. The changes in the gene expression patterns were analyzed based on fold change and 2 dimensional hierarchical clustering. The result showed that expression patterns of 18,943 genes (All Flag P) with reliable signal intensity were observed in each of the embryoid bodies under continuous subculture. As shown in FIG. 6a, a hierarchical sample tree, as expected by the present inventors, showed relatively high relationships between 1-EBs and 2w-EBs, and p15-EBs and p5-EBs, compared to 1w-EBs (p0) and 5w-EBs. These results indicate that gene expression was equally regulated during continuous subculture.

Next, the present inventors examined the differentiation potential by changes in gene expression during the subculture of embryoid bodies. The hESC-specific markers and lineage-specific markers were selected from all probe sets of Agilent Whole Genome array (44K), and then changes at the transcriptional level were analyzed in embryoid bodies under continuous culture or under continuous subculture, compared to hESC H9 (FIGS. 6b to 6c). The hESC marker genes were down-regulated in embryoid bodies under both continuous culture and continuous subculture, and in particular, hESC marker genes coding such as POU5F1, NANOG, and LEFTY1 were remarkably down-regulated under all conditions. To support complexity of the embryoid bodies, the present inventors examined various differentiation markers including ectoderm, endoderm, mesoderm, and trophoblast markers. As a result, 80% of more of the ectoderm marker and 70% or more of the endoderm and mesoderm markers were up-regulated at least 1.5-fold in all of the embryoid bodies under continuous subculture. Therefore, all gene expression patterns of the lineage specific markers showed that differentiation potential was maintained in embryoid bodies (p1, p5, and p15-EBs) under continuous subculture as well as in the embryoid bodies (1w and 5w-EBs) under continuous culture. "Ingenuity Pathways analysis software" was used to examine the functional connection between the differentially expressed genes, relevant to cell-to-cell signaling, tissue development, cellular movement, and cancer-associated genes, and the results were similarly obtained from each of the embryoid bodies (data not shown). Apoptotic cell death and cell cycle arrest were observed during the continuous culture of embryoid bodies, as described above, and pro-apoptotic or anti-apoptotic gene expressions were examined. The pro-apoptotic genes such as FAS, FASLG, and TNFRSF1A were up-regulated in the embryoid bodies under all conditions, but there was no change in anti-apoptotic genes between the embryoid body samples. BIK, a pro-apoptotic member, was down-regulated in all embryoid bodies under subculture, but up-regulated in 2w-EBs. In addition, BIK was down-regulated in long-term cultured embryoid bodies (5w-EBs), which could be attributed to a feedback mechanism by an abrupt apoptosis. These results indicate that the potential to differentiate into various lineages is maintained in the embryoid bodies during propagation through continuous subculture.

In conclusion, the present inventors demonstrated that production of embryoid body populations can be increased for a long period of time while maintaining their intrinsic characteristics by continuously subculturing embryoid bodies primarily generated from hESCs and hiPSCs without further generation from hESCs and hiPSCs. Therefore, the propagation and maintenance method of embryoid bodies of the present invention could be used for the large-scale production of embryoid bodies with high quality from a small fraction of hESCs and hiPSCs, and could greatly contribute to the future of the stem cell industry and the development of therapeutic agents.

INDUSTRIAL APPLICABILITY

The method of the present invention allows easy, inexpensive, rapid large-scale production of homogenous embryoid bodies from a limited number of stem cells, in particular, hESCs or hiPSCs, and thus can be used for induced differentiation of almost all cell types, and ultimately used for the development of a technique to obtain a large amount of differentiated cells and progenitor cells. Further, a differentiation technique using embryoid bodies generated from patient-derived hiPSCs could greatly contribute to the development of medical industries in the future, provide a rapid and improved method for the application of human stem cell-derived products, and therapy and drug discovery.

What is claimed is:

1. A large-scale method of propagating embryoid bodies generated from stem cells, comprising the steps of:
    (a) culturing the embryoid bodies;
    (b) inducing division of embryoid bodies by mechanical or enzymatic methods; and,
    (c) subculturing the embryoid bodies of step (b) in suspension culture.

2. The method according to claim 1, wherein the stem cells are pluripotent stem cells.

3. The method according to claim 1, wherein the stem cells are embryonic stem cells or induced pluripotent stem cells.

4. The method according to claim 1, wherein the stem cell are derived from human.

5. The method according to claim 1, wherein the embryoid bodies are established by suspension culture of colonies of collected stem cells cut into the dimension of 10 to 1000 μm on all sides, undisturbed embryonic stem cell colonies or induced pluripotent stem cell colonies.

6. The method according to claim 1, wherein the embryoid bodies are established by collecting stem cells cut into ½₀ to ½-sized pieces and then culturing them in suspension.

7. The method according to claim 1, wherein the subculturing is performed 1 to 200 times.

8. The method of claim 1, wherein mechanical division is performed with a device selected from the group consisting of: a blade, a tissue chopper, a needle, a pipette, an EBD (embryoid body divider) or a scraper.

9. The method according to claim 8, wherein the EBD includes a body that has a top having no cutting edge and a bottom having a cutting edge; and a micropatterning part that is attached onto the bottom surface of the body to function to cut and divide embryoid bodies.

10. The method according to claim 8, wherein the EBD is MEBD (manual EBD) or AEBD (automatic EBD).

11. The method according to claim 8, wherein the method using the EBD comprises the steps of: (a) preparing an embryoid body in a coated culture vessel; (b) placing the EBD on the top of the culture vessel horizontally; (c) applying a uniform pressure to the culture vessel using the EBD to divide the embryoid body; and (d) removing the EBD.

12. The method according to claim 11, wherein the culture vessel has a top of 1,000-8,000 μm width, a bottom of 100-8,000 μm width, and a depth of 2,000-20,000 μm; a groove having one selected from the group consisting of flat, round, square, and V-shaped grooves in its bottom; and its surface coated with one selected from the group consisting of polylysine, collagen, gelatin, laminin, cell matrix component, and nanopolymer.

13. The method according to claim 8, wherein the method using the EBD comprises the steps of: (a) preparing an embryoid body in a multi-well plate for EB; (b) placing the EBD on the top of the multi-well plate horizontally; (c) applying a uniform pressure to the multi-well plate using the EBD to divide the embryoid body; and (d) removing the EBD.

14. The method of claim 1, wherein enzymatic division is performed using an enzyme selected from the group consisting of: collagenase, accutase, dispase or trypsin.

15. The method of claim 1, wherein steps (a)-(c) are repeated.

\* \* \* \* \*